(12) United States Patent
Elson et al.

(10) Patent No.: US 8,546,539 B2
(45) Date of Patent: Oct. 1, 2013

(54) FC RECEPTOR-BINDING POLYPEPTIDES WITH MODIFIED EFFECTOR FUNCTIONS

(75) Inventors: Greg Elson, Collonges sous Saleve (FR); Olivier Leger, St.-Sixt (FR)

(73) Assignee: Novimmune S.A., Geneva (CH)

( * ) Notice: Subject to any disclaimer, the term of this patent is extended or adjusted under 35 U.S.C. 154(b) by 1079 days.

(21) Appl. No.: 12/152,395

(22) Filed: May 14, 2008

(65) Prior Publication Data

US 2012/0142098 A1 Jun. 7, 2012

Related U.S. Application Data

(60) Provisional application No. 60/930,276, filed on May 14, 2007.

(51) Int. Cl.
*C07K 16/00* (2006.01)
*C12P 21/08* (2006.01)
*C07K 1/00* (2006.01)

(52) U.S. Cl.
USPC .................. 530/387.1; 530/387.3; 530/388.1; 530/388.15; 530/388.7; 530/388.73

(58) Field of Classification Search
None
See application file for complete search history.

(56) References Cited

U.S. PATENT DOCUMENTS

| | | | |
|---|---|---|---|
| 6,444,206 B1 | 9/2002 | Letureq et al. | 424/141.1 |
| 6,528,624 B1 | 3/2003 | Idusogie et al. | 530/387.3 |
| 6,737,056 B1 | 5/2004 | Presta | 424/133.1 |
| 7,297,775 B2 | 11/2007 | Idusogie et al. | 530/387.1 |
| 7,312,320 B2 | 12/2007 | Elson | 530/388.2 |
| 7,662,925 B2* | 2/2010 | Lazar et al. | 530/387.1 |
| 2005/0265998 A1* | 12/2005 | Elson | 424/143.1 |
| 2006/0024298 A1 | 2/2006 | Lazar et al. | 424/133.1 |
| 2006/0134709 A1 | 6/2006 | Stavenhagen | 435/7.23 |
| 2008/0050366 A1 | 2/2008 | Elson et al. | 424/133.1 |

FOREIGN PATENT DOCUMENTS

| | | |
|---|---|---|
| EP | 1746107 | 1/2007 |
| EP | 1068241 | 10/2007 |
| WO | WO 99/51642 | 10/1999 |
| WO | WO 00/42072 | 7/2000 |
| WO | WO 03/074679 | * 9/2003 |
| WO | WO 2004/099249 | 11/2004 |
| WO | WO 2005/028509 | 3/2005 |
| WO | WO 2005/065015 | 7/2005 |
| WO | WO 2006/077471 | 7/2006 |
| WO | WO 2006/085967 | 8/2006 |
| WO | WO 2006/105338 | 10/2006 |
| WO | WO 2007/110678 | 10/2007 |

OTHER PUBLICATIONS

Rudikoff et al Proc Natl Acad Sci USA 1982 vol. 79 pp. 1979-1983.*
MacCallum et al. Journal of Molecular. Biology, 1996, vol. 262, pp. 732-745.*
Pascalis et al. Journal of Immunology, 2002, vol. 169, pp. 3076-3084.*
Casset et al. Biochemical and Biophysical Research Communications, 2003, vol. 307, pp. 198-205.*
Vajdos et al. Journal of Molecular biology, 2002, vol. 320, pp. 415-428.*
Holm et al. Molecular Immunology, 2007, vol. 44, pp. 1075-1084.*
Chen et al. Journal of Molecular Biology, 1999, vol. 293, pp. 865-881.*
Wu et al. Journal of Molecular Biology, 1999, vol. 294, pp. 151-162.*
Lund et al. The Journal of Immunology 1996, 157:4963-4969.*
Chothia et al., "Conformations of Immunoglobulin Hypervariable Regions," Nature, vol. 342:877-883 (1989).
Dijstelbloem et al., "Inflammation in Autoimmunity: Receptors for IgC Revisited," Trends in Immunol., vol. 22: 510-516 (2001).
Edelman et al., "The Covalent Structure of an Entire γG Immunoglobulin Molecule," Biochemistry, vol. 63:78-85 (1969).
Gessner et al., "The IgG Fc Receptor Family," Ann. Hematol., vol. 76:231-248 (1998).
Johnson et al., "Activation of Mammalian Toll-like Receptors by Endogenous Agonists," Crit. Rev. Immunol., vol. 23(1-2):15-44 (2003).
Lehnardt et al., "Activation of Innate Immunity in the CNS Triggers Neurodegeneration Through a Toll-like Receptor 4-Dependent Pathway," Proc. Nat'l. Acad. Sci. USA, vol. 100:8514-8519 (2003).
Nimmerjahn et al., "FcγRIV: A Novel FcR with Distinct IgG Subclass Specificity," Immunity, vol. 23:41-51 (2005).
Ohashi et al., "Cutting Edge: Heat Shock Protein 60 Is a Putative Endogenous Ligand of the Toll-Like Receptor-4 Complex," J. Immunol., vol. 164:558-561 (2000).
Okamura et al., "The Extra Domain A of Fibronectin Activates Toll-like Receptor 4," J. Biol. Chem., vol. 276:10229-10233 (2001).
O'Neill, "Therapeutic Targeting of Toll-Like Receptors for Inflammatory and Infectious Diseases," Curr. Opin. Pharmacol., vol. 3:396-403 (2003).
Pandey & Agrawal, "Immunobiology of Toll-like Receptors: Emerging Trends," Immunol. Cell Biol., vol. 84:333-341 (2006).
Salmon et al., "Allelic Polymorphisms of Human Fcγ Receptor IIA and Fcγ Receptor IIIB: Independent Mechanisms for Differences in Human Phagocyte Function," J. Clin. Invest., vol. 89:1274-1281 (1992).
Shields et al., "High Resolution Mapping of the Binding Site on Human IgG1 for FcγRI, FcγRII, FcγRIII, and FcRn and Design of IgG1 Variants with Improved Binding to the FcγR," J. Biol. Chem., vol. 276:6591-6604 (2001).
Tax et al., "Polymorphism in Mitogenic Effect of IgG1 Monoclonal Antibodies Against T3 Antigen on Human T Cells," Nature, vol. 304:445-447 (1983).
van der Pol & van de Winkel, "IgG Receptor Polymorphisms: Risk Factors for Disease," Immunogenetics, vol. 48:222-232 (1998).

* cited by examiner

*Primary Examiner* — Chun Dahle

(74) *Attorney, Agent, or Firm* — Mintz Levin Cohn Ferris Glovsky and Popeo, P.C.; Ivor R. Elrifi

(57) ABSTRACT

Disclosed are processes for producing a variant polypeptide (e.g. antibodies) having modified binding characteristics for human Fc gamma receptor IIA (CD32A) leading to increased inhibition of proinflammatory mediators while retaining binding to a target antigen via its Fv portion, which processes comprise altering the polypeptides by substitution of at least two amino acid residues at EU position 325, 326 or 328 of a human IgG CH2 region for a sequence selected from SAAF, SKAF, NAAF and NKAF. Also disclosed are molecules, particularly polypeptides, more particularly immunoglobulins (e.g. antibodies) that include a variant CDR3 region, wherein the variant CDR3 region includes at least one amino acid modified relative to a wild-type CDR3 region. The polypeptides that can be generated according to the methods of the invention are highly variable, and they can include antibodies and fusion proteins that contain an Fc region or a biologically active portion thereof.

7 Claims, 18 Drawing Sheets

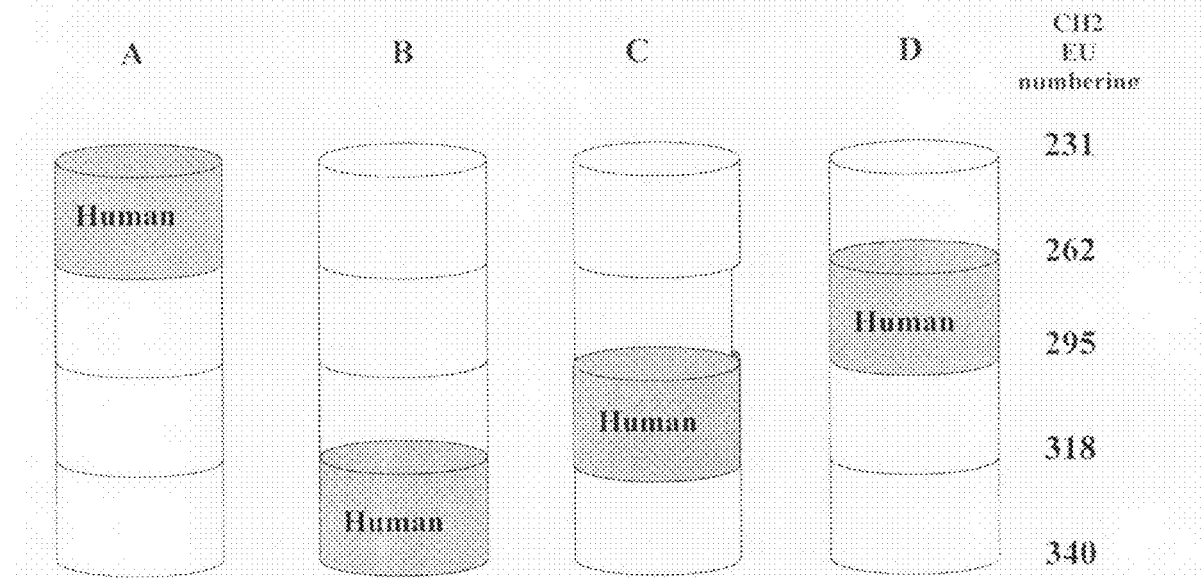
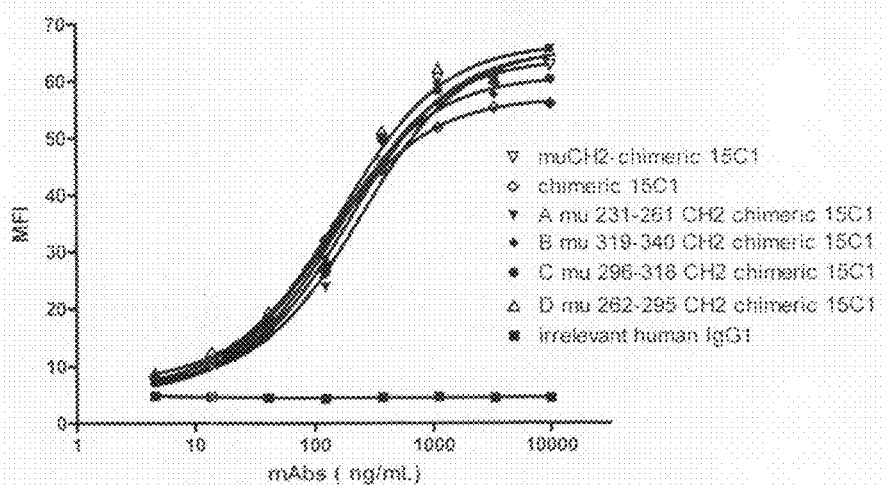

- ◇ Human isotype control
- ◆ A mu 231-261CH2 chimeric 15C1
- ■ B mu 319-340 CH2 chimeric 15C1
- ○ C mu 296-318 CH2 chimeric 15C1
- ▽ D mu 262-295 CH2 chimeric 15C1

Mu CH2 319-340 *Chimeric IgG1*

Figure 8A

```
              1  2 345 6             7
Mouse CH2  319 FKCRVNSAAFPAPIEKTISKTK 340 (SEQ ID NO: 90)
Human CH2  319 Y---K-SNK-L----------A- 340 (SEQ ID NO: 91)
```

Figure 8B

```
                   1  2 345 6             7
Mouse IgG1    319  FKCRVNSAAFPAPIEKTISKTK 340 (SEQ ID NO: 90)
A: T7A             --------------------A-     (SEQ ID NO: 92)
B: F1Y,R2K         Y--K----------------A-     (SEQ ID NO: 93)
C: N3S             Y--K-S--------------A-     (SEQ ID NO: 94)
D: F6L             Y--K-S---L----------A-     (SEQ ID NO: 95)
E: S4N             Y--K-SN--L----------A-     (SEQ ID NO: 96)
Human IgG1    319  Y--K-SNK-L----------A- 340 (SEQ ID NO: 91)
```

Figure 14A:
MD-2 nucleic acid sequence:

```
1    ggcgggccgc tcccacttcg gcacgagggg cacgaggtaa atcttttctg cttactgaaa
61   aggaagagtc tgatgattag ttactgatcc tctttgcatt tgtaaagctt tggagatatt
121  gaatcatgtt accatttctg ttttttttcca ccctgttttc ttccatattt actgaagctc
181  agaagcagta ttgggtctgc aactcatccg atgcaagtat ttcatacacc tactgtgata
241  aaatgcaata cccaatttca attaatgtta accctgtat agaattgaaa ggatccaaag
301  gattattgca catttttctac attccaagga gagatttaaa gcaattatat ttcaatctct
361  atataactgt caacaccatg aatcttccaa agcgcaaaga agttatttgc cgaggatctg
421  atgacgatta ctcttttgc agagctctga agggagagac tgtgaataca acaatatcat
481  tctccttcaa gggaataaaa ttttctaagg gaaaatacaa atgtgttgtt gaagctattt
541  ctgggagccc agaagaaatg ctcttttgct tggagtttgt catcctacac caacctaatt
601  caaattagaa taaattgagt attt (SEQ ID NO:41)
```

Figure 14B:
MD-2 amino acid sequence:

```
1    MLPFLFFSTL FSSIFTEAQK QYWVCNSSDA SISYTYCDKM QYPISINVNP CIELKGSKGL
61   LHIFYIPRRD LKQLYFNLYI TVNTMNLPKR KEVICRGSDD DYSFCRALKG ETVNTTISFS
121  FKGIKFSKGK YKCVVEAISG SPEEMLFCLE FVILHQPNSN (SEQ ID NO:42)
```

Figure 15:

TLR4 amino acid sequence:

```
1    mmsasrlagt lipamaflsc vrpeswepcv evvpnityqc melnfykipd nlpfstknld
61   lsfnplrhlg sysffsfpel qvldlsrcei qtiedgayqs lshlstlilt gnpiqslalg
121  afsglssslqk lvavetnlas lenfpighlk tlkelnvahn liqsfklpey fsnltnlehl
181  dlssnkiqsi yctdlrvlhq mpllnlsldl slnpmnfiqp gafkeirlhk ltlrnnfdsl
241  nvmktciqgl aglevhrlvl gefrnegnle kfdksalegl cnltieefrl ayldyylddi
301  idlfncltnv ssfslvsvti ervkdfsynf gwqhlelvnc kfgqfptlkl kslkrltfts
361  nkggnafsev dlpslefldl srnglsfkgc csqsdfgtts lkyldlsfng vitmssnflg
421  leqlehldfq hsnlkqmsef svflsrnlli yldishthtr vafngifngl sslevlkmag
481  nsfqenflpd iftelrnltf ldlsqcqleq lsptafnsls slqvlnmshn nffsldtfpy
541  kclnslqvld yslnhimtsk kqelqhfpss laflnltqnd factcehqsf lqwikdqrql
601  lvevermeca tpsdkqgmpv lslnitcqmn ktiigvsvls vlvvsvvavl vykfyfhlml
661  lagcikygrg eniydafviy ssqdedwvrn elvknleegv ppfqlclhyr dfipgvaiaa
721  niihegfhks rkvivvvsqh fiqsrwcife yeiaqtwqfl ssragiifiv lqkvektllr
781  qqvelyrlls rntyleweds vlgrhifwrr lrkalldgks wnpegtvgtg cnwqeatsi
          (SEQ ID NO:43)
```

Figure 16:

```
                                                                                                                                                    (SEQ ID NO)
Human IgG1    APELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK     (44)
Human IgG2    APP_VAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTK     (54)
Human IgG3    APELLGGPSVFLFPPKPKDTLMISRTPEVTCVVVDVSHEDPEVQFKWYVDGVEVHNAKTKPREEQYNSTFRVVSVLTVLHQDWLNGKEYKCKVSNKALPAPIEKTISKTK     (55)
Human IgG4    APEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAK     (56)
Mouse IgG1    VPEV___SSVFIFPPKPKDVLTITLTPKVTCVVVDISKDDPEVQFSWFVDDVEVHTAQTQPREEQFNSTFRSVSELPIMHQDWLNGKEFKCRVNSAAFPAPIEKTISKTK     (57)
Mouse IgG2ab  APDLLGGPSVFIFPPKIKDVLMISLSPMVTCVVVDVSEDDPDVQISWFVNNVEVHTAQTQTHREDYNSTLRVVSALPIQHQDWMSGKEFKCKVNNRALPSPIEKTISKPR     (58)
Mouse IgG2aa  APNLLGGPSVFIFPPKIKDVLMISLSPIVTCVVVDVSEDDPDVQISWFVNNVEVHTAQTQTHREDYNSTIRVVSALPIQHQDWMSGKEFKCKVNNKDLPAPIERTISKPK     (59)
Mouse IgG2b   APNLEGGPSVFIFPPNIKDVLMISLTPKVTCVVVDVSEDDPDVQVHVSWFVDKEVHTAWTQPREAQYNSTFRVVSALPIQHQDWMRGKEFKCKVNNKALPAPIERTISKPK     (60)
Mouse IgG3    AGNILGGPSVFIFPPKPKDALMISLTPKVTCVVVDVSEDDPDVHVSWFIDDVEVHTAQTHAPEKQSNSTLRSVSELPIVHRDWLNGKTFKCKVNSGAFPAPIEKSISKPE     (61)
Rat IgG1      GSEV___SSVFIFPPKPKTKDVLTITLTPKVTCVVVDISQNDPEVRFSWFSWFVDDPEVHFSWFVDDVEVHTAQTRPPEEQFNSTFRSVSELPILHQDWLNGRTFRCKVT SAAFPSPIEKTISKPE     (62)
Rat IgG2a     GSEV___SSVFIFPPKPKDVLTITLTPKVTCVVVDISQDDPEVHFSWFVDQFSWFVNNVEVHTAQTQPREEQYNSTFRVVSALPIQHQDWMSGKEFKCVNNKALPSPIEKTISKPE     (63)
Rat IgG2b     VPELLGGPSVFIFPPKPKDILLISQNAKVTCVVVDVSEEEPDVQFSWFVNNVEVHTAQTQPREEQYNSTFRVVSALPIQHQDWMSGKEFKCVNNKALPSPIEKTISKPK     (64)
Rat IgG2c     DDNL_GRPSVFIFPPKPKDILMITLTPKVTCVVVDVSEEEPDVQFSWFVDNVRVFTAQTQPHEEQLNGTFRVVSTLHIQHQDWMSGKEFKCVNNKDLPSPIEKTISKPR     (65)
              .    :***** ::**  :.   :*    **:*******     * .:*:* *::     :           .* .**    .: *    . ::.**  : ::**::***
```

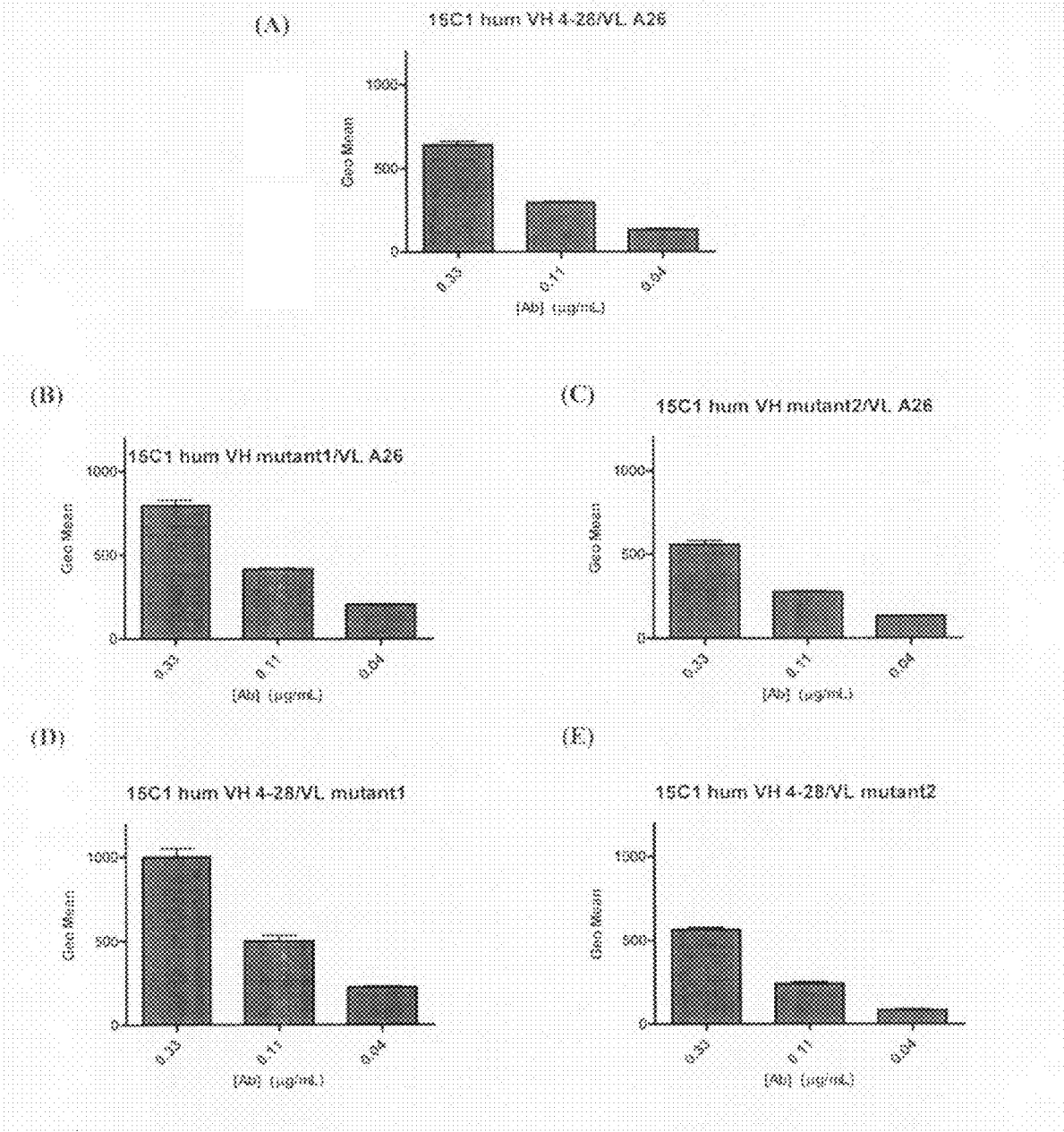

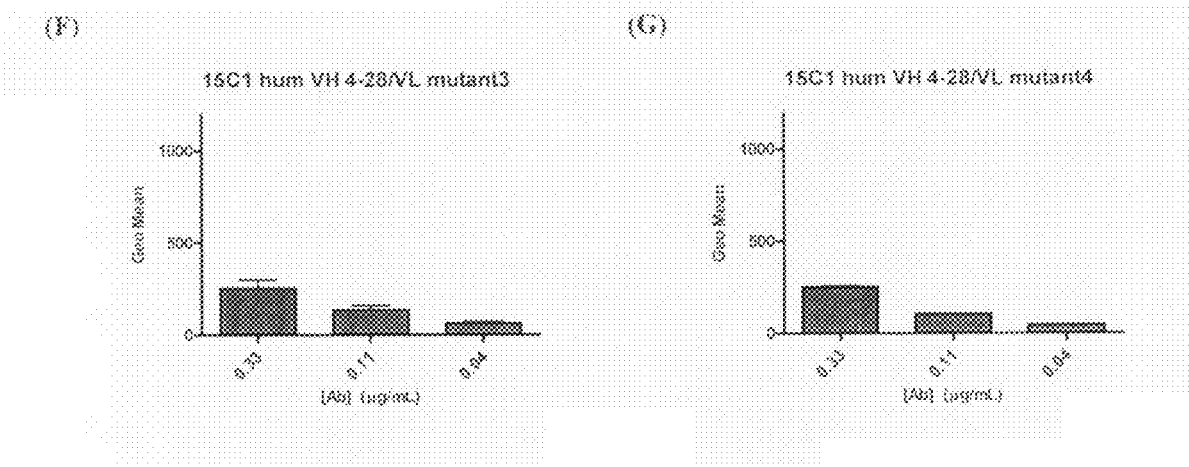

FC RECEPTOR-BINDING POLYPEPTIDES WITH MODIFIED EFFECTOR FUNCTIONS

RELATED APPLICATIONS

This patent application claims the benefit of U.S. Provisional Patent Application Ser. No. 60/930,276 filed May 14, 2007, the contents of which are herein incorporated by reference in their entirety.

FIELD OF THE INVENTION

This invention relates to molecules, particularly polypeptides, more particularly immunoglobulins (e.g. antibodies) that include a variant Fc region wherein said variant Fc region includes at least one amino acid modification relative to a wild-type Fc region, where variant Fc region has modified binding characteristics for human Fc gamma receptor IIA (CD32A) leading to prevention of proinflammatory mediators release (e.g. TNF-alpha, Interleukin (IL)-1, IL-6, IL-8 and chemokines). This invention also relates to molecules, particularly polypeptides, more particularly immunoglobulins (e.g. antibodies) that include a variant CDR3 region, wherein the variant CDR3 region includes at least one amino acid modified relative to a wild-type CDR3 region. This invention also generally relates to methods of producing such molecules, a process for modifying an effector function and methods of using such altered antibodies as therapeutic and diagnostic agents.

BACKGROUND OF THE INVENTION

Antibodies, or immunoglobulins, comprise two heavy chains linked together by disulphide bonds and two light chains, each light chain being linked to a respective heavy chain by disulphide bonds. The general structure of an antibody of class IgG (i.e. an immunoglobulin (Ig) of class gamma (G) is shown schematically in FIG. 1A.

Each heavy chain has at one end a variable domain followed by a number of constant domains. Each light chain has a variable domain at one end and a constant domain at its other end, the light chain variable domain being aligned with the variable domain of the heavy chain and the light chain constant domain being aligned with the first constant domain of the heavy chain.

Antigen binds to antibodies via an antigen binding site in the variable domains of each pair of light and heavy chains. Other molecules, known as effector molecules, bind to other sites in the remainder of the molecule, i.e. other than the antigen binding sites, and this portion of antibody will be referred to as "the constant portion" of an antibody, such sites being located particularly in the Fc region constituted by the portions of the heavy chains extending beyond the ends of the light chains.

The constant portion of antibodies specifically interact with receptors on "effector" cells. For example, the Fc region mediates effector functions that have been divided into two categories. In the first are the functions that occur independently of antigen binding; these functions due to the major histocompatibility complex class I-related receptor FcRn confer IgGs persistence in the circulation and the ability to be transferred across cellular barriers by transcytosis (see Ghetie V and Ward S). In the second are the functions that operate after an antibody binds an antigen; these functions involve the participation of the complement cascade or Fc receptor (FcR) bearing cells.

FcRs are defined by their specificity for immunoglobulin isotypes. For example Fc receptors for IgG antibodies are referred to as FcγR. FcRs are specialized cell surface receptors on hematopoietic cells that mediate both the removal of antibody-coated pathogens by phagocytosis of immune complexes, and the lysis of erythrocytes and various other cellular targets (e.g. tumor cells) coated with the corresponding antibody.

The FcγRs play a critical role in either abrogating or enhancing immune recruitment. Currently, three classes of FcγRs are distinguished on cells of the immune system: the high-affinity receptor Fc RI (CD64), capable of binding monomeric IgG; and the low-affinity receptors FcγRII (CD32), and FcγRIII (CD16), which interact preferentially with complexed IgG. Furthermore, the FcγRII and FcγRIII classes comprise both "A" and "B" forms (Gessner-J E et al. Ann Heamatol, 1998, The IgG Fc receptor family, 76: 231-248).

FcγRII proteins are 40 KDa integral membrane glycoproteins which bind only the complexed IgG due to a low affinity for monomeric Ig ($10^6$ M$^{-1}$). This receptor is the most widely expressed FcγR, present on all hematopoietic cells, including monocytes, macrophages, B cells, NK cells, neutrophils, mast cells, and platelets. Fc γRII has only two immunoglobulin-like regions in its immunoglobulin binding chain and hence a much lower affinity for IgG than FcγRI. There are three human FcγRII genes (FcγRII-A, FcγRII-B, FcγRII-C), all of which bind IgG in aggregates or immune complexes. The gene for the FcγRIIa receptor contains either G or A in codon 131, resulting in either arginine (CGT) or histidine (CAT), respectively, in the second extracellular domain. This change alters the ability of the receptor to bind IgG. Cells with FcγRIIA His-131, the A/A genotype, bind human IgG2 with considerably higher affinity than those with Arg at position 131; conversely, cells with Arg-131, the G/G genotype, bind murine IgG1 with considerably higher affinity than those with His at position 131 (Salmon et al., 1992, J. Clin. Invest. 89:1274-1281). Originally, studies using monocytes interaction with an anti-CD3 antibody of the murine IgG1 subclass as a trigger for T-cell proliferation classified individuals phenotypically as low responders of high responders (Tax et al., 1983, Nature: 304: 445-447). It is now known that high responder cells in this assay have the G/G or A/G genotype while low-responder cells have the A/A genotype. The FcγRIIa 131 R/R genotype is a risk factor for susceptibility to some infectious and autoimmune diseases (Van der Pol W. L. and Van de Winkel J. G. J, 1998, Immunogenetics 48:222-232).

Distinct differences within the cytoplasmic domains of FcγRII-A and FcγRII-B create two functionally heterogeneous responses to receptor ligation. The fundamental difference is that the A isoform initiates intracellular signaling leading to cell activation such as phagocytosis and respiratory burst, whereas the β isoform initiates inhibitory signal, e.g., inhibiting B-cell activation.

Monoclonal antibodies (mAbs) have now been used to treat disease in human patients. Although some mAbs may function effectively without utilizing antibody effector functions (e.g. neutralizing antibodies), in many cases it may be desirable to engineer the Fc portion of the antibody to recruit the immune system to elicit an immune response. There exists a need in the art to produce antibodies that include a variant Fc region having increased potency while retaining the ability to bind to a given target. Accordingly, there exists a need to produce altered IgG antibodies that elicit a modified Fc receptor activity while retaining binding to an antigen as compared to an unaltered antibody.

SUMMARY OF THE INVENTION

The altered polypeptides described herein include at least an FcγR binding portion of an Fc region of an immunoglobulin polypeptide. The altered antibodies of the invention also include an altered antibody having a variant CDR3 region in which at least one amino acid residue in the CDR3 region of the antibody has been modified. The altered antibodies and altered polypeptide of the invention also include polypeptides that include at least an FcγR binding portion of an Fc region of an immunoglobulin polypeptide and a variant CDR3 region. The altered antibodies and altered polypeptide of the invention also include polypeptides that include at least a variant Fc region of an immunoglobulin polypeptide and a variant CDR3 region.

The altered polypeptides described herein include antibodies that include at least one specific amino acid substitution within for example, an Fc region or an FcR binding fragment thereof (e.g., polypeptide having amino acid substitutions within an IgG constant domain) such that the modified antibody elicits alterations in antigen-dependent effector function while retaining binding to antigen as compared to an unaltered antibody. For example, the altered antibodies elicit the prevention of proinflammatory mediator release. In a preferred embodiment, the altered antibodies are human and of the IgG isotype. For example, the altered antibodies are human IgG1, IgG2, IgG3 or IgG4 isotype. The altered antibodies described herein have an increased potency as compared to an unaltered antibody.

The altered antibodies of the invention include an altered antibody in which at least one amino acid residue in the constant region of the Fc portion of the antibody has been modified. For example, at least one amino acid in the CH2 domain of the Fc portion has been replaced by a different residue, i.e., an amino acid substitution. In the altered antibodies described herein, one or more of the amino acid residues that correspond to residues 325, 326 and 328 is substituted with a different residue as compared to an unaltered antibody. The numbering of the residues in the gamma heavy chain is that of the EU index (see Edelman, G. M. et al., 1969; Kabat, E, A., T. T. Wu, H. M. Perry, K. S. Gottesman, and C. Foeller., 1991. *Sequences of Proteins of Immunological Interest*, 5$^{th}$ Ed. U.S. Dept. of Health and Human Services, Bethesda, Md., NIH Publication n. 91-3242).

These altered antibodies with a mutated Fc portion elicit modified effector functions, e.g., a modified Fc receptor activity, as compared to an unaltered antibody. For example, the human Fc receptor is CD32A. In some embodiments, the altered antibodies elicit increased inhibition of proinflammatory mediator release following ligation to CD32A as compared to an unaltered antibody. Thus, the altered antibodies described herein elicit a modified Fc receptor activity, such as increasing the inhibition of proinflammatory mediators release, while retaining the ability to bind a target antigen. In some embodiments, the altered antibody is a neutralizing antibody, wherein the altered antibody elicits a modified Fc receptor activity, while retaining the ability to neutralize one or more biological activities of a target antigen via Fv binding.

In embodiments where the altered antibody is a human IgG1 isotype, the altered antibodies include the amino acid substitution at EU amino acid position 328 alone or together with EU amino acid positions 325 and 326 of the mouse IgG1 gamma heavy chain constant region as compared to unaltered antibody. In one embodiment, EU amino acid position 328 of the gamma heavy chain constant region is substituted with a non-polar amino acid, such as alanine, cysteine, leucine, isoleucine, valine, glycine, phenylalanine, proline, tryptophan and tyrosine. Most preferably, EU amino acid position 328 of the gamma heavy chain constant region is substituted with phenylalanine. In one embodiment, EU amino acid position 325 of the gamma heavy chain constant region is substituted with a polar amino acid such as arginine, asparagine, glutamine, glutamic acid, histidine, lysine, serine or threonine. Most preferably, EU amino acid position 325 of the gamma heavy chain constant region is substituted with serine. In one embodiment, EU amino acid position 326 of the gamma heavy chain constant region is substituted with a non-polar amino acid, such as alanine, cysteine, leucine, isoleucine, valine, glycine, phenylalanine, proline, tryptophan and tyrosine. Most preferably, EU amino acid position 326 of the gamma heavy chain constant region is substituted with alanine. In some embodiments, the altered antibodies contain EU amino acid position 328 with one or two amino acid substitutions within the human IgG1 gamma heavy chain constant region, wherein the substitutions occur at one or two amino acid residues selected from EU amino acid positions 325 and 326. In one embodiment, the altered human IgG1 antibody contains amino acid substitutions at EU positions 326 and 328. For example, the residue 326 of the human IgG1 gamma heavy chain constant region is substituted with alanine and the residue 328 of the human IgG1 gamma heavy chain constant region is substituted with phenylalanine. In some embodiments, EU positions 325 to 328 of the gamma heavy chain constant region of the altered human IgG1 antibody consist of a sequence selected from SAAF (SEQ ID NO: 86), SKAF (SEQ ID NO: 87), NAAF (SEQ ID NO: 88) and NKAF (SEQ ID NO: 89).

In embodiments where the altered antibody is a human IgG2 isotype, the altered antibodies include the amino acid substitution at EU amino acid position 328 alone or together with EU amino acid positions 325 and 326 as compared to unaltered antibody. In one embodiment, EU amino acid position 328 of the gamma heavy chain constant region is substituted with a non-polar amino acid, such as alanine, cysteine, leucine, isoleucine, valine, glycine, phenylalanine, proline, tryptophan and tyrosine. Most preferably, EU amino acid position 328 of the gamma heavy chain constant region is substituted with phenylalanine. In one embodiment, EU amino acid position 325 of the gamma heavy chain constant region is substituted with a polar amino acid such as arginine, asparagine, glutamine, glutamic acid, histidine, lysine, serine or threonine. Most preferably, EU amino acid position 325 of the gamma heavy chain constant region is substituted with serine. In one embodiment, EU amino acid position 326 of the gamma heavy chain constant region is substituted with a non-polar amino acid, such as alanine, cysteine, leucine, isoleucine, valine, glycine, phenylalanine, proline, tryptophan and tyrosine. Most preferably, EU amino acid position 326 of the gamma heavy chain constant region is substituted with alanine. In some embodiments, the altered antibodies contain EU amino acid position 328 with one or two amino acid substitutions within the human IgG2 gamma heavy chain constant region, wherein the substitutions occur at one or two amino acid residues selected from EU amino acid positions 325 and 326. In one embodiment, the altered human IgG2 antibody contains amino acid substitutions at EU positions 326 and 328. For example, the residue 326 of the human IgG2 gamma heavy chain constant region is substituted with alanine and the residue 328 of the human IgG2 gamma heavy chain constant region is substituted with phenylalanine. In some embodiments, EU positions 325 to 328 of the gamma heavy chain constant region of the altered human IgG2 antibody consist of a sequence selected from SAAF (SEQ ID NO: 86), SKAF (SEQ ID NO: 87), NAAF (SEQ ID NO: 88) and NKAF (SEQ ID NO: 89).

In embodiments where the altered antibody is a human IgG3 isotype, the altered antibodies include the amino acid substitution at EU amino acid position 328 alone or together with EU amino acid positions 325 and 326 as compared to unaltered antibody. In one embodiment, EU amino acid position 328 of the gamma heavy chain constant region is substituted with a non-polar amino acid, such as alanine, cysteine, leucine, isoleucine, valine, glycine, phenylalanine, proline, tryptophan and tyrosine. Most preferably, EU amino acid position 328 of the gamma heavy chain constant region is substituted with phenylalanine. In one embodiment, EU amino acid position 325 of the gamma heavy chain constant region is substituted with a polar amino acid such as arginine, asparagine, glutamine, glutamic acid, histidine, lysine, serine or threonine. Most preferably, EU amino acid position 325 of the gamma heavy chain constant region is substituted with serine. In one embodiment, EU amino acid position 326 of the gamma heavy chain constant region is substituted with a non-polar amino acid, such as alanine, cysteine, leucine, isoleucine, valine, glycine, phenylalanine, proline, tryptophan and tyrosine. Most preferably, EU amino acid position 326 of the gamma heavy chain constant region is substituted with alanine. In some embodiments, the altered antibodies contain EU amino acid position 328 with one or two amino acid substitutions within the human IgG3 gamma heavy chain constant region, wherein the substitutions occur at one or two amino acid residues selected from EU amino acid positions 325 and 326. In one embodiment, the altered human IgG3 antibody contains amino acid substitutions at EU positions 326 and 328. For example, the residue 326 of the human IgG3 gamma heavy chain constant region is substituted with alanine and the residue 328 of the human IgG3 gamma heavy chain constant region is substituted with phenylalanine. In some embodiments, EU positions 325 to 328 of the gamma heavy chain constant region of the altered human IgG3 antibody consist of a sequence selected from SAAF (SEQ ID NO: 86), SKAF (SEQ ID NO: 87), NAAF (SEQ ID NO: 88) and NKAF (SEQ ID NO: 89).

In embodiments where the altered antibody is a human IgG4 isotype, the altered antibodies include the amino acid substitution at EU amino acid position 328 alone or together with EU amino acid positions 325 and 326 as compared to unaltered antibody. In one embodiment, EU amino acid position 328 of the gamma heavy chain constant region is substituted with a non-polar amino acid, such as alanine, cysteine, leucine, isoleucine, valine, glycine, phenylalanine, proline, tryptophan and tyrosine. Most preferably, EU amino acid position 328 of the gamma heavy chain constant region is substituted with phenylalanine. In one embodiment, EU amino acid position 325 of the gamma heavy chain constant region is substituted with a polar amino acid such as arginine, asparagine, glutamine, glutamic acid, histidine, lysine, serine or threonine. Most preferably, EU amino acid position 325 of the gamma heavy chain constant region is substituted with serine. In one embodiment, EU amino acid position 326 of the gamma heavy chain constant region is substituted with a non-polar amino acid, such as alanine, cysteine, leucine, isoleucine, valine, glycine, phenylalanine, proline, tryptophan and tyrosine. Most preferably, EU amino acid position 326 of the gamma heavy chain constant region is substituted with alanine. In some embodiments, the altered antibodies contain EU amino acid position 328 with one or two amino acid substitutions within the human IgG4 gamma heavy chain constant region, wherein the substitutions occur at one or two amino acid residues selected from EU amino acid positions 325 and 326. In one embodiment, the altered human IgG4 antibody contains amino acid substitutions at EU positions 326 and 328. For example, the residue 326 of the human IgG4 gamma heavy chain constant region is substituted with alanine and the residue 328 of the human IgG4 gamma heavy chain constant region is substituted with phenylalanine. In some embodiments, EU positions 325 to 328 of the gamma heavy chain constant region of the altered human IgG4 antibody consist of a sequence selected from SAAF (SEQ ID NO: 86), SKAF (SEQ ID NO: 87), NAAF (SEQ ID NO: 88) and NKAF (SEQ ID NO: 89).

The altered antibodies of the invention also include an altered antibody having a variant CDR3 region in which at least one amino acid residue in the CDR3 region of the antibody has been modified. The altered antibodies and altered polypeptide of the invention also include polypeptides that include at least an FcγR binding portion of an Fc region of an immunoglobulin polypeptide and a variant CDR3 region. The altered polypeptides described herein include antibodies that include a variant CDR3 region and at least one specific amino acid substitution within for example, an Fc region or an FcR binding fragment thereof (e.g., polypeptide having amino acid substitutions within an IgG constant domain) such that the modified antibody elicits alterations in antigen-dependent effector function while retaining binding to antigen as compared to an unaltered antibody.

The variant CDR3 regions include the variant VH CDR3 regions shown in Example 4: KDPSDAFPY (SEQ ID NO: 80) and KDPSEGFPY (SEQ ID NO: 81). The variant CDR3 regions include the variant VL CDR3 regions shown in Example 4: QNSHSFPLT (SEQ ID NO: 82); QQGHSFPLT (SEQ ID NO: 83); QNSSSFPLT (SEQ ID NO: 84); and QQSHSFPLT (SEQ ID NO: 85).

In some embodiments, the altered antibodies include both a variant Fc region and a variant CDR3 region. In some embodiments, the altered antibodies include both a variant Fc region shown in Example 3 and a variant CDR3 region shown in Example 4, e.g., SEQ ID NOs: 80-85. In some embodiments, the altered antibodies include both a variant CH2 domain in the Fc region and a variant CDR3 region. In some embodiments, the altered antibodies include both a variant CH2 domain in the Fc region shown in Example 3 and a variant CDR3 region shown in Example 4, e.g., SEQ ID NOs: 80-85. In some embodiments, the altered antibodies include both a variant CH2 domain in the Fc region that is mutated at one or more of the residues that correspond to residues 325, 326 and/or 328 (using the numbering of the residues in the gamma heavy chain as in the EU index, Edelman, et al.) and a variant CDR3 region. In some embodiments, the altered antibodies include both a variant CH2 domain in the Fc region that is mutated at one or more of the residues that correspond to residues 325, 326 and/or 328 (using the numbering of the residues in the gamma heavy chain as in the EU index, Edelman, et al.) shown in Example 3 and a variant CDR3 region shown in Example 4, e.g., SEQ ID NOs: 80-85.

The altered polypeptides and antibodies of the invention also include antibodies that include a heavy chain variable amino acid sequence that is at least 90%, 92%, 95%, 97%, 98%, 99% or more identical the amino acid sequence of SEQ ID NO: 2, 12, 22, 32, 45, 46, 49, 51, 52, 66, or 68, and/or a light chain variable amino acid that is at least 90%, 92%, 95%, 97%, 98%, 99% or more identical the amino acid sequence of SEQ ID NO: 7, 17, 27, 37, 47, 48, 50, 53, 71, 73, 75 or 77.

The altered polypeptides and antibodies of the invention also include polypeptides that include at least an FcγR binding portion of an Fc region of an immunoglobulin polypeptide, and include a heavy chain variable amino acid sequence that is at least 90%, 92%, 95%, 97%, 98%, 99% or more identical the amino acid sequence of SEQ ID NO: 2, 12, 22, 32, 45, 46, 49, 51, 52, 66, or 68, and/or a light chain variable amino acid that is at least 90%, 92%, 95%, 97%, 98%, 99% or more identical the amino acid sequence of SEQ ID. NO: 7, 17, 27, 37, 47, 48, 50, 53, 71, 73, 75 or 77. In some embodiments, the altered antibodies include both a variant CH2 domain in the Fc region shown in Example 3. In some embodiments, the altered antibodies include both a variant CH2 domain in the Fc region that is mutated at one or more of the residues that correspond to residues 325, 326 and/or 328 (using the numbering of the residues in the gamma heavy chain as in the EU index, Edelman, et al.).

The altered polypeptides and antibodies of the invention also include polypeptides and antibodies that include a variant Fc region, and include a heavy chain variable amino acid sequence that is at least 90%, 92%, 95%, 97%, 98%, 99% or more identical the amino acid sequence of SEQ ID NO: 2, 12, 22, 32, 45, 46, 49, 51, 52, 66, or 68, and/or a light chain variable amino acid that is at least 90%, 92%, 95%, 97%, 98%, 99% or more identical the amino acid sequence of SEQ ID NO: 7, 17, 27, 37, 47, 48, 50, 53, 71, 73, 75 or 77. In some embodiments, the altered antibodies include both a variant CH2 domain in the Fc region shown in Example 3. In some embodiments, the altered antibodies include both a variant CH2 domain in the Fc region that is mutated at one or more of the residues that correspond to residues 325, 326 and/or 328 (using the numbering of the residues in the gamma heavy chain as in the EU index, Edelman, et al.).

The altered polypeptides and antibodies of the invention also include polypeptides and antibodies that include a variant CH2 domain in the Fc region, and include a heavy chain variable amino acid sequence that is at least 90%, 92%, 95%, 97%, 98%, 99% or more identical the amino acid sequence of SEQ ID NO: 2, 12, 22, 32, 45, 46, 49, 51, 52, 66, or 68, and/or a light chain variable amino acid that is at least 90%, 92%, 95%, 97%, 98%, 99% or more identical the amino acid sequence of SEQ ID NO: 7, 17, 27, 37, 47, 48, 50, 53, 71, 73, 75 or 77. In some embodiments, the altered antibodies include both a variant CH2 domain in the Fc region shown in Example 3. In some embodiments, the altered antibodies include both a variant CH2 domain in the Fc region that is mutated at one or more of the residues that correspond to residues 325, 326 and/or 328 (using the numbering of the residues in the gamma heavy chain as in the EU index, Edelman, et al.).

The altered antibodies and polypeptides of the invention also include polypeptides and antibodies that include three heavy chain complementarity determining regions (CDRs) having an amino acid sequence at least 90%, 92%, 95%, 97%, 98%, 99% or more identical to each of: (i) a VH CDR1 sequence selected from the group consisting of SEQ ID NOs: 3, 13, 23, and 33; (ii) a VH CDR2 sequence selected from the group consisting of SEQ ID NOs: 4, 14, 24, and 34; (iii) a VH CDR3 sequence selected from the group consisting of SEQ ID NOs: 5, 15, 25, 35, 80 and 81; and/or a light chain with three CDR that include an amino acid sequence at least 90%, 92%, 95%, 97%, 98%, 99% or more identical to each of (iv) a VL CDR1 sequence selected from the group consisting of SEQ ID NOs: 8, 18, 28, and 38; (v) a VL CDR2 sequence selected from the group consisting of SEQ ID NOs: 9, 19, 29 and 39; and (vi) a VL CDR3 sequence selected from the group consisting of SEQ ID NOs: 10, 20, 30, 40 82, 83, 84 and 85.

The invention also provides methods of targeting human CD32A by a monoclonal antibody in which at least EU amino acid position 328 of the gamma heavy chain constant region together with one or two of the amino acid residues that correspond to EU positions 325 and 326 of the heavy gamma chain constant region are substituted with the corresponding EU amino acid residue of mouse IgG1 at the same position which is different from the corresponding amino acid residue in an unaltered antibody, such that the antibody elicits increased inhibition of proinflammatory mediators release upon binding to human CD32A while retaining binding to antigen as compared to an unaltered antibody. In some embodiments, the altered antibody further includes a variant VH CDR3 regions shown in Example 4: KDPSDAFPY (SEQ ID NO: 80) and KDPSEGFPY (SEQ ID NO: 81) and/or a variant CDR3 region shown in Example 4: QNSHSFPLT (SEQ ID NO: 82); QQGHSFPLT (SEQ ID NO: 83); QNSSFPLT (SEQ ID NO: 84); and QQSHSFPLT (SEQ ID NO: 85).

In some embodiments, the amino acid residue that corresponds to EU position 325 of the gamma heavy chain constant region is substituted with serine. In some embodiments, the amino acid residue that corresponds to EU position 326 of gamma heavy chain constant region is substituted with alanine. In some embodiments, the amino acid residue that corresponds to EU position 328 of the gamma heavy chain constant region is substituted with phenylalanine. In some embodiments, the altered antibody further includes a variant VH CDR3 regions shown in Example 4: KDPSDAFPY (SEQ ID NO: 80) and KDPSEGFPY (SEQ ID NO: 81) and/or a variant CDR3 region shown in Example 4: QNSHSFPLT (SEQ ID NO: 82); QQGHSFPLT (SEQ ID NO: 83); QNSSFPLT (SEQ ID NO: 84); and QQSHSFPLT (SEQ ID NO: 85).

In some embodiments, the altered antibody binds to a target selected from a toll-like receptor (TLR), MD2 accessory protein and CD14. For example, the altered antibody binds to soluble TLR4, the TLR4/MD2 complex, or both soluble TLR4 and the TLR4/MD2 complex. In some embodiments, the altered antibody binds to TLR2. For example, the antibodies are capable of blocking, e.g., neutralizing, LPS-induced pro-inflammatory cytokine production.

In some embodiments, the altered antibody is a human IgG1 isotype antibody that includes at least modification of amino acid residue at EU position 328 possibly with at east one amino acid residue of the gamma heavy chain constant region selected from amino acid residues 325 and 326 wherein the altered antibody elicits a modified Fc effector activity upon binding to human CD32A while retaining binding to antigen as compared to an unaltered antibody, and wherein the antibody includes (a) a $V_H$ CDR1 region comprising the amino acid sequence of SEQ ID NO: 3, 13, 23 or 33; (b) a $V_H$ CDR2 region comprising the amino acid sequence of SEQ ID NO: 4, 14, 24 or 34; (c) a $V_H$ CDR3 region comprising the amino acid sequence of SEQ ID NO: 5, 15, 25, 35, 80 or 81; (d) a $V_L$ CDR1 region comprising the amino acid sequence of SEQ ID NO: 8, 18, 28 or 38; (e) a $V_L$ CDR2 region comprising the amino acid sequence of SEQ ID NO: 9, 19, 29 or 39; and (f) a $V_L$ CDR3 region comprising the amino acid sequence of SEQ ID NO: 10, 20, 30, 40, 82, 83, 84, or 85, wherein the antibody binds soluble TLR4, MD2, the TLR4/MD2 complex or both soluble TLR4 and the TLR4/MD2 complex. In one embodiment, EU position 325 of the gamma heavy chain constant region is substituted with serine. In one embodiment, EU position 326 of the gamma heavy chain constant region is substituted with alanine. In one embodiment, EU position 328 of the gamma heavy chain constant region is substituted with phenylalanine.

In some embodiments, the altered antibodies include a gamma heavy chain constant region having two or more substitutions with an amino acid residue that is different from the corresponding amino acid residue in an unaltered antibody, wherein the substitutions occur at EU position 328 and one or two amino acid residues selected from residues 325 and 326 of the gamma heavy chain constant region. In one embodiment, the substitutions are at residues 326 and 328. For example, EU position 326 of the heavy chain constant region is substituted with alanine, and EU position 328 of the heavy chain constant region is substituted with phenylalanine. In some embodiments, the altered antibodies contain a heavy chain constant region in which EU position 325-328 of the gamma heavy chain constant region consist of a sequence selected from SAAF (SEQ ID NO: 86), SKAF (SEQ ID NO: 87), NAAF (SEQ ID NO: 88) and NKAF (SEQ ID NO: 89). In one embodiment, the $V_H$ CDR1 region of the altered human IgG1 antibody includes the amino acid sequence of SEQ ID NO: 23, the $V_H$ CDR2 region includes the amino acid sequence of SEQ ID NO: 24, the $V_H$ CDR3 region includes the amino acid sequence of SEQ ID NO: 25 or SEQ ID NO: 80 or SEQ ID NO: 81, the $V_L$ CDR1 region includes the amino acid sequence of SEQ ID NO: 28, the $V_L$ CDR2 region includes the amino acid sequence of SEQ ID NO: 29, and the $V_L$ CDR3 region includes the amino acid sequence of SEQ ID NO: 30, SEQ ID NO: 82, SEQ ID NO: 83, SEQ ID NO: 84 or SEQ ID NO:85.

In some embodiments, the altered antibodies are altered versions of the antibodies referred to herein as 16G7, mu16G7, 7E3, mu7E3, 15C1, mu15C1, 18H10 and mu18H10. Modified versions of these antibodies, which recognize the TLR4/MD2 complex, elicit a modified, e.g., inhibitory human CD32A activity and inhibit LPS-induced pro-inflammatory cytokine production at least two-fold, five-fold, 10-fold, 20-fold, 50-fold, 75-fold, or 100-fold more than the commercially available, anti-TLR4 non-blocking monoclonal antibody HTA125.

In some embodiments, the altered antibodies are modified versions of antibodies that recognize CD14, such as the anti-CD14 monoclonal antibody known as 28C5 (see e.g., U.S. Pat. No. 6,444,206, hereby incorporated by reference in its entirety), and altered versions of antibodies that recognize TLR2, including, e.g., the anti-TLR2 monoclonal antibody known as T2.5 (see e.g., WO 2005/028509, hereby incorporated by reference in its entirety).

The invention also provides isolated polypeptides that include a gamma 1 Fc (γ1Fc) region, wherein amino acid residues at EU positions 325-328 of the region consist of an amino acid motif selected from SAAF (SEQ ID NO: 86), SKAF (SEQ ID NO: 87), NAAF (SEQ ID NO: 88) and NKAF (SEQ ID NO: 89).

The altered antibodies of the invention are produced using any suitable technique including techniques that are well known to those skilled in the art. For example, the altered antibodies are produced by modifying known antibodies to include at least one mutation in the Fc region, particularly in the CH2 domain, and more particularly at a location selected from EU positions 325, 326 and 328. The numbering of the residues in the gamma heavy chain is that of the EU index (see Edelman, G. M. et al., 1969; Kabat, E, A., T. T. Wu, H. M. Perry, K. S. Gottesman, and C. Foeller., 1991. *Sequences of Proteins of Immunological Interest*, 5th Ed. U.S. Dept. of Health and Human Services, Bethesda, Md., NIH Publication n. 91-3242). The numbering for the immunoglobulin variable regions for the antibodies described herein is as defined by E. A. Kabat et al., 1991. (Kabat, E, A., T. T. Wu, H. M. Perry, K. S. Gottesman, and C. Foeller., 1991. *Sequences of Proteins of Immunological Interest*, 5th Ed. U.S. Dept. of Health and Human Services, Bethesda, Md., NIH Publication n. 91-3242).

Pharmaceutical compositions according to the invention can include an altered antibody of the invention and a carrier. The altered antibodies can equally be of murine, human and rat origin given the high sequence homology between the different immunoglobulins. The composition can include a single isotype class, e.g., an IgG1 isotype altered antibody, or any combination of rat, mouse and human IgG isotype classes, e.g., IgG1, IgG2, IgG2a, IgG2b, IgG2c, IgG3, IgG4 and combinations thereof. These pharmaceutical compositions can be included in kits, such as, for example, diagnostic kits.

BRIEF DESCRIPTION OF THE DRAWINGS

FIG. 6A is a schematic representation of four mouse CH2 mutants (A, B, C and D) each containing the homologous corresponding human IgG1 CH2 sub-region; residues 231-262, 318-340, 295-318 and 262-295 for mutants A, B, C and D, respectively.

FIG. 6B is a graph depicting binding to CHO stable cell line expressing human TLR4-MD2 complex on their surface.

FIG. 8A is an illustration depicting an alignment of deduced amino-acid sequences of the mouse IgG1 C-terminal end (residue 319 to 340) of the heavy chain CH2 domain with human IgG1 C-terminal end (residue 319 to 340) of the heavy chain CH2 domain. Dashes indicate amino acids identical with those in the mouse sequence. Sequences were aligned on the basis of maximum nucleic acid alignment according to EU numbering.

FIG. 8B is an illustration depicting an alignment of deduced amino-acid sequences of the mouse IgG1 C-terminal end (residue 319 to 340) of the heavy chain CH2 domain with the 5 mutants (A to E) and human IgG1 C-terminal end (residue 319 to 340) of the heavy chain CH2 domain. Dashes indicate amino acids identical with those in the mouse sequence. Sequences were aligned on the basis of maximum nucleic acid alignment according to EU numbering. Mutations are denoted by the mouse amino acid residue followed by a number from 1 to 7 corresponding to the seven differences between the mouse and human sequences and finally the human amino acid it has been mutated to.

FIG. 14A is an illustration depicting a nucleic acid sequence encoding the accessory protein MD-2 (SEQ ID NO:41).

FIG. 14B is an illustration depicting an amino acid sequence of a mature MD-2 accessory protein (SEQ ID NO:42).

FIG. 15 is an illustration depicting the amino acid sequence of human toll-like receptor 4 (TLR4) (SEQ ID NO:43).

FIG. 16 is an illustration depicting the protein display of the CH2 domain of human, mouse and rat IgG isotypes. "*" means that the residues in that column are identical in all sequences in the alignment.

FIGS. 17A-17G are a series of graphs depicting the analysis of 15C1 humanized mutants by flow cytometry on cells expressing recombinant human TLR4-MD2.

DETAILED DESCRIPTION OF THE INVENTION

Figure 1A:
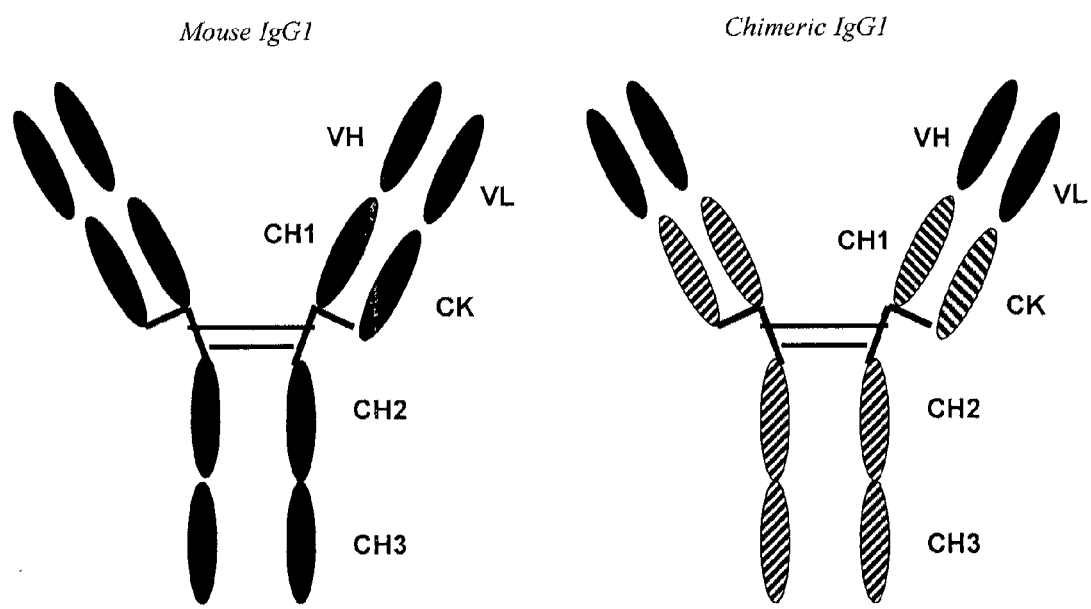
FIG. 1A is a schematic representation of mouse and chimeric IgG1 15C1 antibodies. The mouse variable and constant domains of the light and heavy chain are in solid black. The human constant domains of light and heavy chains are in hatched black. Mouse IgG1 15C1 is a mouse immunoglobulin of the IgG1 subclass specific for human TLR4. Chimeric IgG1 15C1 is a recombinant immunoglobulin consisting of the mouse heavy and light chain variable regions of 15C1 in fusion with human IgG1 heavy and Kappa light constant regions. V=variable domain; L=light chain; H=heavy chain; CK=Kappa constant domain of the light chain; CH1, CH2, CH3=constant domains of the heavy chain.

The altered antibodies described herein are antibodies that include at least one specific amino acid substitution in the gamma heavy chain constant region such that the altered antibody elicits alterations in antigen-dependent effector function while retaining binding to antigen as compared to an unaltered antibody. In a preferred embodiment, the altered antibodies are human. For example, the altered antibodies are IgG1, IgG2, IgG3 or IgG4 isotype.

The altered antibodies of the invention also include an altered antibody having a variant CDR3 region in which at least one amino acid residue in the CDR3 region of the antibody has been modified. The altered antibodies and altered polypeptide of the invention also include polypeptides that include at least an FcγR binding portion of an Fc region of an immunoglobulin polypeptide and a variant CDR3 region. The altered antibodies and altered polypeptide of the invention also include polypeptides that include at least a variant Fc region of an immunoglobulin polypeptide and a variant CDR3 region. The variant CDR3 regions include the variant VH CDR3 regions shown in Example 4: KDPSDAFPY (SEQ ID NO: 80) and KDPSEGFPY (SEQ ID NO: 81). The variant CDR3 regions include the variant VL CDR3 regions shown in Example 4: QNSHSFPLT (SEQ ID NO: 82); QQGHSFPLT (SEQ ID NO: 83); QNSSSFPLT (SEQ ID NO: 84); and QQSHSFPLT (SEQ ID NO: 85).

The altered antibodies of the invention include an altered antibody in which at least the amino acid residue at EU position 328 in the CH2 domain of the Fc portion of the antibody has been modified. For example, at least the amino acid residue at EU position 328 has been substituted with phenylalanine. In the altered antibodies described herein, at least the amino acid residue at EU position 328 alone or together with EU amino acid positions 325 and 326 are substituted with a different residue as compared to an unaltered antibody.

These altered antibodies with a modified Fc portion elicit modified effector functions e.g., a modified Fc receptor activity, as compared to an unaltered antibody. For example, the human Fc receptor is CD32A. In some embodiments, the altered antibodies elicit a prevention of proinflammatory mediators release following ligation to CD32A as compared to an unaltered antibody. Thus, the altered antibodies described herein elicit a modified Fc receptor activity, such as the prevention of proinflammatory mediators release while retaining the ability to bind a target antigen. In some embodiments, the altered antibody is a neutralizing antibody, wherein the altered antibody elicits a modified Fc receptor activity, while retaining the ability to neutralize one or more biological activities of a target antigen.

For example, altered antibodies of the invention include monoclonal antibodies that bind the human TLR4/MD-2 receptor complex. This receptor complex is activated by lipopolysaccharide (LPS), the major component of the outer membrane of gram-negative bacteria. The altered antibodies of the invention inhibit receptor activation and subsequent intracellular signaling via LPS. Thus, the altered antibodies neutralize the activation of the TLR4/MD-2 receptor complex. In particular, the invention provides altered antibodies that recognize the TLR4/MD-2 receptor complex expressed on the cell surface. These altered antibodies block LPS-induced IL-8 production. In addition, some altered antibodies of the invention also recognize TLR4 when not complexed with MD-2. The altered antibody is, e.g., a humanized antibody.

Antibodies of the invention include antibodies that bind the human TLR4/MD-2 receptor complex and also bind TLR4 independently of the presence of MD-2. Antibodies of the invention also include antibodies that bind the TLR4 portion of the human TLR4/MD-2 receptor complex but binding is dependent on the presence of MD-2, but binding is greatly enhanced by the presence of MD-2, which suggests that the presence of the MD-2 causes a conformational change in TLR4, thereby exposing an epitope bound by the antibody. In addition, antibodies of the invention include antibodies that bind the human TLR4/MD-2 receptor complex and also bind MD-2 in the presence of TLR4.

Altered antibodies of the invention also include antibodies that recognize targets such as any toll-like receptor. Toll receptors, first discovered in *Drosophila*, are type I transmembrane protein having leucine-rich repeats (LRRs) in the extracellular portion of the protein, and one or two cysteine-rich domains. The mammalian homologs of the *Drosophila* Toll receptors are known as “Toll-like receptors” (TLRs). TLRs play a role in innate immunity by recognizing microbial particles and activating immune cells against the source of these microbial particles.

Currently, eleven types of Toll-like receptors have been identified in humans, TLRs 1-11 (Pandey S and Agrawal D K, Immunobiology of Toll-like-receptors: emerging trends. Immunol. Cell Biol., 2006; 84:333-341). These TLRs are characterized by the homology of their intracellular domains to that of the IL-1 receptor, and by the presence of extracellular leucine-rich repeats. The different types of TLRs are activated by different types of microbial particles. For example, TLR4 is primarily activated by lipopolysaccharide (LPS), while TLR2 is activated by lipoteichoic (LTA), lipoarabinomannan (LAM); lipoprotein (BLP), and peptideglycans (PGN). Toll receptor homologs, such as RP105, have also been identified.

For example, altered antibodies of the invention include antibodies that recognize TLR2, including, e.g., one or more modified versions of the anti-TLR2 monoclonal antibody known as T2.5 (see e.g., WO 2005/028509, hereby incorporated by reference in its entirety).

Other suitable altered antibodies include antibodies that recognize CD14, such as one or more modified versions of the anti-CD14 monoclonal antibody known as 28C5 (see e.g., U.S. Pat. No. 6,444,206, hereby incorporated by reference in its entirety).

DEFINITIONS

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer’s specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term “antibody” refers to immunoglobulin molecules and immunologically active portions of immunoglobulin (Ig) molecules, i.e., molecules that contain an antigen binding site that specifically binds (immunoreacts with) an antigen. By “specifically bind” or “immunoreacts with” or “immunospecifically bind” is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, dAb (domain antibody), single chain, $F_{ab}$, $F_{ab'}$ and $F_{(ab')2}$ fragments, scFvs, and an $F_{ab}$ expression library.

The basic antibody structural unit is known to comprise a tetramer. Each tetramer is composed of two identical pairs of polypeptide chains, each pair having one “light” (about 25 kDa) and one “heavy” chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is $\leq 1$ µM; e.g., $\leq 100$ nM, preferably $\leq 10$ nM and more preferably $\leq 1$ nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to its target, when the equilibrium binding constant ($K_d$) is $\leq 1$ µM, e.g., $\leq 100$ nM, preferably $\leq 10$ nM, and more preferably $\leq 1$ nM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the invention include the nucleic acid molecules encoding the heavy chain immunoglobulin molecules, and nucleic acid molecules encoding the light chain immunoglobulin molecules described herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules, and the light chain immunoglobulin molecules described herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxynucleotides or a modified form of either type of nucleotide. The term includes single and double stranded forms of DNA.

As used herein, the twenty conventional amino acids and their abbreviations follow conventional usage. See Immunology—A Synthesis (2nd Edition, E. S. Golub and D. R. Gren, Eds., Sinauer Associates, Sunderland Mass. (1991)). Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient includes human and veterinary subjects.

Antibodies

The altered antibodies described herein are antibodies that include at least one specific amino acid substitution in the gamma heavy chain constant region such that the altered antibody elicits alterations in antigen-dependent effector function while retaining binding to antigen as compared to an unaltered antibody. In a preferred embodiment, the altered antibodies are human. For example, the altered antibodies are IgG1, IgG2, IgG3 or IgG4 isotype.

The altered antibodies of the invention also include an altered antibody having a variant CDR3 region in which at least one amino acid residue in the CDR3 region of the antibody has been modified. The altered antibodies and altered polypeptide of the invention also include polypeptides that include at least an FcγR binding portion of an Fc region of an immunoglobulin polypeptide and a variant CDR3 region. The altered antibodies and altered polypeptide of the invention also include polypeptides that include at least a variant Fc region of an immunoglobulin polypeptide and a variant CDR3 region. The variant CDR3 regions include the variant VH CDR3 regions shown in Example 4: KDPSDAFPY (SEQ ID NO: 80) and KDPSEGFPY (SEQ ID NO: 81). The variant CDR3 regions include the variant VL CDR3 regions shown in Example 4: QNSHSFPLT (SEQ ID NO: 82); QQGHSFPLT (SEQ ID NO: 83); QNSSSFPLT (SEQ ID NO: 84); and QQSHSFPLT (SEQ ID NO: 85).

In one embodiment, altered antibodies that recognize TLR4, MD2 and/or the TLR4/MD2 complex have the ability to inhibit LPS-induced proinflammatory cytokine production. This inhibition is achieved via a cross-talk mechanism between the Fv portion of the altered antibody binding to its target antigen while its modified Fc portion is engaging with human CD32A. Inhibition is determined, for example, in the human whole blood and huTLR4/MD2 transfected HEK 293 cellular assays described herein. In this embodiment, the altered antibody is, for example a modified version of the monoclonal antibodies referred to herein as "mu18H10", "hu18H10", "mu16G7", "mu15C1", "hu15C1", "mu7E3" and "hu7E3". The mu18H10 and hu18H10 antibodies recognize the TLR4/MD-2 complex, but do not recognize an MD-2 protein when not complexed with TLR4. The mu16G7, mu15C1, hu15C1, mu7E3 and hu7E3 monoclonal antibodies recognize the TLR4/MD-2 complex. mu15C1, hu15C1 and 16G7 also recognize TLR4 when not complexed with MD-2.

Also included in the invention are antibodies that bind to the same epitope as the altered antibodies described herein. For example, altered antibodies of the invention specifically bind a TLR4/MD-2 complex, wherein the antibody binds to an epitope that includes one or more amino acid residues on human TLR4 between residues 289 and 375 of the amino acid sequence shown in FIG. 15. In another example altered antibodies that specifically bind the TLR4/MD2 complex, wherein the antibody binds to an epitope on human MD-2 between residues 19 and 57 of the amino acid sequence shown in FIG. 14B. Those skilled in the art will recognize that it is possible to determine, without undue experimentation, if a monoclonal antibody has the same specificity as a altered antibody of the invention by ascertaining whether the former prevents the latter from binding to the target (e.g., TLR2, CD14, TLR4/MD-2 complex or to TLR4 when not complexed to MD-2). If the monoclonal antibody being tested competes with the altered antibody of the invention, as shown by a decrease in binding by the altered antibody of the invention, then the two antibodies bind to the same, or a closely related, epitope. An alternative method for determining whether a monoclonal antibody has the specificity of a altered antibody of the invention is to pre-incubate the altered antibody of the invention with the target with which it is normally reactive, and then add the monoclonal antibody being tested to determine if the monoclonal antibody being tested is inhibited in its ability to bind the target. If the monoclonal antibody being tested is inhibited then, in all likelihood, it has the same, or functionally equivalent, epitopic specificity as the monoclonal antibody of the invention.

Various procedures known within the art may be used for the production of polyclonal or monoclonal antibodies directed against a given target, such as, for example, a toll-like receptor, the TLR4/MD-2 complex, or TLR4 when not complexed to MD-2, TLR2, CD14, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference).

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

Preferably, the altered antibodies of the invention are monoclonal antibodies. Altered antibodies are generated, e.g., by immunizing BALB/c mice with combinations of cell transfectants expressing high levels of a given target on their surface. Hybridomas resulting from myeloma/B cell fusions are then screened for reactivity to the selected target.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Monoclonal antibodies of the invention include humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', $F(ab')_2$ or other antigen-binding subsequences of antibodies) that are principally comprised of the sequence of a human immunoglobulin, and contain minimal sequence derived from a non-human immunoglobulin. Humanization is performed, e.g., by following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies also comprise, .e.g., residues which are found neither in the recipient antibody nor in the imported CDR or framework sequences. In general, the humanized antibody includes substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also includes at least a portion of an immunoglobulin constant region (Fc), typically that of a human immunoglobulin (Jones et al., 1986; Riechmann et al., 1988; and Presta, Curr. Op. Struct. Biol., 2:593-596 (1992)).

Fully human antibodies are antibody molecules in which the entire sequence of both the light chain and the heavy chain, including the CDRs, arise from human genes. Such antibodies are termed "human antibodies", or "fully human antibodies" herein. Monoclonal antibodies can be prepared by using trioma technique; the human B-cell hybridoma technique (see Kozbor, et al., 1983 Immunol Today 4: 72); and the EBV hybridoma technique to produce monoclonal antibodies (see Cole, et al., 1985 In: MONOCLONAL ANTIBODIES AND CANCER THERAPY, Alan R. Liss, Inc., pp. 77-96). Monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. An example of such a nonhuman animal is a mouse termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds specifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA. gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as *orthopox* or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci. USA 87:1149 (1990), Adenovirus Vectors (see LeGal LaSalle et al., Science, 259:988 (1993); Davidson, et al., Nat. Genet. 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icy) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266: 292-305 (1994)). Other methods that can be used include catheters, intravenous, parenteral, intraperitoneal and subcutaneous injection, and oral or other known routes of administration.

Bispecific antibodies are antibodies that have binding specificities for at least two different antigens. In the present case, one of the binding specificities is for a target such as TLR4, MD2, TLR4/MD2 complex, TLR2, CD14 or any toll-like receptor. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface includes at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating diseases and disorders associated with aberrant LPS signaling. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238: 1098 (1987).

Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS(N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Altered Antibodies

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2): 210-8 (2000), Wang W. "Lyophilization and development of solid protein pharmaceuticals." Int. J. Pharm. 203(1-2):1-60

(2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include a altered antibody of the invention are used to treat or alleviate a symptom associated with an immune-related disorder. The present invention also provides methods of treating or alleviating a symptom associated with an immune-related disorder. A therapeutic regimen is carried out by identifying a subject, e.g., a human patient suffering from (or at risk of developing) an immune-related disorder, using standard methods. For example, altered antibodies of the invention are useful therapeutic tools in the treatment of autoimmune diseases and/or inflammatory disorders. In certain embodiments, the use of altered antibodies that modulate, e.g., inhibit, neutralize, or interfere with, TLR signaling is contemplated for treating autoimmune diseases and/or inflammatory disorders.

Autoimmune diseases include, for example, Acquired Immunodeficiency Syndrome (AIDS, which is a viral disease with an autoimmune component), alopecia greata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barré syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Ménière's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjögren's syndrome, stiff-man syndrome, systemic lupus erythematosus, Takayasu arteritis, temporal arteritis/giant cell arteritis, ulcerative colitis, uveitis, vitiligo and Wegener's granulomatosis.

Inflammatory disorders include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

For example, altered antibodies are useful in the treatment of acute inflammation and sepsis induced by microbial products (e.g., LPS) and exacerbations arising from this acute inflammation, such as, for example, chronic obstructive pulmonary disease and asthma (see O'Neill, Curr. Opin. Pharmacol. 3: 396-403 (2003), hereby incorporated by reference in its entirety). Such antibodies are also useful in treating neurodegenerative autoimmune diseases. (Lehnardt et al., Proc. Natl. Acad. Sci. USA 100: 8514-8519 (2003), hereby incorporated by reference in its entirety).

In addition, the antibodies of the invention are also useful as therapeutic reagents in the treatment of diseases, such as, for example, osteoarthritis, which are caused by mechanical stress, which, in turn, induces endogenous soluble "stress" factors that trigger TLR4. Endogenous soluble stress factor include e.g., Hsp60 (see Ohashi et al., J. Immunol. 164: 558-561 (2000)) and fibronectin (see Okamura et al., J. Biol. Chem. 276: 10229-10233 (2001) and heparin sulphate, hyaluronan, gp96, β-Defensin-2 or surfactant protein A (see e.g., Johnson et al., Crit. Rev. Immunol., 23(1-2):15-44 (2003), each of which is hereby incorporated by reference in its entirety). The antibodies of the invention are also useful in the treatment of a variety of disorders associated with mechanical stress, such as for example, mechanical stress that is associated with subjects and patients placed on respirators, ventilators and other respiratory-assist devices. For example, the antibodies of the invention are useful in the treatment of ventilator-induced lung injury ("VILI"), also referred to as ventilation-associated lung injury ("VALI").

Other disease areas in which inhibiting TLR4 function could be beneficial include, for example, chronic inflammation (e.g., chronic inflammation associated with allergic conditions and asthma), autoimmune diseases (e.g., inflammatory bowel disorder) and atherosclerosis (see O'Neill, Curr. Opin. Pharmacol. 3: 396-403 (2003), hereby incorporated by reference in its entirety).

Symptoms associated with these immune-related disorders include, for example, inflammation, fever, general malaise, fever, pain, often localized to the inflamed area, rapid pulse rate, joint pain or aches (arthralgia), rapid breathing or other abnormal breathing patterns, chills, confusion, disorientation, agitation, dizziness, cough, dyspnea, pulmonary infections, cardiac failure, respiratory failure, edema, weight gain, mucopurulent relapses, cachexia, wheezing, headache, and abdominal symptoms such as, for example, abdominal pain, diarrhea or constipation.

Efficaciousness of treatment is determined in association with any known method for diagnosing or treating the particular immune-related disorder. Alleviation of one or more symptoms of the immune-related disorder indicates that the antibody confers a clinical benefit.

Methods for the screening of antibodies that possess the desired specificity include, but are not limited to, enzyme linked immunosorbent assay (ELISA) and other immunologically mediated techniques known within the art.

Antibodies directed against a target such as TLR2, CD14, TLR4, MD2, the TLR4/MD-2 complex or any toll-like receptor (or a fragment thereof) may be used in methods known within the art relating to the localization and/or quantitation of these targets, e.g., for use in measuring levels of these targets within appropriate physiological samples, for use in diagnostic methods, for use in imaging the protein, and the like). In a given embodiment, antibodies specific any of these targets, or derivative, fragment, analog or homolog thereof, that contain the antibody derived antigen binding domain, are utilized as pharmacologically active compounds (referred to hereinafter as "Therapeutics").

An altered antibody of the invention can be used to isolate a particular target using standard techniques, such as immunoaffinity, chromatography or immunoprecipitation. Altered antibodies of the invention (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibodies of the invention, including polyclonal, monoclonal, humanized and fully human antibodies, may be used as therapeutic agents. Such agents will generally be employed to treat or prevent a disease or pathology associated with aberrant expression or activation of a given target in a subject. An antibody preparation, preferably one having high specificity and high affinity for its target antigen, is administered to the subject and will generally have an effect due to its binding with the target. Administration of the antibody may abrogate or inhibit or interfere with the signaling function of the target. Administration of the antibody may abrogate or inhibit or interfere with the binding of the target with an endogenous ligand to which it naturally binds. For example, the antibody binds to the target and neutralizes LPS-induced proinflammatory cytokine production.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies or a fragment thereof of the invention can be administered for the treatment of a variety of diseases and disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of a given target (or a protein fragment thereof) in a sample. In some embodiments, the antibody contains a detectable label. Antibodies are polyclonal, or more preferably, monoclonal. An intact antibody, or a fragment thereof (e.g., $F_{ab}$, scFv, or $F_{(ab)2}$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Pharmaceutical Compositions

The antibodies or soluble chimeric polypeptides of the invention (also referred to herein as "active compounds"), and derivatives, fragments, analogs and homologs thereof, can be incorporated into pharmaceutical compositions suitable for administration. Such compositions typically comprise the antibody or soluble chimeric polypeptide and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1

Generation of Monoclonal Antibodies

The following studies describe the use of antibodies that recognize an epitope on TLR4, MD2 and/or the TLR4/MD2 complex. The antibodies used in the studies presented herein were generated using the methods described in co-pending U.S. application Ser. Nos. 11/009,939, filed Dec. 10, 2004 and 11/151,916, filed Jun. 15, 2004 and in WO 05/065015, filed Dec. 10, 2004 and PCT/US2005/020930, filed Jun. 15, 2004, each of which is hereby incorporated by reference in its entirety.

The amino acid and nucleic acid sequences of the heavy chain variable (VH) and light chain variable (VL) regions of the anti-TLR4/MD2 antibodies are shown below. The amino acids encompassing the complementarity determining regions (CDR) as defined by Chothia et al. 1989, E. A. Kabat et al., 1991 are highlighted in underlined and italicized text below. (See Chothia, C, et al., Nature 342:877-883 (1989); Kabat, E A, et al., Sequences of Protein of immunological interest, Fifth Edition, US Department of Health and Human Services, US Government Printing Office (1991)).

```
18H10 VH nucleotide sequence
   1caggtgcaac tgcagcagtc tggggctgat cttgtgaggc caggggcctt
      q  v  q  l  q  q  s  g  a  d  l  v  r  p  g  a
  51agtcaagttg tcctgcacag cttctggctt caacattaaa gactcctata
      l  v  k  l  s  c  t  a  s  g  f  n  i  k  d  s  y
 101tacactgggt gaagaagagg cctgaatggg gcctggagtg gattggatgg
      i  h  w  v  k  k  r  p  e  w  g  l  e  w  i  g  w
 151actgatcctg agaatgttaa ttctatatat gacccgaggt ttcagggcaa
      t  d  p  e  n  v  n  s  i  y  d  p  r  f  q  g
 201ggccagtata acagcagaca catcctccaa cacagccttc cttcagctca
      k  a  s  i  t  a  d  t  s  s  n  t  a  f  l  q  l
 251ccagcctgac atctgaggac actgccgtct attactgtgc taggggttat
      t  s  l  t  s  e  d  t  a  v  y  y  c  a  r  g  y
 301aacggtgttt actatgctat ggactactgg ggccaaggga cctcagtcac
      n  g  v  y  y  a  m  d  y  w  g  q  g  t  s  v
 351cgtctcctca (SEQ ID NO: 1)
      t  v  s  s  (SEQ ID NO: 2)

18H10 VH protein sequence
   1qvqlqqsgad lvrpgalvkl sctasgfnik dsyihwvkkr pewglewigw 51tdpenvnsiy dprfqgkasi tadtssntaf lqltsltsed tavyycargy 101ngvyyamdyw gqgtsvtvss(SEQ ID NO: 2)

181110 VH CDR protein sequences
dsyih (SEQ ID NO: 3)
```

-continued wtdpenvnsiydprfqg (SEQ ID NO: 4)

gyngvyyamdy (SEQ ID NO: 5)

181110 VL nucleotide sequence
```
  1caaattgttc tcacccagtc tccatcaatc atgtctgcgt ctctagggga
      q   i   v   l   t   q   s   p   s   i   m   s   a   s   l   g
 51ggagatcacc ctaacctgca gtgccagctc gagtgtaatt tacatgcact
      e   e   i   t   l   t   c   s   a   s   s   s   v   i   y   m   h
101ggtaccagca aagtcaggc acttctccca aactcttgat ttataggaca
      w   y   q   q   k   s   g   t   s   p   k   l   l   i   y   r   t
151tacaacctgg cttctggagt cccttctcgc ttcagtggca gtgggtctgg
      y   n   l   a   s   g   v   p   s   r   f   s   g   s   g   s
201gaccttttat tctctcacaa tcagcagtgt ggaggctgaa gatgctgccg
      g   t   f   y   s   l   t   i   s   s   v   e   a   e   d   a   a
251attattactg ccatcagtgg agtagttttc cgtacacgtt cggaggggggg
      d   y   y   c   h   q   w   s   s   f   p   y   t   f   g   g
301accaagctgg aaatcaaacg g (SEQ ID NO: 6)
      t   k   l   e   i   k   r (SEQ ID NO: 7)
```

181110 VL protein sequence
```
  1qivltqspsi msaslgeeit ltcsasssvi ymhwyqqksg tspklliyrt
 51ynlasgvpsr fsgsgsgtfy sltissveae daadyyhqw ssfpytfggg
101tkleikr (SEQ ID NO: 7)
```

181110 VL CDR protein sequences
sasssviymh (SEQ ID NO: 8)

rtynlas (SEQ ID NO: 9)

hqwssfpyt (SEQ ID NO: 10)

16G7 VH nucleotide sequence
```
  1aggtgaaact gcaggagtct ggagctgagc tgatgaagcc tggggcctca
      v   k   l   q   e   s   g   a   e   l   m   k   p   g   a   s
 51gtgaagatat cctgcaaggc tactggctac aaattcagtg actactggat
      v   k   i   s   c   k   a   t   g   y   k   f   s   d   y   w
101agagtggata aaacagaggc ctggacatgg ccttgagtgg attggagaga
      i   e   w   i   k   q   r   p   g   h   g   l   e   w   i   g   e
151ttttgcctgg aagtggtagt actaactaca atgaggactt caaggacaag
      i   l   p   g   s   g   s   t   n   y   n   e   d   f   k   d   k
201gccacattca cttcagatac atcctccaac acagcctaca tgcaactcag
      a   t   f   t   s   d   t   s   s   n   t   a   y   m   q   l
251cagcctgaca tctgaagact ctgccgtcta ttactgtgca aaagaggaga
      s   s   l   t   s   e   d   s   a   v   y   y   c   a   k   e   e
301gggcgtacta ctttggctat tggggccaag ggaccacggt caccgtctcc
      r   a   y   y   f   g   y   w   g   q   g   t   t   v   t   v   s
351tca (SEQ ID NO: 11)
      s (SEQ ID NO: 12)
```

16G7 VH protein sequence
  1vklqesgaelmkpgasvkiscka tgykfs*dywie*wikqrpghglewig*e*

51*ilpgsgstnynedfkd*katftsdtssntaymqlssltsedsavyycak*ee*

101*rayyfgy*wgqgttvtvss (SEQ ID NO: 12)

16G7 VH CDR protein sequences
dywie (SEQ ID NO: 13)

eilpgsgstnynedfkd (SEQ ID NO: 14)

eerayyfgy (SEQ ID NO: 15)

16G7 VL nucleotide sequence
  1gatgttttga tgacccaaac tccactctcc ctgcctgtca gtcttggaga
       d  v  l  m  t  q  t  p  l  s  l  p  v  s  l  g
 51tcaagcctcc atctcttgca ggtctagtca gagccttgaa aacagtaatg
       d  q  a  s  i  s  c  r  s  s  q  s  l  e  n  s  n
101gaaacaccta tttgaactgg tacctccaga aaccaggcca gtctccacag
       g  n  t  y  l  n  w  y  l  q  k  p  g  q  s  p  q
151ctcctgatct acagggtttc caaccgattt tctggggtcc tagacaggtt
       l  l  i  y  r  v  s  n  r  f  s  g  v  l  d  r
201cagtggtagt ggatcaggga cagatttcac actgaaaatc agcagagtgg
       f  s  g  s  g  s  g  t  d  f  t  l  k  i  s  r  v
251aggctgagga tttgggagtt tatttctgcc tccaagttac acatgtccct
       e  a  e  d  l  g  v  y  f  c  l  q  v  t  h  v  p
301cccacgttcg gtgctgggac caagctggaa ctgaaacgg (SEQ ID NO: 16)
       p  t  f  g  a  g  t  k  l  e  l  k  r (SEQ ID NO: 17)

16G7 VL protein sequence
  1dvlmtqtplslpvslgdqasisc*rssqslensngntyln*wylqkpgqspq 51lliy*rvsnrfs*gvldrfsgsgsgtdftlkisrveaedlgvyfc*lqvthvp*

101*pt*fgagtklelkr (SEQ ID NO: 17)

16G7 VL CDR protein sequences
rssqslensngntyln (SEQ ID NO: 18)

rvsnrfs (SEQ ID NO: 19)

lqvthvppt (SEQ ID NO: 20)

15C1 VH nucleotide sequence
  1gatgtgcagc ttcaggagtc aggacctgac ctaatacaac cttctcagtc actttcactc acctgcactg
       d  v  q  l  q  e  s  g  p  d  l  i  q  p  s  q  s  l  s  l  t  c  t
 71tcactggcta ctccatcacc ggtggttata gctggcactg gatccggcag tttccaggaa acaaactgga
       v  t  g  y  s  i  t  g  g  y  s  w  h  w  i  r  q  f  p  g  n  k  l
141atggatgggc tacatccact acagtggtta cactgacttc aacccctctc tcaaaactcg aatctctatc
       e  w  m  g  y  i  h  y  s  g  y  t  d  f  n  p  s  l  k  t  r  i  s  i
211actcgagaca catccaagaa ccagttcttc ctgcagttga attctgtgac tactgaagac acagccacat
       t  r  d  t  s  k  n  q  f  f  l  q  l  n  s  v  t  t  e  d  t  a  t
281attactgtgc aagaaaagat ccgtccgacg gatttcctta ctggggccaa gggactctgg tcactgtctc
       y  y  c  a  r  k  d  p  s  d  g  f  p  y  w  g  q  g  t  l  v  t  v
351tgca (SEQ ID NO: 21)
       s  a (SEQ ID NO: 22)

15C1 VH protein sequence
```
  1 dvqlqesgpd liqpsqslsl tctvtgysit ggyswhwirq fpgnklewmg
 51 yihysgytdf npslktrisi trdtsknqff lqlnsvtted tatyycarkd
101 psdgfpywgq gtivtvsa (SEQ ID NO: 22)
```

15C1 VH CDR protein sequences
ggyswh (SEQ ID NO: 23)

yihysgytdfnpslkt (SEQ ID NO: 24)

kdpsdgfpy (SEQ ID NO: 25)

15C1 VL nucleotide sequence
```
  1 gacattgtga tgacccagtc tccagccacc ctgtctgtga ctccaggtga tagagtctct
      d   i   v   m   t   q   s   p   a   t   l   s   v   t   p   g   d   r   v   s
 61 ctttcctgca gggccagcca gagtatcagc gaccacttac actggtatca acaaaaatca
      l   s   c   r   a   s   q   s   i   s   d   h   l   h   w   y   q   q   k   s
121 catgagtctc cacggcttct catcaaatat gcttcccatg ccatttctgg gatcccctcc
      h   e   s   p   r   l   l   i   k   y   a   s   h   a   i   s   g   i   p   s
181 aggttcagtg gcagtggatc agggacagat ttcactctca gcatcaaaag tgtggaacct
      r   f   s   g   s   g   s   g   t   d   f   t   l   s   i   k   s   v   e   p
241 gaagatattg gggtgtatta ctgtcaaaat ggtcacagtt ttccgctcac gttcggtgct
      e   d   i   g   v   y   y   c   q   n   g   h   s   f   p   l   t   f   g   a
301 gggaccaagc tggagctgaa a (SEQ ID NO: 26)
      g   t   k   l   e   l   k (SEQ ID NO: 27)
```

15C1 VL protein sequence
```
  1 divmtqspat lsvtpgdrvs lscrasqsis dhlhwyqqks hesprllikY
 51 ashaisgips rfsgsgsgtd ftlsiksvep edigvyycqn ghsfpltfga
101 gtklelk (SEQ ID NO: 27)
```

15C1 VL CDR protein sequences
rasqsisdhlh (SEQ ID NO: 28)

yashais (SEQ ID NO: 29)

qnghsfplt (SEQ ID NO: 30)

7E3 VII nucleotide sequence
```
  1 caggttactc tgaaagagtc tggccctggg atattgcagc cctcccagac cctcagtctg acttgttctt
      q   v   t   l   k   e   s   g   p   g   i   l   q   p   s   q   t   l   s   l   t   c   s
 71 tctctgggtt ttcactgacc acttataata taggagtagg ctggattcgt cagccttcag ggaagggtct
      f   s   g   f   s   l   t   t   y   n   i   g   v   g   w   i   r   q   p   s   g   k   g
141 ggagtggctg gcacacattt ggtggaatga taatatttac tataatacag tccttaagag ccgactcaca
      l   e   w   l   a   h   i   w   w   n   d   n   i   y   y   n   t   v   l   k   s   r   l   t
211 ttctccaagg atacctccaa caaccaggtt ttcctcaaga tcgccagtgt ggacattgca gatactgcca
      f   s   k   d   t   s   n   n   q   v   f   l   k   i   a   s   v   d   i   a   d   t   a
281 catattactg tattcgaatg gctgagggaa ggtacgacgc tatggactac tggggtcaag gaacctcagt
      t   y   y   c   i   r   m   a   e   g   r   y   d   a   m   d   y   w   g   q   g   t   s
351 caccgtctcc tca (SEQ ID NO: 31)
      v   t   v   s   s (SEQ ID NO: 32)
```

-continued

7E3 VH protein sequence
```
  1qvtlkesgpg ilqpsqtlsl tcsfsgfslt tynigvgwir qpsgkglewl 51ahiwwndniy yntvlksrlt fskdtsnnqv flkiasvdia dtatyycinm 101 aegrydamdy wgqgtsvtvs s (SEQ ID NO: 32)
```

7E3 VII CDR protein sequences
tynigvg (SEQ ID NO: 33)

hiwwndniyyntvlks (SEQ ID NO: 34)

maegrydamdy (SEQ ID NO: 35)

7E3 VL nucleotide sequence
```
  1gctatccaga tgacacagag tacatcctcc ctgtctgcct ctctgggaga cagagtcacc atcaattgca
      a   i   q   m   t   q   s   t   s   s   l   s   a   s   l   g   d   r   v   t   i   n   c 71gggcaagtca ggacatcacc aattatttaa attggtatca gcagaaacca gatggaactg tcagactcct
      r   a   s   q   d   i   t   n   y   l   n   w   y   q   q   k   p   d   g   t   v   r   l 141gatctattat acatcaaaat tacactcagg agccccatca aggttcagtg gccgtgggtc tggaacagat
      l   i   y   y   t   s   k   l   h   s   g   a   p   s   r   f   s   g   r   g   s   g   t   d 211tattctctca ccattagtaa cctggagcaa gaggatattg ccacttactt ttgccaacag ggtaatacgt
      y   s   l   t   i   s   n   l   e   q   e   d   i   a   t   y   f   c   q   q   g   n   t 281ttccgtggac gttcggtgga ggcaccaaac tggaaatcaa acgt (SEQ ID NO: 36)
      f   p   w   t   f   g   g   g   t   k   l   e   i   k   r (SEQ ID NO: 37)
```

7E3 VL protein sequence
```
  1aigmtqstss lsaslgdrvt incrasqdit nylnwyqqkp dgtvrlliyy 51 tsklhsgaps rfsgrgsgtd ysltisnleq ediatyfcqq gntfpwtfgg 101gtkleikr (SEQ ID NO: 37)
```

7E3 VL CDR protein sequences
rasqditnyln (SEQ ID NO: 38)

ytsklhs (SEQ ID NO: 39)

qqgntfpwt (SEQ ID NO: 40)

The ability of each monoclonal antibody to neutralize LPS-induced IL-8 induction on TLR4/MD2 transfected cells was analyzed by pre-incubating the transfected cells with each monoclonal antibody for 30 minutes prior to LPS administration. In addition, each monoclonal antibody was tested for the ability to neutralize LPS-induced IL-8 induction in whole blood.

The specificity of each monoclonal antibody was tested by evaluating the binding of each monoclonal antibody to cells transfected with the following combinations: (1) human TLR4 and human MD-2; (2) rabbit TLR4 and rabbit MD-2; (3) human TLR4 and rabbit MD-2; (4) rabbit TLR4 and human MD-2.

Example 2

Humanization of Murine Monoclonal Antibodies

The following studies describe the humanization of antibodies that recognize an epitope on TLR4, MD2 and/or the TLR4/MD2 complex. The antibodies were humanized using the methods described in co-pending U.S. application Ser. No. 11/151,916, filed Jun. 15, 2004 (U.S. Patent Publication No. US 2008-0050366 A1) and in PCT/IB2005/004206, filed Jun. 15, 2004 (PCT Publication No. WO 07/110,678), each of which is hereby incorporated by reference in its entirety.

The hu15C1 antibodies include the variable heavy chain ($V_H$) 4-28 shown below in SEQ ID NO:45 or the $V_H$ 3-66 shown below in SEQ ID NO:46. The hu15C1 antibodies include the variable light chain ($V_L$) L6 shown below in SEQ ID NO:47 or A26 shown below in SEQ ID NO:48. The amino acids encompassing the complementarity determining regions (CDR) as defined by Chothia et al. 1989, E. A. Kabat et al., 1991 are boxed in the sequences provided below. (See Chothia, C, et al., Nature 342:877-883 (1989); Kabat, E A, et al., Sequences of Protein of immunological interest, Fifth Edition, US Department of Health and Human Services, US Government Printing Office (1991)).

15C1 Hu V$_H$ version 4-28

(SEQ ID NO: 45)

QVQLQESGPG LVKPSDTLSL TCAVSGYSI X$_1$ GGYSWHWIRQ PPGKGLEW X$_2$G YIHYSGYTDF NPSLKTR X$_3$T X$_4$ SRDTSKNQFS LKLSSVTAVD TAVYYCARKD PSDGFPYWGQ GTLVTVSS

| | |
|---|---|
| CDR 1: GGYSWH | (SEQ ID NO: 23) |
| CDR 2: YIHYSGYTDFNPSLKT | (SEQ ID NO: 24) |
| CDR 3: KDPSDGFPY | (SEQ ID NO: 25) |

Where X$_1$ is Thr or Ser
Where X$_2$ is Ile or Met
Where X$_3$ is Val or Ile
Where X$_4$ is Met or Ile

15C1 Hu V$_H$ version 3-66

(SEQ ID NO: 46)

EVQLVESGGG LVQPGGSLRL SCAX$_1$SGYSIT GGYWHWVRQ APGKGLEWX$_2$S YIHYSGYTDF NPSLKTRFTI SRDNSKNTX$_3$Y LQMNSLRAED TAVYYCARKD PSDGFPYWGQ GTLVTVSS

| | |
|---|---|
| CDR 1: GGYSWH | (SEQ ID NO: 23) |
| CDR 2: YIHYSGYTDFNPSLKT | (SEQ ID NO: 24) |
| CDR 3: KDPSDGFPY | (SEQ ID NO: 25) |

Where X$_1$ is Ala or Val
Where X$_2$ is Val or Met
Where X$_3$ is Leu or Phe

15C1 Hu VL version L6

(SEQ ID NO: 47)

EIVLTQSPAT LSLSPGERAT LSCRASQSIS DHLHWYQQKP GQAPRLLIX$_1$Y ASHAISGIPA RFSGSGSGTD FTLTISSLEP EDFAVYYCQN GHSFPLTFGG GTKVEIK

| | |
|---|---|
| CDR1: RASQSISDHLH | (SEQ ID NO: 28) |
| CDR2: YASHAIS | (SEQ ID NO: 29) |
| CDR3: QNGHSFPLT | (SEQ ID NO: 30) |

Where X$_1$ is Lys or Tyr

15C1 Hu VL version A26

(SEQ ID NO: 48)

EIVLTQSPDF QSVTPKEKVT ITCRASQSIS DHLHWYQQKP DQSPKLLIKY ASHAISGVPS RFSGSGSGTD FTLTINSLEA EDAATYYCQN GHSFPLTFGG GTKVEIK

| | |
|---|---|
| CDR1: RASQSISDHLH | (SEQ ID NO: 28) |
| CDR2: YASHAIS | (SEQ ID NO: 29) |
| CDR3: QNGHSFPLT | (SEQ ID NO: 30) |

The hu18H10 antibodies include the V$_H$ 1-69 shown below in SEQ ID NO:49. The hu18H10 antibodies include the V$_L$ L6 shown below in SEQ ID NO:50. The amino acids encompassing the complementarity determining regions (CDR) as defined by Chothia et al. 1989, E. A. Kabat et al., 1991 are boxed in the sequences provided below. (See Chothia, C, et al., Nature 342:877-883 (1989); Kabat, E A, et al., Sequences of Protein of immunological interest, Fifth Edition, US Department of Health and Human Services, US Government Printing Office (1991)).

| 18H10 Hu VH version 1-69 |
| --- |

(SEQ ID NO: 49)

```
QVQLVQSGAE VKKPGSSVKV SCKASGFNIK DSYIHWVRQA PGQGLEWX₁GW
TDPENVNSIY DPRFQGRVTI TADX₂STSTAY X₃ELSSLRSED TAVYYCARGY
NGVYYAMDYW GQGTTVTVSS
```

CDR1: DSYIH  (SEQ ID NO: 3)

CDR2: WTDPENVNSIYDPRFQG  (SEQ ID NO: 4SEQ ID NO: 4)

CDR3: GYNGVYYAMDY  (SEQ ID NO: 5)

Where $X_1$ is Met or Ile
Where $X_2$ is Lys or Thr
Where $X_3$ is Met or Leu

| 18H10 Hu VL version L6 |
| --- |

(SEQ ID NO: 50)

```
EIVLTQSPAT LSLSPGERAT LSCSASSSVI TMHWYQQKPG QAPRLLIYRT
YNLASGIPAR FSGSGSGTDX₁ TLTISSLEPE DFAVYYCHQW SSFPYTFGQG TKVEIK
```

CDR1: SASSSVIYMH  (SEQ ID NO: 8)

CDR2: RTYNLAS  (SEQ ID NO: 9)

CDR3: HQWSSFPYT  (SEQ ID NO: 10)

Where $X_1$ is Phe or Tyr

The hu7E3 antibodies include the $V_H$ 2-70 shown below in SEQ ID NO:51 or the $V_H$ 3-66 shown below in SEQ ID NO:52. The hu7E3 antibodies include the $V_L$ L19 shown below in SEQ ID NO:53. The amino acids encompassing the complementarity determining regions (CDR) as defined by Chothia et al. 1989, E. A. Kabat et al., 1991 are boxed in the sequences provided below. (See Chothia, C, et al., Nature 342:877-883 (1989); Kabat, E A, et al., Sequences of Protein of immunological interest, Fifth Edition, US Department of Health and Human Services, US Government Printing Office (1991)).

| 7E3 Hu VH version 2-70 |
| --- |

(SEQ ID NO: 51)

```
QVTLRESGPA LVKPTQTLTL TCTFSGFSLX₁ TYNIGVGWIR QPPGKALEWL
AHIWWNDNIY YNTVLKSRLT X₂SKDTSKNQV VLTMTNMDPV DTATYYCX₃FM
AEGRYDAMDY WGQGTLVTVS S
```

CDR1: TYNIGVG  (SEQ ID NO: 33)

CDR2: HIWWNDNIYYNTVLKS  (SEQ ID NO: 34)

CDR3: MAEGRYDAMDY  (SEQ ID NO: 35)

Where $X_1$ is Ser or Thr
Where $X_2$ is Ile or Phe
Where $X_3$ is Ile or Ala

---

7E3 Hu VH version 3-66

(SEQ ID NO: 52)

```
EVQLVESGGG LVQPGGSLRL SCAX₁SGFSLT TYNIGVGWVR QAPGKGLEWX₂
SHIWWNDNIY YNTVLKSRLT X₃SX₄DNSKNTX₅ YLQMNSLRAE DTAVYYCX₆RM
AEGRYDAMDY WGQGTLVTVS S
```

CDR1: TYNIGVG (SEQ ID NO: 33)

CDR2: HIWWNDNIYYNTVLKS (SEQ ID NO: 34)

CDR3: MAEGRYDAMDY (SEQ ID NO: 35)

---

Where $X_1$ is Phe or Ala
Where $X_2$ is Val or Leu
Where $X_3$ is Ile or Phe
Where $X_4$ is Lys or Arg
Where $X_5$ is Leu or Val
Where $X_6$ is Ile or Ala

---

7E3 Hu VL version L19

(SEQ ID NO: 53)

```
DIQMTQSPSS VSASVGDRVT ITCRASQDIT NYLNWYQQKP GKAPKLLIYY
TSKLHSGVPS RFSGSGSGTD X₁TLTISSLQP EDFATYX₂CQQ GNTFPWTFGG GTKVEIK
```

CDR1: RASQDITNYLN (SEQ ID NO: 38)

CDR2: YTSKLHS (SEQ ID NO: 39)

CDR3: QQGNTFPWT (SEQ ID NO: 40)

---

Where $X_1$ is Phe or Tyr
Where $X_2$ is Tyr or Phe

The chimeric antibodies described above in Example 1 were used to evaluate the ability of the humanized monoclonal antibodies to bind to the human TLR4/MD2 complex. Each of the humanized monoclonal antibodies was found to bind TLR4/MD2 in a similar manner to the corresponding chimeric antibody. In addition, the chimeric antibodies were used to evaluate the ability of the humanized monoclonal antibodies to inhibit LPS-induced IL-6 production in human whole blood. Each of the humanized monoclonal antibodies was found to inhibit the effects of LPS on blood leukocytes in a similar manner to the corresponding chimeric antibody.

Example 3

Increasing the Potency of Modified Monoclonal Antibodies

The studies described herein are directed methods of increasing the potency of neutralizing antibodies by modifying one or more residues in the Fc portion of an antibody. In particular, the studies described herein use an altered neutralizing antibody that recognizes the TLR4/MD2 complex. These anti-TLR4/MD2 antibodies are modified to include one or more mutations in the Fc portion, specifically in the CH2 domain of the Fc portion.

The murine IgG1/K anti-human TLR4/MD2 monoclonal antibody discussed above and referred to herein as "mu15C1" was modified by replacing the mouse constant regions of mu15C1 with those of a human IgG1 to produce a chimeric antibody, referred to herein as "chimeric IgG1 15C1" (FIG. 1A). The relative binding affinity of the corresponding MAbs was unchanged.

The ability of the chimeric IgG1 15C1 antibody to neutralize the effects of LPS was evaluated using the TLR4/MD-2 transfected cell line. HEK 293 cells were plated in 96-well plates at $6 \times 10^4$ cells/well. The medium was removed on the day of the experiment and 30 µl of medium containing 6% heat-inactivated human plasma was added. Mouse IgG1 15C1 (square) or chimeric IgG1 15C1 (triangle) MAbs were diluted in 30 µl basal medium to the appropriate concentration, and added to the cells for 1 hour at 37° C. LPS was diluted in 30 µl medium, added to the cells and left to incubate for 24 hours at 37° C. IL-8 secretion in the culture supernatant was monitored by ELISA (Endogen).

Figure 1B:
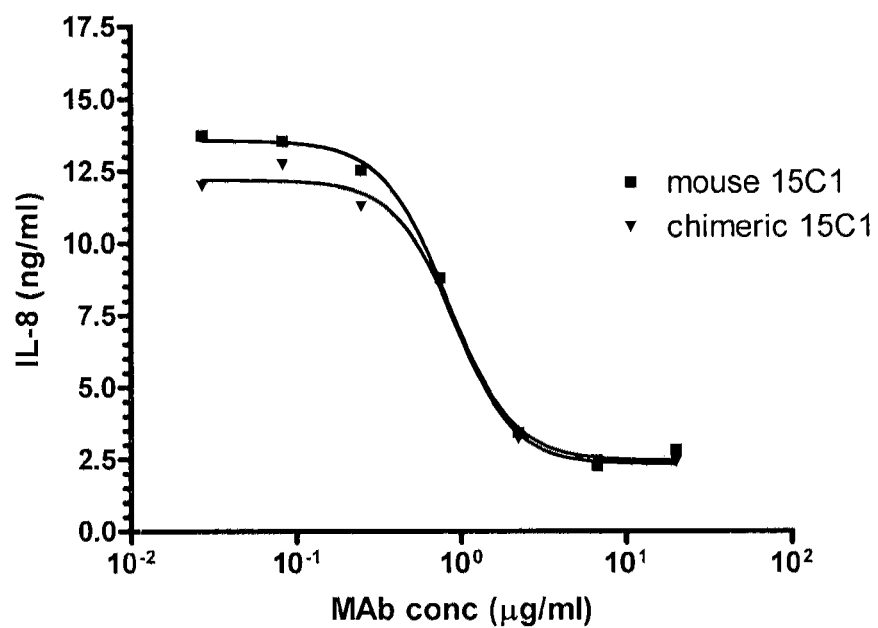
FIG. 1B is a graph depicting LPS-dependent IL-8 production on human embryonic kidney 293 cells (HEK 293) expressing human TLR4/MD2 by mouse and chimeric IgG1 15C1.

The chimeric antibody was able to neutralize the effects of LPS on the TLR4/MD-2 transfected cell line HEK 293 (as measured by IL-8 production). FIG. 1B shows that 15C1 on a mouse IgG1 backbone (referred as mouse IgG1 15C1; see schematic description in FIG. 1A) and 15C1 on a human IgG1 backbone (referred as chimeric IgG1 15C1; see schematic description in FIG. 1A) are equivalent in their neutralizing capacity on this cell line.

The ability of the chimeric antibody to neutralize the effects of LPS in human whole blood was also evaluated. Fresh heparinated blood from healthy volunteers was obtained by venipuncture and diluted 1:2 with RPMI 1640. The diluted blood was plated at 60 µl/well in a 96-well plate and incubated for 15 minutes at 37° C. Then 30 µl of serial dilutions in RPMI 1640 of the mouse and chimeric IgG1 15C1 MAbs were added to the blood and incubated for an hour at 37° C. Blood cells were then stimulated by adding 30

µl of *E. coli* K12 LPS (2 ng/ml final in RPMI 1640 containing 0.1% HSA) to the wells and incubated for 6 hours. IL-6 production was then measured by ELISA.

Figure 2:
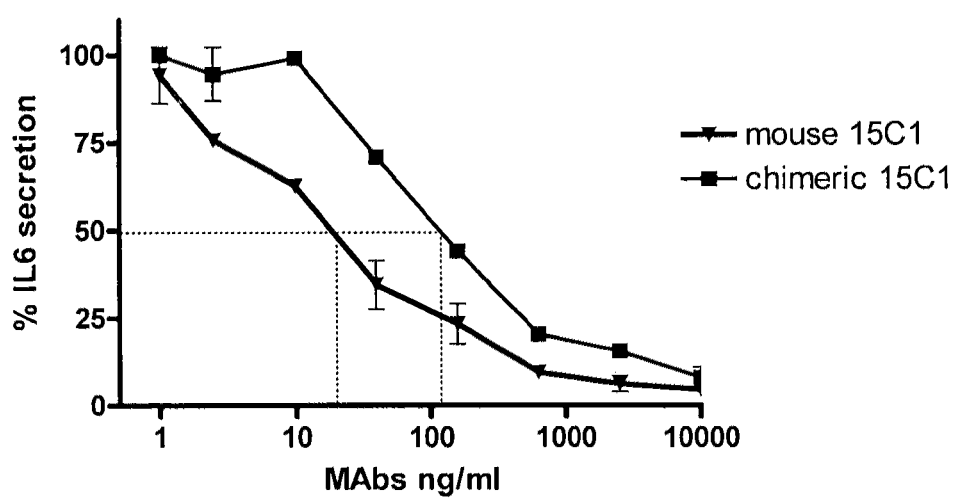
FIG. 2 is a graph depicting LPS-dependent IL-6 production in human whole blood assay by mouse and chimeric IgG1 15C1 antibodies.

In the human whole blood assay, a different profile for the murine and chimeric antibodies was seen. FIG. 2 shows that mouse IgG1 15C1 was significantly more potent in its ability to neutralize LPS than chimeric IgG1 15C1 (as measured by IL-6 production). This observation was more striking the lower the concentration of MAb used in the assay. It was concluded that this difference had to be attributed to the Fc region of the molecule, as the binding affinity of the two MAbs (typically involving the Fab region) was equivalent.

Furthermore, it was thought that this difference was mediated via an Fc receptor-dependent mechanism. On HEK 293 cells (FIG. 1B) negative for Fc gamma receptors expression, the two MAbs, chimeric and murine 15C1, were equally potent whereas in an ex-vivo human whole blood assay, where leucocytes are positive for Fc gamma receptors expression, a clear difference was seen between them.

To further demonstrate the involvement of interactions between the MAb Fc portion and Fcγ receptors in a putative inhibitory response, a modification of mouse IgG1 15C1 was engineered to disrupt the ability of the antibody to engage cellular Fcγ receptors while retaining its affinity for its cognate antigen TLR4/MD2. The mutation of Asp to Ala at EU amino acid residue position 265 (D265A) was introduced into the mouse IgG1 15C1 gamma heavy chain gene, and this mutated sequence was expressed along with the 15C1 mouse kappa chain in PEAK cells to produce mutant (D265A) antibodies. In parallel recombinant wild type 15C1 heavy and light chains were co-expressed in PEAK cells to produce recombinant mouse IgG1 15C1. The mutation D265A when engineered in a mouse IgG1 isotype (IgG1-D265A) has been shown to anneal the binding of IgG1-D265A-containing immune complexes to mouse Fc-gamma receptors 10B (FcγRIIB), III (FcγRIII) and IV (FγRIV) (Nimmerjahn et al., Immunity, 2005, 23:41-51) as well as to nullify (.FcγRI) or greatly reduce its binding to all human Fc gamma receptors (FcγRIIA, FcγRIIB and FcγRIII). (Shields et al., JBC, 2001; 276:6591-6604).

The neutralizing capability of the recombinant mouse IgG1 15C1 and recombinant mouse IgG1-D265A 15C1 antibodies were evaluated in the human whole blood assay. In particular, fresh heparinated blood from healthy volunteers was obtained by venipuncture and diluted 1:2 with RPMI 1640. The diluted blood was plated at 60 µl/well in a 96-well plate and incubated for 15 minutes at 37° C. Then 30 ml of serial dilutions in RPMI 1640 of recombinant mouse IgG1 15C1 (rec-mouse IgG1 15C1) and recombinant mouse IgG1 15C1 containing the mutation Asp to Ala at EU position 265 (rec-mouse D265A 15C1) MAbs were added to the blood and incubated for an hour at 37° C. Blood cells were then stimulated by adding 30 µl of *E. coli* K12 LPS (2 ng/ml final in RPMI 1640 containing 0.1% HSA) to the wells and incubated for 6 hours. IL-6 production was then measured by ELISA.

Figure 3:
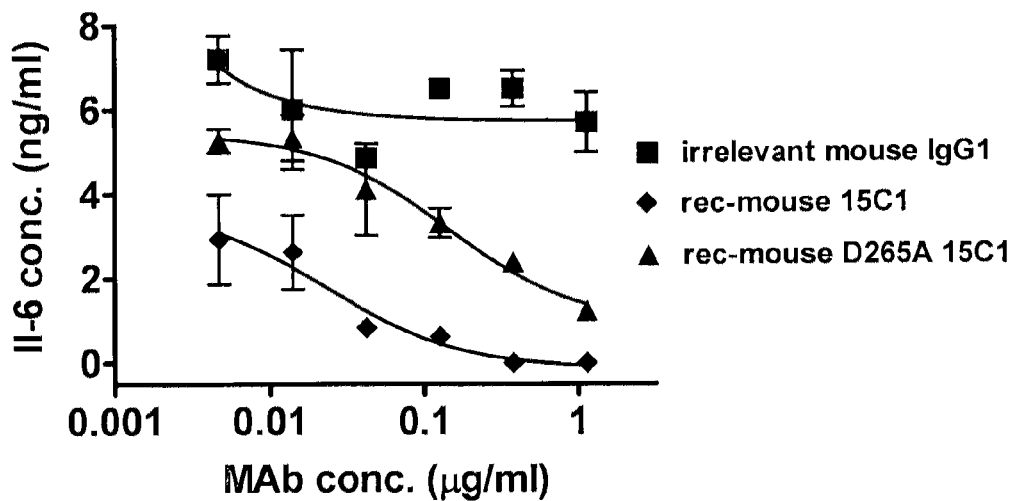
FIG. 3 is a graph depicting LPS-dependent IL-6 production in human whole blood assay by recombinant mouse IgG1 15C1 and D265A mutant antibodies.

In a human whole blood experiment (FIG. 3) recombinant mouse D265A IgG1 (rec-D265A mouse IgG1 15C1) was significantly less potent at inhibiting the effects of LPS (as measured by IL-6 production) than recombinant mouse IgG1 15C1 WT IgG1 (rec mouse IgG1 15C1). This result confirmed the hypothesis that binding of the Fc portion of mouse IgG1 to human Fcγ receptors contributes to the potency of 15C1 to neutralize LPS pro-inflammatory stimulation.

Mouse IgG1 has been described in the literature to have a high affinity for the human FcγRII or CD32. Indeed, this high affinity of mouse IgG1 for human CD32 rendered the discovery of this receptor possible. It was, therefore, hypothesized that CD32 would be the key target receptor for the Fc of mouse IgG1 on human leukocytes. In order to verify this possibility, a human whole blood assay was performed using two different anti-human CD32 antibody (AT10 which recognizes equally well CD32A and CD32B; and IV.3 which binds to CD32A and weakly to CD32B) in order to prevent the binding of the Fc of mouse IgG1 to this receptor. Fresh heparinated blood from healthy volunteers was obtained by venipuncture and diluted 1:2 with RPMI 1640. The diluted blood was plated at 60 µl/well in a 96-well plate and incubated for 15 minutes at 37° C. Then 30 µl of serial dilutions in RPMI 1640 of the mouse IgG1 1501 MAbs with or without mouse anti-human CD32 monoclonal antibody (Clone AT10, mouse IgG1, Catalog number MCA1075XZ, AbD Serotec, clone IV.3, mouse IgG2b, Catalog number 01470, StemCell Technologies) were added to the blood and incubated for an hour at 37° C. Blood cells were then stimulated by adding 30 µl of *E. coli* K12 LPS (2 ng/ml final in RPMI 1640 containing 0.1% HSA) to the wells and incubated for 6 hours. IL-6 production was then measured by ELISA.

Figure 4A:
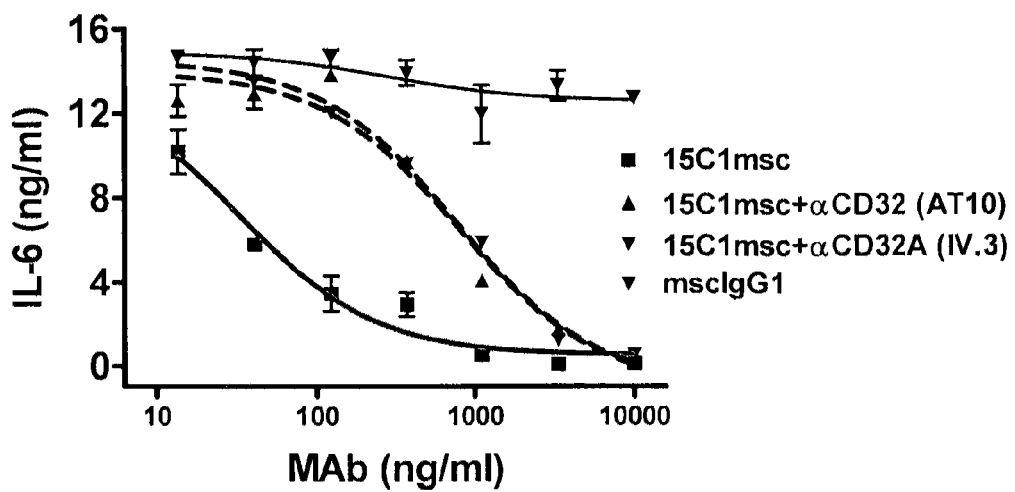
FIG. 4A Addition of either α-CD32 MAb AT10 or α-CD32A MAb IV.3 diminished MAb 15C1 inhibition of LPS to a similar extent, as measured by IL-6 production in whole blood.

In a human whole blood assay it was demonstrated (FIG. 4A) that both AT10 and IV.3 anti-human CD32 antibodies reduce the potency of mouse IgG1 15C1 to a similar level to that seen with chimeric IgG1 15C1. The fact that IV.3 binds strongly to CD32A, recognizes both phenotypic forms of FcγRIIA equally well and weakly to CD32B, point to the involvement of human CD32A rather than CD32B.

Figure 4B:
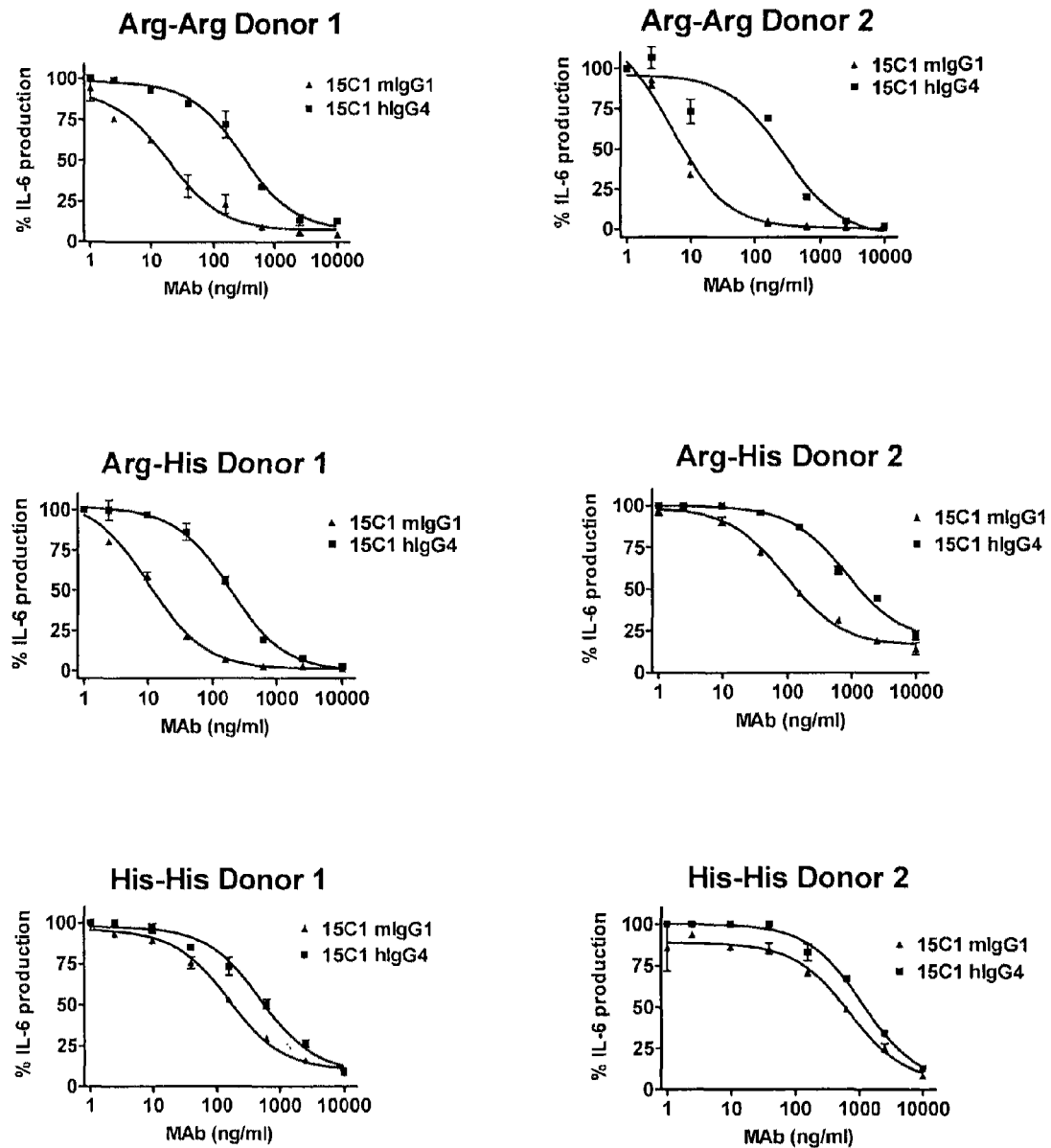
FIG. 4B. 15C1 mediated blockade of LPS-dependent TLR4 activation in whole blood derived from homozygous and heterozygous individuals using mouse IgG1 or human IgG4 version of 15C1. Because the magnitude of IL-6 production was variable among different donors, results are given as the percentage of inhibition of IL-6 release compared to values obtained with the isotype control antibody (which corresponding to 100% LPS activation). Errors bars show ±SEM.

CD32A contains a polymorphism (histidine or arginine) in its extracellular domain at amino acid 131. The nature of this polymorphism has an influence on the binding of mouse IgG1 to CD32A, with arginine homozygous individuals having a much higher affinity for mouse IgG1 than histidine homozygotes. Arginine/histidine heterozygotes have an intermediate affinity (Dijstelbloem, H. M. et al., 2001. *Trends Immunol.* 22:510-516). Healthy individuals were screened for their CD32A genotype at this polymorphism and tested 15C1-mediated blockade of LPS-dependent TLR4 activation in whole blood derived from homozygous and heterozygous individuals. For this experiment, 15C1 was produced in PEAK cells either in its original form (i.e. on a mouse IgG1 backbone) or as a chimeric MAb with the 15C1 variable region on a human IgG4 backbone. This format was chosen as human IgG4 is known to have a very poor affinity for CD32. Following protein A affinity chromatography purification, the integrity of both MAbs for TLR4/MD-2 binding on transfected CHO cells was confirmed and shown to be equivalent. In whole blood LPS-activation experiments, the mIgG1 version of 15C1 was considerably more potent at inhibiting TLR4 than the hIgG4 version when testing Arg/Arg and Arg/H is donors. In contrast, mIgG1 15C1 was only slightly more potent that hIgG4 15C1 in H is/His donors (FIG. 4B). IC50 values obtained for each dose response curve are shown in table 3. These values highlight the differences in potency between the 15C1mIgG1 and hIgG4 constructs for the different CD32 genotype donors. The mIgG1 construct shows a dramatic loss in potency from the Arg/Arg to the H is/His donors (~35-fold), whereas the hIgG4 construct shows a marginal loss in potency (~3 fold). These results reinforce the contribution of CD32A to the inhibitory activities of the 15C1 MAb on TLR4 signalling.

Identical results were obtained in human whole blood from the same donors using heat-inactivated *E. coli* as a stimulus ($10^6$ cfu/ml).

Figure 5A:
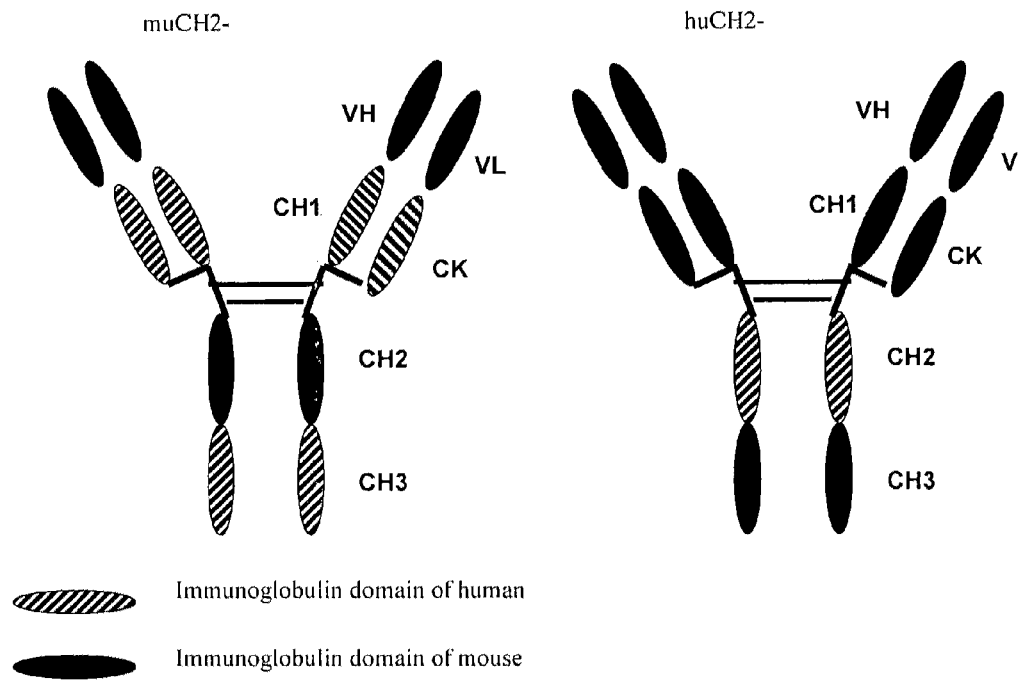
FIG. 5A is a schematic representation of chimeric and mouse IgG1 15C1 antibodies containing the mouse and human IgG1 CH2 domains, respectively. The mouse variable and constant domains of the light and heavy chain are in black. The human constant domains of the light and heavy chains are in hatched black. Mouse IgG1 15C1 is a mouse immunoglobulin of the IgG1 subclass specific for human TLR4. Chimeric IgG1 15C1 is a recombinant immunoglobulin consisting of the mouse heavy and light chain variable regions of 15C1 in fusion with human IgG1 heavy and Kappa light constant regions. V=variable domain; L=light chain; H=heavy chain; CK=Kappa constant domain of the light chain; CH1, CH2, CH3=constant domains of the heavy chain.

Studies were then designed to determine the critical region within the Fc region of a mouse IgG1 antibody that is sufficient to maintain the biological contribution of the whole Fc region. It is known in the literature that both CH2 and CH3 domains of the Fc region can contribute directly to the interaction with Fcγ receptors. In a first step towards the identification of the critical region contributing to this inhibitory effect, studies were designed to focus on the importance of the CH2 domain (EU positions 231 to 340, see alignment of CH2 domains in FIG. 16) since its role in the interaction of the Fc with Fcγ receptors is well documented. The CH2 domain of human IgG1 was replaced with that of mouse IgG1 (later referred as muCH2-chimeric IgG1 15C1; see FIG. 5A) and reciprocally the CH2 domain of mouse IgG1 was replaced with that of human IgG1 (later referred as huCH2-mouse IgG1 15C1; see FIG. 5A). The antibodies were produced in PEAK cells and purified from transfected-cell supernatants by protein G affinity column chromatography. Equivalent binding to CHO TLR4/MD2 transfectants by FACS was observed indicating that the change of CH2 domain had no significant influence on the relative affinity for the antigen. The neutralizing capability of murine 15C1, huCH2-mouse IgG1 15C1, chimeric IgG1 15C1 and muCH2-chimeric IgG1 15C1 was evaluated in the human whole blood assay. Fresh heparinated blood from healthy volunteers was obtained by venipuncture and diluted 1:2 with RPMI 1640. The diluted blood was plated at 60 µl/well in a 96-well plate and incubated for 15 minutes at 37° C. Then 30 µl of serial dilutions in RPMI 1640 of the mouse IgG1 15C1, chimeric IgG1 15C1, mouse IgG1 15C1 containing human CH2 and chimeric IgG1 15C1 containing mouse CH2 MAbs were added to the blood and incubated for an hour at 37° C. Blood cells were then stimulated by adding 30 µl of E. coli K12 LPS (2 ng/ml final in RPMI 1640 containing 0.1% HSA) to the wells and incubated for 6 hours. IL-6 production was then measured by ELISA.

Figure 5B:
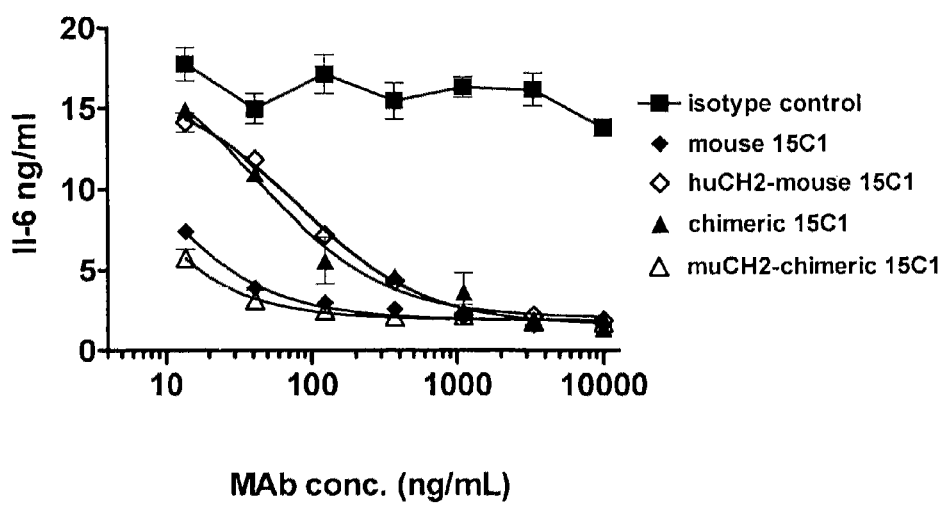
FIG. 5B is a graph depicting LPS-dependent IL-6 production in human whole blood assay by swapping the CH2 domain between mouse and chimeric IgG1 15C1 antibodies.
Figure 6C:
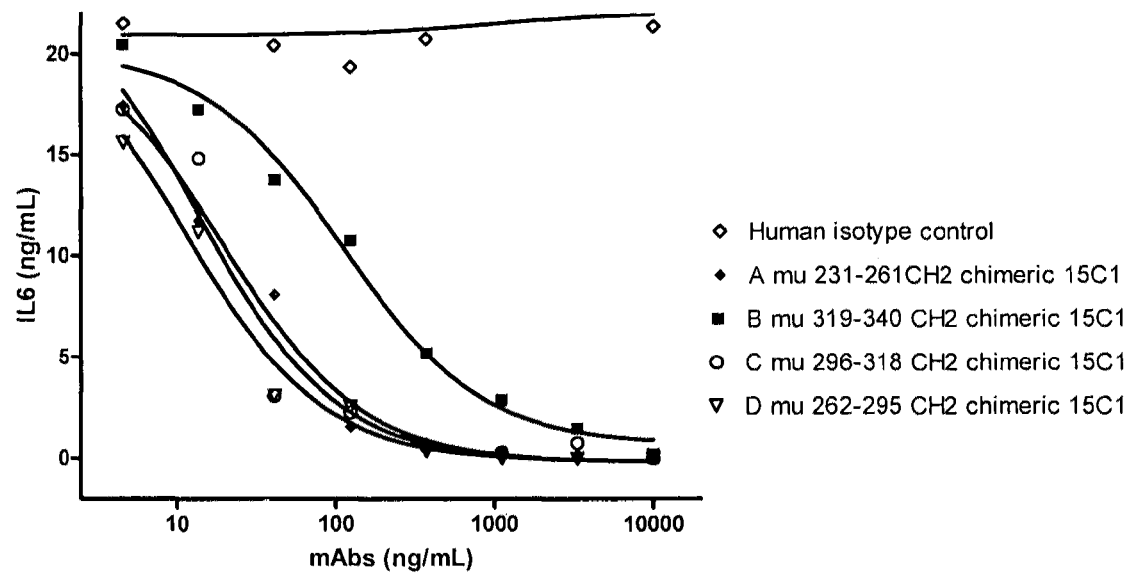
FIG. 6C is a graph depicting LPS-dependent IL-6 production in human whole blood assay by chimeric IgG1 15C1 containing hybrid CH2 sub-region domains between mouse and human IgG1.
Figure 7A:
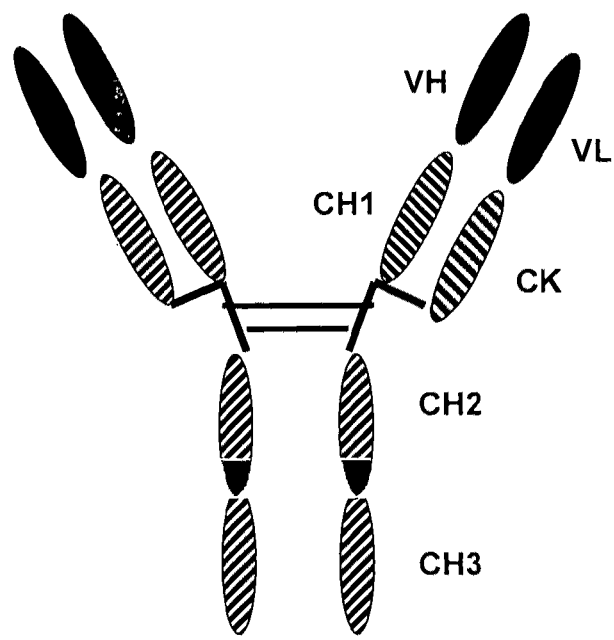
FIG. 7A is a schematic representation of chimeric IgG1 15C1 containing the mouse IgG1 CH2 domain residues 319 to 340. The mouse variable and constant domains of the light and heavy chain are in black. The human constant domains of the light and heavy chains are in hatched black. Chimeric IgG1 15C1 is a recombinant immunoglobulin consisting of the mouse heavy and light chain variable regions of 15C1 in fusion with human IgG1 heavy and Kappa light constant regions. V=variable domain; L=light chain; H=heavy chain; CK=Kappa constant domain of the light chain; CH1, CH2, CH3=constant domains of the heavy chain.
Figure 7B:
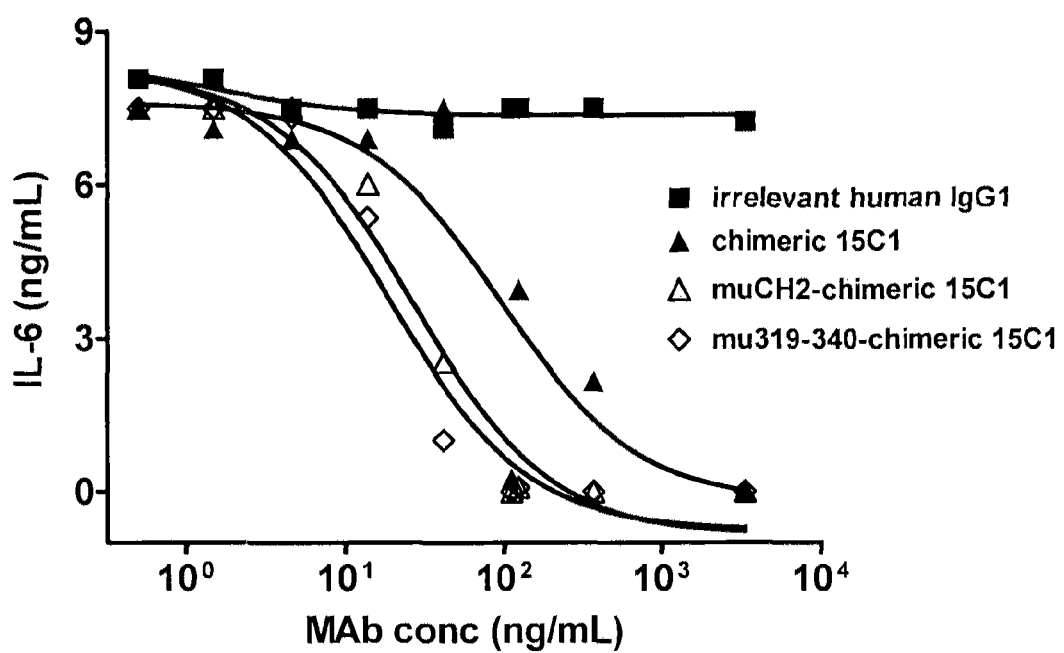
FIG. 7B is a graph depicting LPS-dependent IL-6 production in a human whole blood assay by chimeric IgG1 15C1 or chimeric IgG1 15C1 containing either the full length or mutant 319-340 mouse CH2 domain.

In the human whole blood assay, it was found that the recombinant version containing the mouse CH2 domain had a similar inhibitory activity to that of the fully mouse IgG1 15C1 IgG1. On the other hand, the recombinant version containing the human CH2 was not as potent as the fully mouse IgG1 15C1 IgG1, but had an activity reduced to that of the chimeric IgG1 15C1 (FIG. 5B). From these data, it was concluded that the Fc-mediated inhibitory contribution is restricted to the CH2 domain of the heavy chain of mouse IgG1.

Figure 8C:
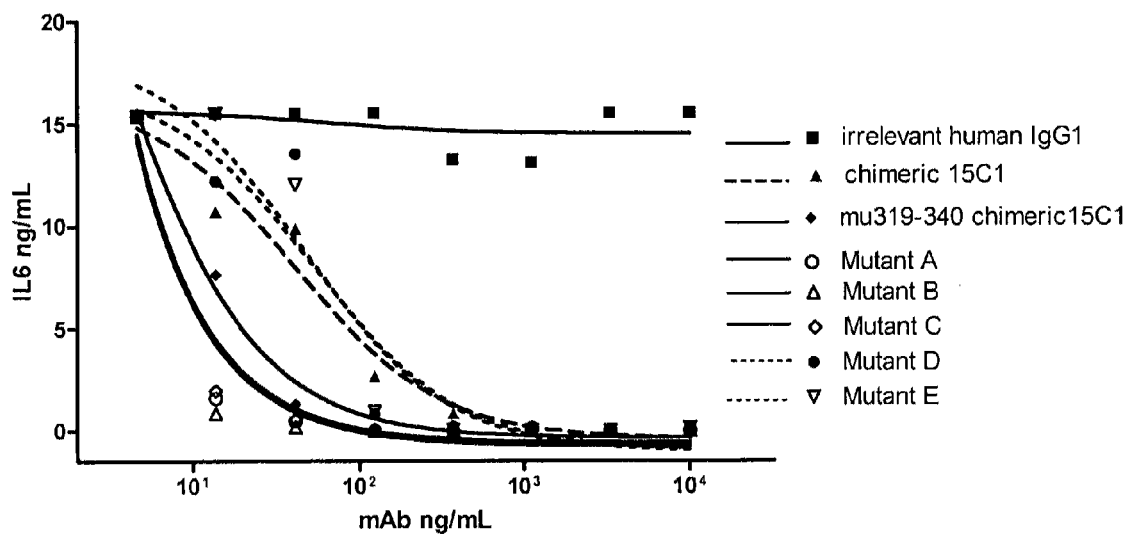
FIG. 8C is a graph depicting LPS-dependent IL-6 production in human whole blood assay by the chimeric IgG1 15C1, chimeric IgG1 15C1 containing either the full length or mutants 319-340 mouse CH2.

Studies were then designed to evaluate which residues of the mouse CH2 domain are necessary for Fc-mediated inhibitory activity. Starting with the chimeric IgG115C1 containing the full length mouse CH2 domain, the approach was to identify the critical region of the CH2 domain by introducing a maximum number of human residues without observing a loss of the Fc-mediated inhibitory activity. The identification of these critical residues was determined by subdividing the mouse CH2 into 4 parts (A: EU positions 231 to 261; B: EU positions 319 to 340; C: EU positions 296-318 and D: EU positions 262 to 295) and introducing for each of the 4 subregions the corresponding CH2 amino acid sequence of a human IgG1 (see FIG. 6A). The sub-division of the mouse CH2 into four subregions was purely based on amino acid sequence homology with the human CH2. The four heavy chain mutants were engineered by overlapping PCR and recombinant MAbs expressed in PEAK. The corresponding antibodies were purified from transfected-cell supernatants by protein G affinity column chromatography and binding to CHO stable cell line expressing human TLR4-MD2 complex on their surface of the following antibodies was determined: muCH2-chimeric IgG1 15C1; chimeric IgG1 15C1; A mu 231-261 CH2 chimeric IgG1 15C1; B mu 319-340 CH2 chimeric IgG1 15C1; C mu 296-318 CH2 chimeric IgG1 15C1; and D mu 262-295 CH2 chimeric IgG1 15C1. $4\times10^5$ cells/well were incubated for 30 minutes at 4° C. in 50 μl of phosphate buffered saline (PBS) with 1% bovine serum albumin (PBS-1% BSA) and either serial dilution of the appropriate antibody or an irrelevant human IgG1 isotype control. Cells were washed once with PBS-1% BSA and incubated in the same buffer with FMAT-Blue®-conjugated goat anti-human Kappa light chain antibody (1:250 dilution, Sigma K3502) for 30 minutes at 4° C. Cells were washed twice with PBS-1% BSA and analyzed using a FACScalibur® flow cytometer (Applied Biosystems) in the FL-4 channel.

Equivalent binding to TLR4/MD2 was demonstrated by FACS analysis (see FIG. 6B). The neutralizing capability of these antibodies was then evaluated using the human whole blood assay. Fresh heparinated blood from healthy volunteers was obtained by venipuncture and diluted 1:2 with RPMI 1640. The diluted blood was plated at 60 μl/well in a 96-well plate and incubated for 15 minutes at 37° C. Then 30 μl of serial dilutions in RPMI 1640 of mutants chimeric IgG1 15C1 containing different sub-regions of mouse CH2 MAbs were added to the blood and incubated for an hour at 37° C. Blood cells were then stimulated by adding 30 μl of *E. coli* K12 LPS (2 ng/ml final in RPMI 1640 containing 0.1% HSA) to the wells and incubated for 6 hours. IL-6 production was then measured by ELISA.

In a human whole blood assay (FIG. 6C), the inhibitory activity of the antibody containing the mouse CH2 domain was found to be drastically reduced when the human IgG1 amino acid residues at EU positions 319 to 340 (mutant B) were introduced. It was concluded from this set of mutants that the inhibitory activity within the mouse CH2 domain is predominantly restricted to the amino acid sequence containing the mouse IgG1 residues at EU positions 319 to 340.

Studies were then designed to determine the effect of grafting of mouse IgG1 CH2 amino acid residues at positions 319 to 340 into the human CH2 domain of the chimeric IgG1 15C1 antibody. The residues at EU positions 319 to 340 of the mouse IgG1 CH2 were introduced within the CH2 of the chimeric IgG1 15C1 by overlapping PCR (see FIG. 7A). The mutant MAb was expressed in PEAK cells and purified from transfected-cell supernatants by protein G affinity column chromatography. The neutralizing capability of chimeric IgG1 15C1, muCH2-chimeric IgG1 15C1 and mu319-340 chimeric IgG1 15C1 antibodies was evaluated using the human whole blood assay. Fresh heparinated blood from healthy volunteers was obtained by venipuncture and diluted 1:2 with RPMI 1640. The diluted blood was plated at 60 in a 96-well plate and incubated for 15 minutes at 37° C. Then 30 μl of serial dilutions in RPMI 1640 of the chimeric IgG1 15C1 and chimeric IgG1 15C1 containing either full length mouse CH2 or mouse CH2 residue 319 to 340 (EU numbering) MAbs were added to the blood and incubated for an hour at 37° C. Blood cells were then stimulated by adding 30 μl of *E. coli* K12 LPS (2 ng/ml final in RPMI 1640 containing 0.1% HSA) to the wells and incubated for 6 hours. IL-6 production was then measured by ELISA.

In a human whole blood assay (FIG. 7B), the inhibitory activity of the antibody containing the mouse CH2 amino acid residues at EU positions 319 to 340 was increased to a level similar to that of 15C1 antibodies containing the full length mouse CH2 domain. It was concluded that grafting into the human CH2 of a stretch of 22 mouse IgG1 amino acid residues (EU positions 319 to 340) was sufficient to regain full inhibitory activity to a level equivalent to that seen with the whole mouse IgG115C1.

Studies were then designed to determine the minimum number of residues within the mouse IgG1, EU positions 319 to 340, CH2 domain that are necessary and sufficient to maintain the overall inhibitory activity of the mouse IgG1 Fc.

From the alignment of the amino acid sequence of amino acid residues at positions 319 to 340 between the mouse and human IgG1, 7 differences were seen (numbered 1 to 7 in FIG. 8A). In order to determine amongst these 7 residues those which are critical for maintaining the biological activity, the effect of exchanging the residues of mouse IgG1 with those of human IgG1 was examined. To this end, starting from chimeric IgG1 15C1 containing the mouse CH2 region EU position 319 to 340, a set of 5 mutants were engineered using the QuickChange mutagenesis protocol from Stratagene (mutants A to E in FIG. 8B). The 5 mutants MAbs were expressed in PEAK and purified from transfected-cell supernatants by protein G affinity column chromatography.

The neutralizing capability of the 5 mutant MAbs was evaluated in the human whole blood assay. Fresh heparinated Studies were then designed to determine the minimum number of mouse residues which when grafted into the human CH2 domain of the chimeric IgG1 15C1 antibody at the corresponding EU positions, would regain the inhibitory potency of the native mouse IgG1 15C1 antibody. Having identified within the mouse IgG1 CH2 domain, three amino acid residues, Ser 326, Ala 327 and Phe 329 (EU numbering) as being responsible for the overall inhibitory activity of mouse IgG1 15C1; a new set of mutants were designed in order to introduce within the chimeric IgG1 15C1, all 6 possible combinatorial combinations between mouse and human sequences at these three EU positions. The sequences of the new mutants, F, G and H, together with the sequences of mutant C, D and E (described previously in FIG. 8B) are shown below in Table 1.

TABLE 1

Amino acid sequences of the 6 mutants (C to H) at EU positions 325 to 328 within the CH2 domain of chimeric IgG1 15C1.

| chimeric IgG1 15C1 mutants | mutations from human to mouse amino acid residue at defined EU positions | number of mouse residues left overall in human CH2 | amino acid residues at EU positions 325 to 328 | SEQ ID NO: |
|---|---|---|---|---|
| human | | | NKAL | 97 |
| # H | L 328 F | 1 | NKAF | 89 |
| # E | K 326 A | 1 | NAAL | 98 |
| # D | N 325 S; K 326 A | 2 | SAAL | 99 |
| # G | K 326 A; L 328 F | 2 | NAAF | 88 |
| # F | N 325 S; L 328 F | 2 | SKAF | 87 |
| # C | N 325 S; K 326 A; L 328F | 3 | SAAF | 86 |
| mouse | | | SAAF | 86 |

Human residues are in bold.

blood from healthy volunteers was obtained by venipuncture and diluted 1:2 with RPMI 1640. The diluted blood was plated at 60 µl/well in a 96-well plate and incubated for 15 minutes at 37° C. Then 30 µl of serial dilutions in RPMI 1640 of the chimeric IgG1 15C1, chimeric IgG1 15C1 containing mouse CH2 amino acid residues at EU positions 319 to 340 and mutants A to E MAbs were added to the blood and incubated for an hour at 37° C. Blood cells were then stimulated by adding 30 µl of E. coli K12 LPS (2 ng/ml final in RPMI 1640 containing 0.1% HSA) to the wells and incubated for 6 hours. IL-6 production was then measured by ELISA.

In a human whole blood assay (FIG. 8C), the mutants D and E exhibited the same inhibitory activity as chimeric IgG1 15C1 whereas mutants A, B and C showed an inhibitory activity at least as good as that of chimeric IgG1 15C1 containing the mouse CH2 region EU positions 319 to 340. It was concluded from the results of the human whole blood assay and the analysis of the amino acid sequences of the 5 mutants that on one hand, the introduction of the 4 human amino acids residues; Y1 (EU position 319), K2 (EU position 322), S3 (EU position 324) and A7 (EU position 339) (see FIG. 8B) had no deleterious effect on the inhibitory activity of the corresponding antibodies, but on the other hand the introduction of the 2 human amino acid residues N4 (EU position 325) and L6 (EU position 326) had a negative effect with the loss of inhibitory effect due to the Fc portion. Overall, it was concluded that out of the 7 mouse residues potentially responsible for the inhibitory effect of the mouse IgG1 Fc, only three; Ser 4 (EU position 325), Ala 5 (EU position 326) and Phe 6 (EU position 328); appeared to be critical for the overall inhibitory activity of the mouse IgG1 Fc.

The 3 mutants were engineered using the Quick Change mutagenesis protocol from Stratagene, expressed in PEAK cells and purified from transfected-cell supernatants by protein G affinity column chromatography.

The relative binding affinity of these mutant antibodies was determined using a CHO stable cell line expressing human TLR4/MD2 on the cell surface. $4 \times 10^5$ cells/well were incubated for 30 minutes at 4° C. in 50 µl of phosphate buffered saline (PBS) with 1% bovine serum albumin (PBS-1% BSA) and either serial dilution of the appropriate antibody or an irrelevant human IgG1 isotype control. Cells were washed once with PBS-1% BSA and incubated in the same buffer with FMAT-Blue®-conjugated goat anti-human Kappa light chain antibody (1:250 dilution, Sigma K3502) for 30 minutes at 4° C. Cells were washed twice with PBS-1% BSA and analyzed using a FACScalibur® flow cytometer (Applied Biosystems) in the FL-4 channel.

The neutralizing capability of these mutated antibodies was also evaluated using the human whole blood assay. Fresh heparinated blood from healthy volunteers was obtained by venipuncture and diluted 1:2 with RPMI 1640. The diluted blood was plated at 60 µl/well in a 96-well plate and incubated for 15 minutes at 37° C. Then 30 µl of serial dilutions in RPMI 1640 of the chimeric IgG1 15C1, chimeric IgG1 15C1 containing mouse CH2 and mutant C, F and H MAbs were added to the blood and incubated for an hour at 37° C. Blood cells were then stimulated by adding 30 µl of E. coli $K_{12}$ LPS (2 ng/ml final in RPMI 1640 containing 0.1% HSA) to the wells and incubated for 6 hours. IL-6 production was then measured by ELISA.

Figure 9A:
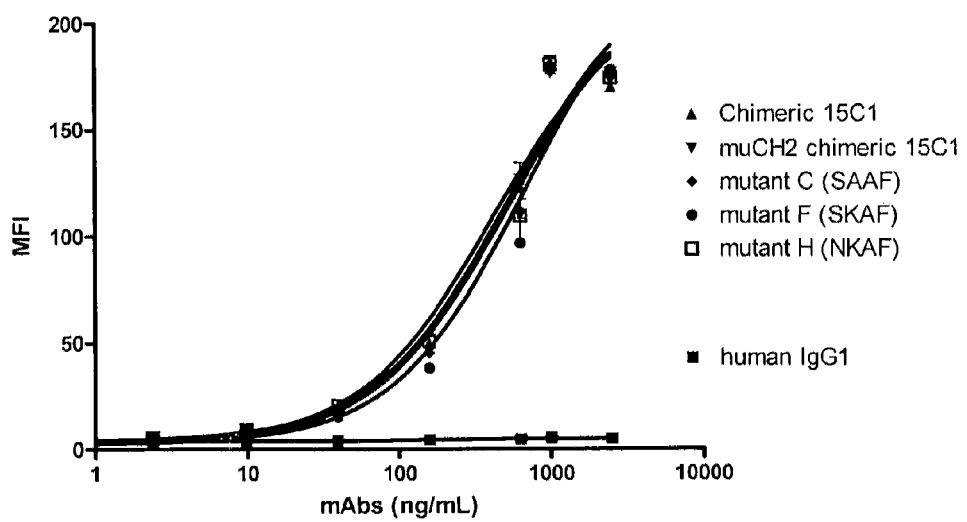
FIG. 9A is a graph depicting binding to CHO stable cell line expressing human TLR4-MD2 on their surface.

By FACS analysis, all the mutants were shown to have a similar relative affinity to the TLR4/MD2 complex expressed on CHO cells (see FIG. 9A) In a human whole blood assay (FIG. 9B), the mutants C and F exhibited an inhibitory activity better than that of chimeric IgG1 15C1 containing the mouse CH2, the mutant C being the more potent of the two. The mutant H was more potent than the chimeric IgG1 15C1 but less potent than chimeric IgG1 15C1 containing the mouse CH2. Mutant D, E and G had an inhibitory activity similar but not better than that of the chimeric IgG1 15C1.

In conclusion, two mutants within the CH2 domain of chimeric IgG1 15C1 which have an inhibitory activity at least as good as that of the native mouse IgG1 15C1 have been identified. These two mutants, C and F, have respectively 3 and 2 amino acid residues mutated to the corresponding mouse residue of an IgG1 CH2 domain at the same EU position. Mutant C which appears to have the strongest inhibitory activity of the two mutants has the following 3 mouse residues Ser, Ala and Phe at EU positions 325, 326 and 328, respectively. Mutant F consists of the same mutations but only at EU positions 325 and 328.

Studies were then designed to evaluate whether the results obtained with chimeric IgG1 15C1 were also valid for the humanized version of 15C1. The humanized version of mouse mAb 15C1, consisting in the heavy chain version 4-28 (15C1 Hu VH version 4-28) paired with the light chain version A26 (15C1 Hu VL version A26) has been constructed by CDR-grafting as described herein and in International Patent application No. PCT/IB2005/004174, the contents of which are hereby incorporated by reference in its entirety. This humanized version, later referred as humanized IgG1 15C1, was previously shown by FACS analysis to have a relative affinity for the TLR4/MD2 complex expressed at the surface of CHO cells similar to that of chimeric IgG1 15C1.

In a first set of experiments the inhibitory activity of the chimeric IgG1 15C1 containing the mouse CH2 (muCH2 chim 15C1) was compared to that of the humanized IgG1 15C1 with the mouse CH2 (muCH2 hum 15C1). These MAbs were expressed in PEAK cells and were purified from transfected-cell supernatants by protein G affinity column chromatography. An equivalent binding to CHO-expressing TLR4/MD2 was demonstrated by FACS analysis.

The neutralizing capability of the muCH2 humanized 15C1 antibody was evaluated using the human whole blood assay. Fresh heparinated blood from healthy volunteers was obtained by venipuncture and diluted 1:2 with RPMI 1640. The diluted blood was plated at 60 µl/well in a 96-well plate and incubated for 15 minutes at 37° C. Then 30 ml of serial dilutions in RPMI 1640 of the mouse IgG1 15C1, chimeric IgG1 15C1, mouse IgG1 15C1 containing mouse CH2 and humanized IgG1 15C1 containing mouse CH2 MAbs were added to the blood and incubated for an hour at 37° C. Blood cells were then stimulated by adding 30 µl of E. coli K12 LPS (2 ng/ml final in RPMI 1640 containing 0.1% HSA) to the wells and incubated for 6 hours. IL-6 production was then measured by ELISA.

Figure 10:
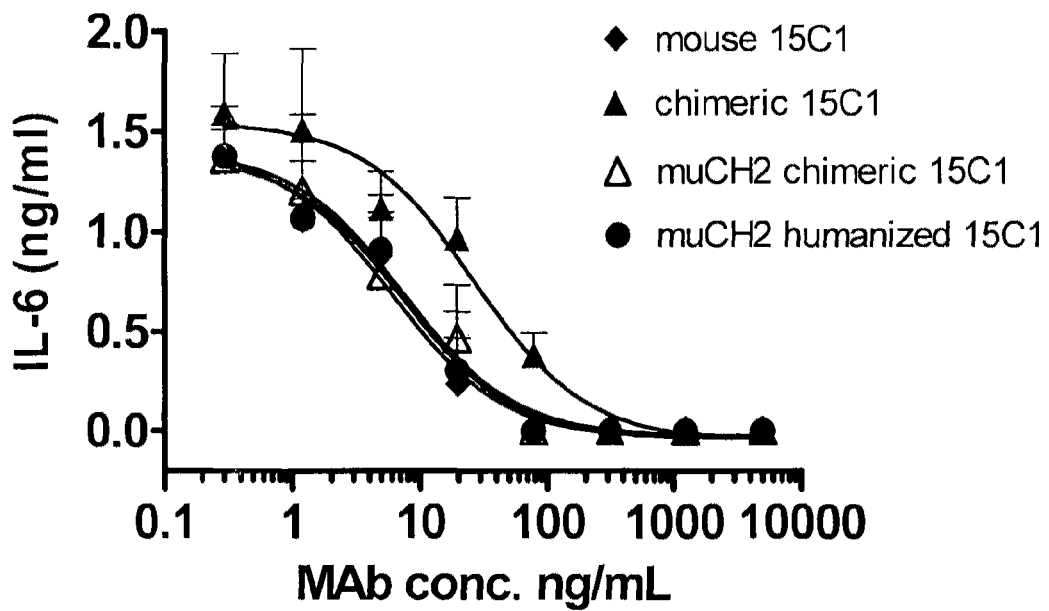
FIG. 10 is a graph depicting LPS-dependent IL-6 production in human whole blood assay by the chimeric IgG1 15C1, mouse IgG1 15C1, chimeric IgG1 15C1 containing mouse CH2 and humanized 15C1 containing mouse CH2.

In a human whole blood assay (FIG. 10), it was found that both the chimeric and humanized versions containing the mouse CH2 domain had a similar inhibitory activity to that of the mouse IgG1 15C1 and that this activity was greater than seen with chimeric IgG1 15C1. It was concluded from these results that as previously seen for the chimeric IgG1 15C1, the inhibitory activity of the humanized IgG1 15C1 MAb can be increased to a similar level as that of the native mouse IgG1 15C1 by the introduction of the mouse CH2 domain in its Fc portion.

Similarly to the work done with chimeric IgG1 15C1, a set of 6 mutants C to H (see Table 1) were constructed based on the use of either the human or mouse amino acid residue at EU positions 325, 326 and 328 within the CH2 domain. The corresponding antibodies were purified from transfected-cell supernatants by protein G affinity column chromatography. The binding affinity of these mutant antibodies was determined using a CHO stable cell line expressing human TLR4/MD2 on the cell surface. $4 \times 10^5$ cells/well were incubated for 30 minutes at 4° C. in 50 µl of phosphate buffered saline (PBS) with 1% bovine serum albumin (PBS-1% BSA) and either serial dilution of the appropriate antibody or an irrelevant human IgG1 isotype control. Cells were washed once with PBS-1% BSA and incubated in the same buffer with FMAT-Blue®-conjugated goat anti-human Kappa light chain antibody (1:250 dilution, Sigma K3502) for 30 minutes at 4° C. Cells were washed twice with PBS-1% BSA and analyzed using a FACScalibur® flow cytometer (Applied Biosystems) in the FL-4 channel.

Figure 11A:
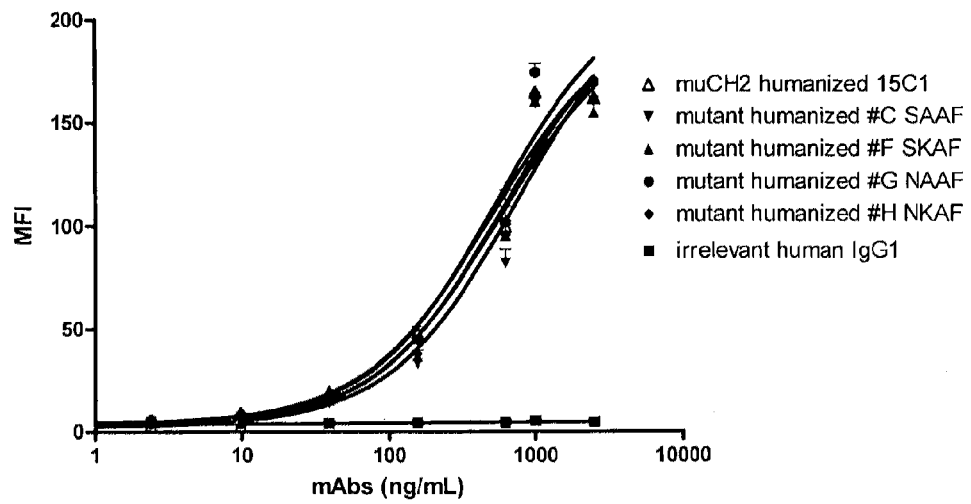
FIG. 11A is a graph depicting Binding to CHO stable cell line expressing human TLR4-MD2 on their surface.

By FACS analysis, all the mutants were shown to have a similar relative affinity to the TLR4/MD2 complex expressed on CHO cells (see FIG. 11A).

The neutralizing capability of the various mutant humanized antibodies was evaluated using the human whole blood assay. Fresh heparinated blood from healthy volunteers was obtained by venipuncture and diluted 1:2 with RPMI 1640. The diluted blood was plated at 60 µl/well in a 96-well plate and incubated for 15 minutes at 37° C. Then 30 µl of serial dilutions in RPMI 1640 of the humanized IgG1 15C1 mutants C, F, G and H and humanized IgG1 15C1 containing the mouse CH2 MAbs were added to the blood and incubated for an hour at 37° C. Blood cells were then stimulated by adding 30 µl of E. coli K12 LPS (2 ng/ml final in RPMI 1640 containing 0.1% HSA) to the wells and incubated for 6 hours. IL-6 production was then measured by ELISA.

Figure 9B:
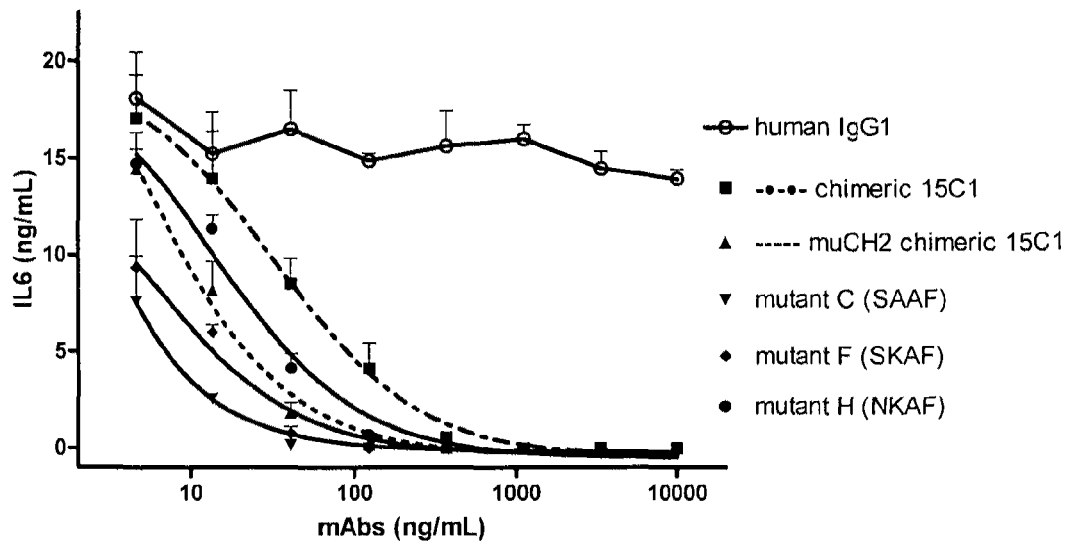
FIG. 9B is a graph depicting LPS-dependent IL-6 production in human whole blood assay by chimeric IgG1 15C1, muCH2 15C1 and mutants chimeric IgG1 15C1 antibodies.
Figure 11B:
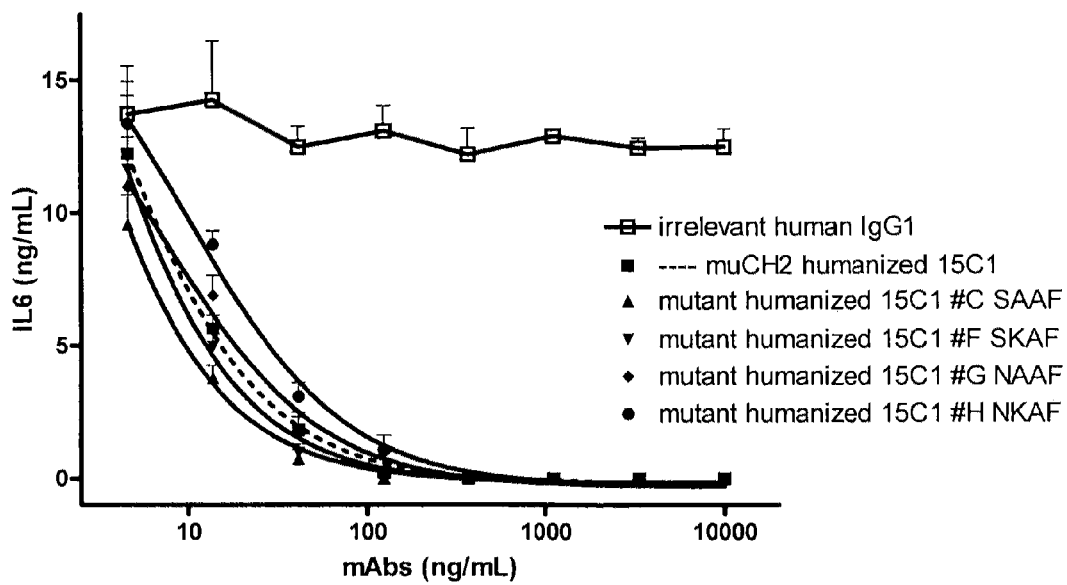
FIG. 11B is a graph depicting LPS-dependent IL-6 production in human whole blood assay by the humanized 15C1 mutants C, F, G and H and humanized 15C1 containing the mouse CH2.

In a human whole blood assay the inhibitory activity of the 6 mutants were compared with that of muCH2 humanized IgG115C1. The results presented in FIG. 11B clearly show that mutant C and F are at least as potent as muCH2 humanized IgG1 15C1 whereas mutants G and H are less efficient. Mutants D and E were also shown to be less efficient than muCH2 humanized IgG1 15C1. The results concord well with those obtained earlier for chimeric IgG1 15C1 (FIG. 9B).

Figure 12:
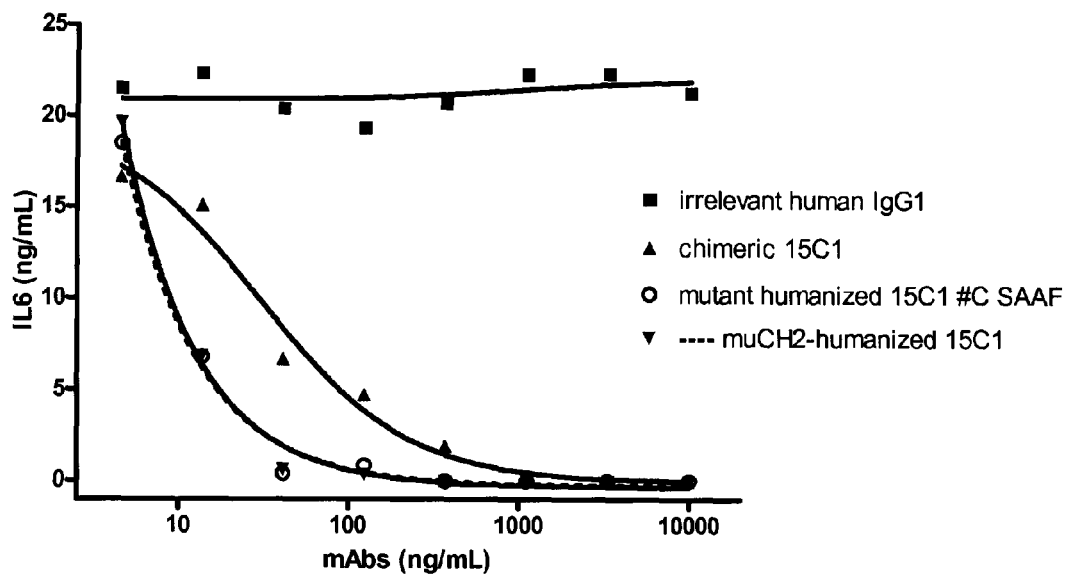
FIG. 12 is a graph depicting LPS-dependent IL-6 production in human whole blood assay by chimeric IgG1 15C1, humanized 15C1 mutant C and humanized 15C1 containing mouse CH2.

Finally, the inhibitory activity of the best humanized CH2 mutant, mutant #C, containing three mouse amino acid residues at EU positions 325 (Ser), 326 (Ala) and 328 (Phe) was tested in a human whole blood assay along with the chimeric IgG1 15C1 and the humanized IgG1 15C1 containing the mouse CH2 domain (muCH2 humanized 15C1). Fresh heparinated blood from healthy volunteers was obtained by venipuncture and diluted 1:2 with RPMI 1640. The diluted blood was plated at 60 Owen in a 96-well plate and incubated for 15 minutes at 37° C. Then 30 µl of serial dilutions in RPMI 1640 of chimeric IgG1 15C1, humanized IgG1 15C1 mutant #C and humanized 15C1 containing mouse CH2 MAbs were added to the blood and incubated for an hour at 37° C. Blood cells were then stimulated by adding 30 µl of E. coli K12 LPS (2 ng/ml final in RPMI 1640 containing 0.1% HSA) to the wells and incubated for 6 hours. IL-6 production was then measured by ELISA. The data presented in FIG. 12 show that mutant #C has an inhibitory activity similar to that of muCH2 humanized IgG1 15C1 and much more potent than that of chimeric IgG1 15C1.

The implication of CD32 in the increase of the inhibitory effect of anti-TLR2, anti-MD2 and anti-CD14 mouse IgG1 monoclonal antibodies as monitored by the inhibition of the pro-inflammatory cytokine IL-6 was evaluated using the human whole blood assay. Fresh heparinated blood from healthy volunteers was obtained by venipuncture and diluted 1:2 with RPMI 1640. The diluted blood was plated at 60 μl/well in a 96-well plate and incubated for 15 minutes at 37° C. Then 30 μl of serial dilutions in RPMI 1640 of mouse anti-TLR2 (13A), mouse anti-MD2 (18H10, 13B) and mouse anti-CD14(13C) MAs with or without mouse anti-human CD32 monoclonal antibody (Clone AT10, Catalog number 2125-3210, AbD Serotec) were added to the blood and incubated for an hour at 37° C. Blood cells were then stimulated by adding 30 μl of *E. coli* K12 LPS (2 ng/ml final in RPMI 1640 containing 0.1% HSA) to the wells and incubated for 6 hours. IL-6 production was then measured by ELISA.

Figure 13A:
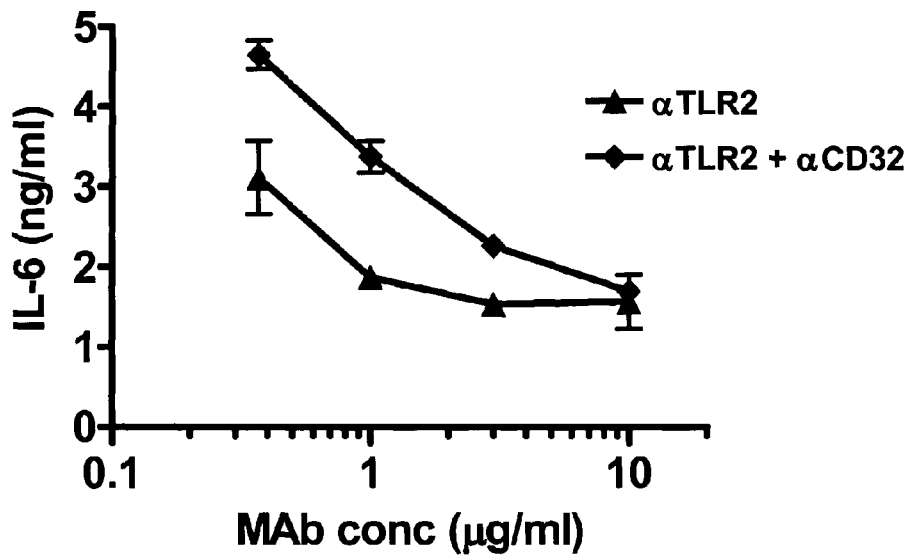
FIGS. 13A-13C are a series of graphs depicting LPS-dependent IL-6 production in human whole blood assay by mouse anti-TLR2 (13A), mouse anti-MD2 (18H10, 13B) and mouse anti-CD14 (13C) MAs with or without mouse anti-human CD32 monoclonal antibody.
Figure 13B:
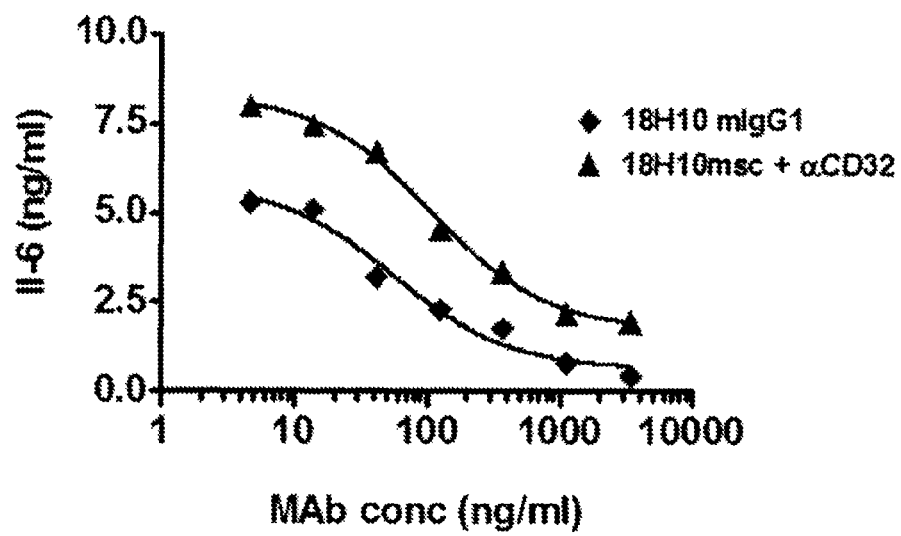
Figure 13C:
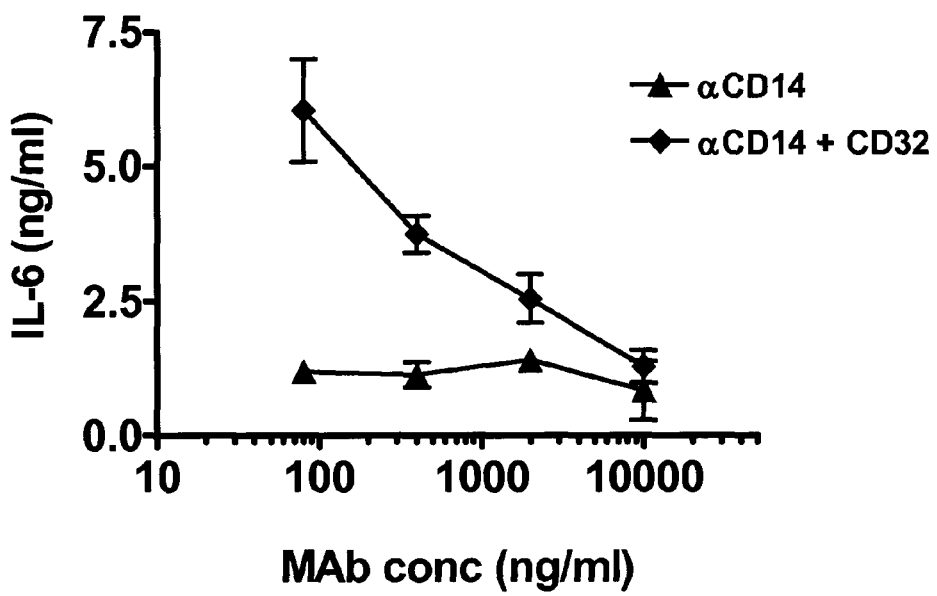

The results shown in FIGS. 13A-13C tend to demonstrate the involvement of interactions between the MAb Fc portion and human FcγRIIA in a putative inhibitory response in other systems than the TLR4i.e, TLR2, MD2 and CD14.

The alignment of the CH2 domain of all human, mouse and rat IgG isotypes in FIG. 16, shows that apart from mouse IgG1, rat IgG2a also contains an SAAF motif (SEQ ID NO: 86) at EU positions 325-328 whereas rat IgG1 contains a very homologous SGAF sequence (SEQ ID NO: 100) at the same EU positions. None of the other human, mouse or rat IgG isotypes contain this SAAF motif (SEQ ID NO: 86). The EU numbering (Edelman, G. M. et al., 1969, Proc. Natl Acad. Sci. USA 63, 78-85) for the gamma chains of the CH2 domain starts at 231 and ends at 340. The human IgG1, IgG3 and IgG4, the mouse IgG2ab, IgG2aa, IgG2b and IgG3, and the rat IgG2b CH2 exons encode 110 amino acids. The human IgG2 and rat IgG2c CH2 exon encode 109 amino acids due to a three nucleotide (nt) deletion. The mouse IgG1, rat IgG1 and IgG2a CH2 exon encode 107 amino acids due to a nine nt deletion.

Example 4

CDR3 Mutated Neutralizing Antibodies

The studies described herein are directed methods of increasing the potency of neutralizing antibodies by modifying one or more residues in the CDR3 portion of an antibody. In particular, the studies described herein use an altered neutralizing antibody that recognizes the TLR4/MD2 complex. These anti-TLR4/MD2 antibodies are modified to include one or more mutations in the CDR3 portion. These antibodies include the following sequences, wherein the single point mutation with the CDR3 region has been underlined within the amino acid sequence:

```
15C1 humanized VH mutant 1 amino acid sequence:
                                            (SEQ ID NO: 66)
QVQLQESGPGLVKPSDTLSLTCAVSGYSITGGYSWHWIRQPPGKGLEWMGYIHYSGYT

DFNPSLKTRITISRDTSKNQFSLKLSSVTAVDTAVYYCARKDPSDAFPYWGQGTLVTVS

S

15C1 humanized VH mutant 1 nucleic acid sequence:
                                            (SEQ ID NO: 67)
CAGGTGCAGCTTCAGGAGTCCGGCCCAGGACTGGTGAAGCCTTCGGACACCCTGTC

CCTCACCTGCGCTGTCTCTGGTTACTCCATCACCGGTGGTTATAGCTGGCACTGGAT

ACGGCAGCCCCCAGGGAAGGGACTGGAGTGGATGGGGTATATCCACTACAGTGGT

TACACTGACTTCAACCCCTCCCTCAAGACTCGAATCACCATATCACGTGACACGTC

CAAGAACCAGTTCTCCCTGAAGCTGAGCTCTGTGACCGCTGTGGACACTGCAGTGT

ATTACTGTGCGAGAAAAGATCCGTCCGACGCCTTTCCTTACTGGGGCCAAGGGACT

CTGGTCACTGTCTCTTCC

15C1 humanized VH mutant 2 amino acid sequence:
                                            (SEQ ID NO: 68)
QVQLQESGPGLVKPSDTLSLTCAVSGYSITGGYSWHWIRQPPGKGLEWMGYIHYSGYT

DFNPSLKTRITISRDTSKNQFSLKLSSVTAVDTAVYYCARKDPSEGFPYWGQGTLVTVS

S

15C1 humanized VH mutant 2 nucleic acid sequence:
                                            (SEQ ID NO: 69)
CAGGTGCAGCTTCAGGAGTCCGGCCCAGGACTGGTGAAGCCTTCGGACACCCTGTC

CCTCACCTGCGCTGTCTCTGGTTACTCCATCACCGGTGGTTATAGCTGGCACTGGAT

ACGGCAGCCCCCAGGGAAGGGACTGGAGTGGATGGGGTATATCCACTACAGTGGT

TACACTGACTTCAACCCCTCCCTCAAGACTCGAATCACCATATCACGTGACACGTC

CAAGAACCAGTTCTCCCTGAAGCTGAGCTCTGTGACCGCTGTGGACACTGCAGTGT

ATTACTGTGCGAGAAAAGATCCGTCCGAGGGATTTCCTTACTGGGGCCAAGGGACT

CTGGTCACTGTCTCTTCC
```

As compared to the reference humanized 4-28 15C1 VH sequence:

15C1 humanized VH 4-28 amino acid sequence:
(SEQ ID NO: 45)
QVQLQESGPGLVKPSDTLSLTCAVSGYSITGGYSWHWIRQPPGKGLEWMGYIHYSGYT

DFNPSLKTRITISRDTSKNQFSLKLSSVTAVDTAVYYCARKDPSDGFPYWGQGTLVTVS

S

15C1 humanized VH 4-28 nucleic acid sequence:
(SEQ ID NO: 70)
CAGGTGCAGCTTCAGGAGTCCGGCCCAGGACTGGTGAAGCCTTCGGACACCCTGTC

CCTCACCTGCGCTGTCTCTGGTTACTCCATCACCGGTGGTTATAGCTGGCACTGGAT

ACGGCAGCCCCCAGGGAAGGGACTGGAGTGGATGGGGTATATCCACTACAGTGGT

TACACTGACTTCAACCCCTCCCTCAAGACTCGAATCACCATATCACGTGACACGTC

CAAGAACCAGTTCTCCCTGAAGCTGAGCTCTGTGACCGCTGTGGACACTGCAGTGT

ATTACTGTGCGAGAAAAGATCCGTCCGACGGATTTCCTTACTGGGGCCAAGGGACT

CTGGTCACTGTCTCTTCC

15C1 humanized VL mutant 1 amino acid sequence:
(SEQ ID NO: 71)
EIVLTQSPDFQSVTPKEKVTITCRASQSISDHLHWYQQKPDQSPKLLIKYASHAISGVPS RFSGSGSGTDFTLTINSLEAEDAATYYCQN<u>S</u>HSFPLTFGGGTKVEIK 15C1 humanized VL mutant 1 nucleic acid sequence:
(SEQ ID NO: 72)
GAAATTGTGTTGACGCAGTCTCCAGACTTTCAGTCTGTGACTCCAAAGGAAAAAGT

CACCATCACCTGCAGGGCCAGTCAGAGTATCAGCGACCACTTACACTGGTACCAAC

AGAAACCTGATCAGTCTCCCAAGCTCCTCATCAAATATGCTTCCCATGCCATTTCTG

GGGTCCCATCGAGGTTCAGTGGCAGTGGGTCTGGGACAGACTTCACTCTCACCATC

AATAGCCTAGAGGCTGAAGATGCTGCAACGTATTACTGTCAGAATAGTCACAGTTT

TCCGCTCACTTTCGGCGGAGGGACCAAGGTGGAGATCAAA

15C1 humanized VL mutant 2 amino acid sequence:
(SEQ ID NO: 73)
EIVLTQSPDFQSVTPKEKVTITCRASQSISDHLHWYQQKPDQSPKLLIKYASHAISGVPS RFSGSGSGTDFTLTINSLEAEDAATYYCQQ<u>G</u>HSFPLTFGGGTKVEIK 15C1 humanized VL mutant 2 nucleic acid sequence:
(SEQ ID NO: 74)
GAAATTGTGTTGACGCAGTCTCCAGACTTTCAGTCTGTGACTCCAAAGGAAAAAGT

CACCATCACCTGCAGGGCCAGTCAGAGTATCAGCGACCACTTACACTGGTACCAAC

AGAAACCTGATCAGTCTCCCAAGCTCCTCATCAAATATGCTTCCCATGCCATTTCTG

GGGTCCCATCGAGGTTCAGTGGCAGTGGGTCTGGGACAGACTTCACTCTCACCATC

AATAGCCTAGAGGCTGAAGATGCTGCAACGTATTACTGTCAGCAGGGTCACAGTTT

TCCGCTCACTTTCGGCGGAGGGACCAAGGTGGAGATCAAA

15C1 humanized VL mutant 3 amino acid sequence:
(SEQ ID NO: 75)
EIVLTQSPDFQSVTPKEKVTITCRASQSISDHLHWYQQKPDQSPKLLIKYASHAISGVPS RFSGSGSGTDFTLTINSLEAEDAATYYCQN<u>SS</u>SFPLTFGGGTKVEIK -continued 15C1 humanized VL mutant 3 nucleic acid sequence:
(SEQ ID NO: 76)
GAAATTGTGTTGACGCAGTCTCCAGACTTTCAGTCTGTGACTCCAAAGGAAAAAGT

CACCATCACCTGCAGGGCCAGTCAGAGTATCAGCGACCACTTACACTGGTACCAAC

AGAAACCTGATCAGTCTCCCAAGCTCCTCATCAAATATGCTTCCCATGCCATTTCTG

GGGTCCCATCGAGGTTCAGTGGCAGTGGGTCTGGGACAGACTTCACTCTCACCATC

AATAGCCTAGAGGCTGAAGATGCTGCAACGTATTACTGTCAGAATAGTAGTAGTTT

TCCGCTCACTTTCGGCGGAGGGACCAAGGTGGAGATCAAA

15C1 humanized VL mutant 4 amino acid sequence:
(SEQ ID NO: 77)
EIVLTQSPDFQSVTPKEKVTITCRASQSISDHLHWYQQKPDQSPKLLIKYASHAISGVPS

RFSGSGSGTDFTLTINSLEAEDAATYYCQQSHSFPLTFGGGTKVEIK

15C1 humanized VL mutant 4 nucleic acid sequence:
(SEQ ID NO: 78)
GAAATTGTGTTGACGCAGTCTCCAGACTTTCAGTCTGTGACTCCAAAGGAAAAAGT

CACCATCACCTGCAGGGCCAGTCAGAGTATCAGCGACCACTTACACTGGTACCAAC

AGAAACCTGATCAGTCTCCCAAGCTCCTCATCAAATATGCTTCCCATGCCATTTCTG

GGGTCCCATCGAGGTTCAGTGGCAGTGGGTCTGGGACAGACTTCACTCTCACCATC

AATAGCCTAGAGGCTGAAGATGCTGCAACGTATTACTGTCAGCAGAGTCACAGTTT

TCCGCTCACTTTCGGCGGAGGGACCAAGGTGGAGATCAAA

As compared to the reference 15C1 humanized VL A26:

15C1 humanized VL A26 amino acid sequence:
(SEQ ID NO 48)
EIVLTQSPDFQSVTPKEKVTITCRASQSISDHLHWYQQKPDQSPKLLIKYASHAISGVPS

RFSGSGSGTDFTLTINSLEAEDAATYYCQNGHSFPLTFGGGTKVEIK

15C1 humanized VL A26 nucleic acid sequence:
(SEQ ID NO: 79)
GAAATTGTGTTGACGCAGTCTCCAGACTTTCAGTCTGTGACTCCAAAGGAAAAAGT

CACCATCACCTGCAGGGCCAGTCAGAGTATCAGCGACCACTTACACTGGTACCAAC

AGAAACCTGATCAGTCTCCCAAGCTCCTCATCAAATATGCTTCCCATGCCATTTCTG

GGGTCCCATCGAGGTTCAGTGGCAGTGGGTCTGGGACAGACTTCACTCTCACCATC

AATAGCCTAGAGGCTGAAGATGCTGCAACGTATTACTGTCAGAATGGTCACAGTTT

TCCGCTCACTTTCGGCGGAGGGACCAAGGTGGAGATCAAA

The binding of these mutants was analyzed by FACS on cells expressing recombinant human TLR4-MD2. PEAK cells were co-transfected with 1 ug of combinations of expression vectors encoding 15C1 humanized VH mutant 1 or 2 together with 15C1 humanized VL A26 or 15C1 humanized VH 4-28 together with 15C1 humanized VL mutant 1, 2, 3 or 4 shown in Example 4 using the Trans IT-LT1 transfection reagent (Mirus Bio Corporation, Madison Wis.). All transfections were carried out in duplicates. 72 h post-transfection, PEAK cells supernatants were collected and the concentration of recombinant human IgG1/Kappa measured by ELISA. The antibody concentrations of all the supernatants were then adjusted to 0.33 μg/ml. These supernatants and two serial dilutions of 0.11 and 0.04 ug/ml were then tested for binding to CHO cells expressing human TLR4-MD2 at their surface by FACS. 5×10$^5$ cells were incubated with the diluted PEAK supernatant for 1 h at 4° C. Following two washes, cells were incubated with secondary antibody (allophycocyanin-conjugated goat anti-human IgG antibody (1:200 dilution; Molecular Probes). Cells were analyzed using a FACS-Calibur flow cytometer (BD Biosciences) in the FL-4 channel (FIGS. 17A-17G). The binding of the humanized mutant versions of 15C1 to TLR4 in FIGS. 17A-17G is expressed as the mean fluorescence intensity for the different antibody concentrations. One representative experiment of four. Error bars show ±S.D. The version VH mutant 1 and VL mutant 2 appear to have a higher MFI than the patented humanized version indicating that these two versions have a higher relative affinity than the humanized version.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An altered antibody or antigen-binding fragment thereof that binds to soluble TLR4, the TLR4/MD2 complex, or both soluble TLR4 and the TLR4/MD2 complex, the antibody or antigen-binding fragment thereof comprising:
   (i) a variable heavy chain region comprising a heavy chain CDR1 region comprising the amino acid sequence GGYSWH (SEQ ID NO: 23), a heavy chain CDR2 region comprising the amino acid sequence YIHYS-GYTDFNPSLKT (SEQ ID NO: 24), and a heavy chain CDR3 region comprising the amino acid sequence of KDPSDAFPY (SEQ ID NO: 80);
   (ii) a variable light chain region comprising a light chain CDR1 region comprising the amino acid sequence RASQSISDHLH (SEQ ID NO:28), a light chain CDR2 region comprising the amino acid sequence YASHAIS (SEQ ID NO:29), and a light chain CDR3 comprising the amino acid sequence of QQGHSFPLT (SEQ ID NO: 83); and
   (iii) an Fc region comprising two mutations compared to a starting antibody, and
   wherein one mutation is a substitution with serine at EU amino acid position 325, and one mutation is a substitution with phenylalanine at EU amino acid position 328.

2. The altered antibody of claim 1, wherein the altered antibody elicits a modified Fc gamma receptor activity.

3. The antibody polypeptide of claim 1, wherein the Fc region is from a mouse, rat or human antibody.

4. The altered antibody of claim 2, wherein the modified Fc gamma receptor activity is the inhibition of the release of proinflammatory mediators.

5. The altered antibody of claim 2, wherein said Fc gamma receptor is the human CD32A.

6. The altered antibody of claim 1, wherein said antibody is human IgG1 isotype, human IgG2 isotype, human IgG3 isotype or human IgG4 isotype.

7. The altered antibody of claim 1, wherein said antibody further comprises a variable heavy chain region comprising the amino acid sequence of SEQ ID NO: 66 and a variable light chain region comprising the amino acid sequence of SEQ ID NO: 73.

* * * * *

SEQUENCE LISTING

<160> NUMBER OF SEQ ID NOS: 100

<210> SEQ ID NO 1
<211> LENGTH: 360
<212> TYPE: DNA
<213> ORGANISM: Artificial Sequence
<220> FEATURE:
<223> OTHER INFORMATION: chemically synthesized

<400> SEQUENCE: 1

```
caggtgcaac tgcagcagtc tggggctgat cttgtgaggc caggggcctt agtcaagttg      60
tcctgcacag cttctggctt caacattaaa gactcctata tacactgggt gaagaagagg     120
cctgaatggg gcctggagtg gattggatgg actgatcctg agaatgttaa ttctatatat     180
gacccgaggt ttcagggcaa ggccagtata acagcagaca catcctccaa cacagccttc     240
cttcagctca ccagcctgac atctgaggac actgccgtct attactgtgc tagggggttat     300 aacggtgttt actatgctat ggactactgg ggccaaggga cctcagtcac cgtctcctca     360
```

<210> SEQ ID NO 2
<211> LENGTH: 120
<212> TYPE: PRT
<213> ORGANISM: Artificial Sequence
<220> FEATURE:
<223> OTHER INFORMATION: chemically synthesized

<400> SEQUENCE: 2

```
Gln Val Gln Leu Gln Gln Ser Gly Ala Asp Leu Val Arg Pro Gly Ala
1               5                   10                  15

Leu Val Lys Leu Ser Cys Thr Ala Ser Gly Phe Asn Ile Lys Asp Ser
            20                  25                  30

Tyr Ile His Trp Val Lys Lys Arg Pro Glu Trp Gly Leu Glu Trp Ile
        35                  40                  45

Gly Trp Thr Asp Pro Glu Asn Val Asn Ser Ile Tyr Asp Pro Arg Phe
    50                  55                  60

Gln Gly Lys Ala Ser Ile Thr Ala Asp Thr Ser Ser Asn Thr Ala Phe
65                  70                  75                  80

Leu Gln Leu Thr Ser Leu Thr Ser Glu Asp Thr Ala Val Tyr Tyr Cys
                85                  90                  95

Ala Arg Gly Tyr Asn Gly Val Tyr Tyr Ala Met Asp Tyr Trp Gly Gln
            100                 105                 110

Gly Thr Ser Val Thr Val Ser Ser
        115                 120
```

<210> SEQ ID NO 3
<211> LENGTH: 5
<212> TYPE: PRT
<213> ORGANISM: Artificial Sequence
<220> FEATURE:
<223> OTHER INFORMATION: chemically synthesized

<400> SEQUENCE: 3

```
Asp Ser Tyr Ile His
1               5
```

<210> SEQ ID NO 4
<211> LENGTH: 17
<212> TYPE: PRT
<213> ORGANISM: Artificial Sequence
<220> FEATURE:
<223> OTHER INFORMATION: chemically synthesized -continued

```
<400> SEQUENCE: 4

Trp Thr Asp Pro Glu Asn Val Asn Ser Ile Tyr Asp Pro Arg Phe Gln
1               5                   10                  15

Gly

<210> SEQ ID NO 5
<211> LENGTH: 11
<212> TYPE: PRT
<213> ORGANISM: Artificial Sequence
<220> FEATURE:
<223> OTHER INFORMATION: chemically synthesized

<400> SEQUENCE: 5

Gly Tyr Asn Gly Val Tyr Tyr Ala Met Asp Tyr
1               5                   10

<210> SEQ ID NO 6
<211> LENGTH: 321
<212> TYPE: DNA
<213> ORGANISM: Artificial Sequence
<220> FEATURE:
<223> OTHER INFORMATION: chemically synthesized

<400> SEQUENCE: 6
caaattgttc tcacccagtc tccatcaatc atgtctgcgt ctctagggga ggagatcacc    60
ctaacctgca gtgccagctc gagtgtaatt tacatgcact ggtaccagca gaagtcaggc   120
acttctccca aactcttgat ttataggaca caacctggg cttctggagt cccttctcgc    180
ttcagtggca gtgggtctgg gacctttat tctctcacaa tcagcagtgt ggaggctgaa    240
gatgctgccg attattactg ccatcagtgg agtagttttc cgtacacgtt cggaggggg    300 accaagctgg aaatcaaacg g                                              321

<210> SEQ ID NO 7
<211> LENGTH: 107
<212> TYPE: PRT
<213> ORGANISM: Artificial Sequence
<220> FEATURE:
<223> OTHER INFORMATION: chemically synthesized

<400> SEQUENCE: 7

Gln Ile Val Leu Thr Gln Ser Pro Ser Ile Met Ser Ala Ser Leu Gly
1               5                   10                  15

Glu Glu Ile Thr Leu Thr Cys Ser Ala Ser Ser Ser Val Ile Tyr Met
                20                  25                  30

His Trp Tyr Gln Gln Lys Ser Gly Thr Ser Pro Lys Leu Leu Ile Tyr
            35                  40                  45

Arg Thr Tyr Asn Leu Ala Ser Gly Val Pro Ser Arg Phe Ser Gly Ser
        50                  55                  60

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Ser Ser Phe Pro Tyr Thr
                85                  90                  95

Phe Gly Gly Gly Thr Lys Leu Glu Ile Lys Arg
                100                 105

<210> SEQ ID NO 8
<211> LENGTH: 10
<212> TYPE: PRT
<213> ORGANISM: Artificial Sequence
<220> FEATURE:
<223> OTHER INFORMATION: chemically synthesized
```

-continued

```
<400> SEQUENCE: 8

Ser Ala Ser Ser Ser Val Ile Tyr Met His
1               5                   10

<210> SEQ ID NO 9
<211> LENGTH: 7
<212> TYPE: PRT
<213> ORGANISM: Artificial Sequence
<220> FEATURE:
<223> OTHER INFORMATION: chemically synthesized

<400> SEQUENCE: 9

Arg Thr Tyr Asn Leu Ala Ser
1               5

<210> SEQ ID NO 10
<211> LENGTH: 9
<212> TYPE: PRT
<213> ORGANISM: Artificial Sequence
<220> FEATURE:
<223> OTHER INFORMATION: chemically synthesized

<400> SEQUENCE: 10

His Gln Trp Ser Ser Phe Pro Tyr Thr
1               5

<210> SEQ ID NO 11
<211> LENGTH: 353
<212> TYPE: DNA
<213> ORGANISM: Artificial Sequence
<220> FEATURE:
<223> OTHER INFORMATION: chemically synthesized

<400> SEQUENCE: 11
aggtgaaact gcaggagtct ggagctgagc tgatgaagcc tggggcctca gtgaagatat      60
cctgcaaggc tactggctac aaattcagtg actactggat agagtggata aaacagaggc     120
ctggacatgg ccttgagtgg attggagaga ttttgcctgg aagtggtagt actaactaca     180
atgaggactt caaggacaag gccacattca cttcagatac atcctccaac acagcctaca     240
tgcaactcag cagcctgaca tctgaagact ctgccgtcta ttactgtgca aagaggaga     300 gggcgtacta ctttggctat tggggccaag ggaccacggt caccgtctcc tca           353

<210> SEQ ID NO 12
<211> LENGTH: 117
<212> TYPE: PRT
<213> ORGANISM: Artificial Sequence
<220> FEATURE:
<223> OTHER INFORMATION: chemically synthesized

<400> SEQUENCE: 12

Val Lys Leu Gln Glu Ser Gly Ala Glu Leu Met Lys Pro Gly Ala Ser
1               5                   10                  15

Val Lys Ile Ser Cys Lys Ala Thr Gly Tyr Lys Phe Ser Asp Tyr Trp
                20                  25                  30

Ile Glu Trp Ile Lys Gln Arg Pro Gly His Gly Leu Glu Trp Ile Gly
            35                  40                  45

Glu Ile Leu Pro Gly Ser Gly Ser Thr Asn Tyr Asn Glu Asp Phe Lys
        50                  55                  60

Asp Lys Ala Thr Phe Thr Ser Asp Thr Ser Ser Asn Thr Ala Tyr Met
65                  70                  75                  80

Gln Leu Ser Ser Leu Thr Ser Glu Asp Ser Ala Val Tyr Tyr Cys Ala
                85                  90                  95
```

-continued

Lys Glu Glu Arg Ala Tyr Tyr Phe Gly Tyr Trp Gly Gln Gly Thr Thr
            100                 105                 110

Val Thr Val Ser Ser
        115

<210> SEQ ID NO 13
<211> LENGTH: 5
<212> TYPE: PRT
<213> ORGANISM: Artificial Sequence
<220> FEATURE:
<223> OTHER INFORMATION: chemically synthesized

<400> SEQUENCE: 13

Asp Tyr Trp Ile Glu
1               5

<210> SEQ ID NO 14
<211> LENGTH: 17
<212> TYPE: PRT
<213> ORGANISM: Artificial Sequence
<220> FEATURE:
<223> OTHER INFORMATION: chemically synthesized

<400> SEQUENCE: 14

Glu Ile Leu Pro Gly Ser Gly Ser Thr Asn Tyr Asn Glu Asp Phe Lys
1               5                   10                  15

Asp

<210> SEQ ID NO 15
<211> LENGTH: 9
<212> TYPE: PRT
<213> ORGANISM: Artificial Sequence
<220> FEATURE:
<223> OTHER INFORMATION: chemically synthesized

<400> SEQUENCE: 15

Glu Glu Arg Ala Tyr Tyr Phe Gly Tyr
1               5

<210> SEQ ID NO 16
<211> LENGTH: 339
<212> TYPE: DNA
<213> ORGANISM: Artificial Sequence
<220> FEATURE:
<223> OTHER INFORMATION: chemically synthesized

<400> SEQUENCE: 16
gatgttttga tgacccaaac tccactctcc ctgcctgtca gtcttggaga tcaagcctcc      60
atctcttgca ggtctagtca gagccttgaa acagtaatg gaaacaccta tttgaactgg     120
tacctccaga aaccaggcca gtctccacag ctcctgatct acagggtttc caaccgattt     180
tctggggtcc tagacaggtt cagtggtagt ggatcaggga cagatttcac actgaaaatc    240
agcagagtgg aggctgagga tttgggagtt tatttctgcc tccaagttac acatgtccct    300
cccacgttcg gtgctgggac caagctggaa ctgaaacgg                           339

<210> SEQ ID NO 17
<211> LENGTH: 113
<212> TYPE: PRT
<213> ORGANISM: Artificial Sequence
<220> FEATURE:
<223> OTHER INFORMATION: chemically synthesized -continued

<400> SEQUENCE: 17

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Leu
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Pro Thr Phe Gly Ala Gly Thr Lys Leu Glu Leu Lys
            100                 105                 110

Arg

<210> SEQ ID NO 18
<211> LENGTH: 16
<212> TYPE: PRT
<213> ORGANISM: Artificial Sequence
<220> FEATURE:
<223> OTHER INFORMATION: chemically synthesized

<400> SEQUENCE: 18

Arg Ser Ser Gln Ser Leu Glu Asn Ser Asn Gly Asn Thr Tyr Leu Asn
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: chemically synthesized

<400> SEQUENCE: 19

Arg Val Ser Asn Arg Phe Ser
1               5

<210> SEQ ID NO 20
<211> LENGTH: 9
<212> TYPE: PRT
<213> ORGANISM: Artificial Sequence
<220> FEATURE:
<223> OTHER INFORMATION: chemically synthesized

<400> SEQUENCE: 20

Leu Gln Val Thr His Val Pro Pro Thr
1               5

<210> SEQ ID NO 21
<211> LENGTH: 354
<212> TYPE: DNA
<213> ORGANISM: Artificial Sequence
<220> FEATURE:
<223> OTHER INFORMATION: chemically synthesized

<400> SEQUENCE: 21
gatgtgcagc ttcaggagtc aggacctgac ctaatacaac cttctcagtc acttttcactc    60 acctgcactg tcactggcta ctccatcacc ggtggttata gctggcactg gatccggcag   120
tttccaggaa acaaactgga atggatgggc tacatccact acagtggtta cactgacttc   180

```
aacccctctc tcaaaactcg aatctctatc actcgagaca catccaagaa ccagttcttc    240
ctgcagttga attctgtgac tactgaagac acagccacat attactgtgc aagaaaagat    300
ccgtccgacg gatttcctta ctggggccaa gggactctgg tcactgtctc tgca          354
```

```
<210> SEQ ID NO 22
<211> LENGTH: 118
<212> TYPE: PRT
<213> ORGANISM: Artificial Sequence
<220> FEATURE:
<223> OTHER INFORMATION: chemically synthesized

<400> SEQUENCE: 22
```

Asp Val Gln Leu Gln Glu Ser Gly Pro Asp Leu Ile Gln Pro Ser Gln
1               5                   10                  15

Ser Leu Ser Leu Thr Cys Thr Val Thr Gly Tyr Ser Ile Thr Gly Gly
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Lys Asp Pro Ser Asp Gly Phe Pro Tyr Trp Gly Gln Gly Thr
            100                 105                 110

Leu Val Thr Val Ser Ala
        115

```
<210> SEQ ID NO 23
<211> LENGTH: 6
<212> TYPE: PRT
<213> ORGANISM: Artificial Sequence
<220> FEATURE:
<223> OTHER INFORMATION: chemically synthesized

<400> SEQUENCE: 23
```

Gly Gly Tyr Ser Trp His
1               5

```
<210> SEQ ID NO 24
<211> LENGTH: 16
<212> TYPE: PRT
<213> ORGANISM: Artificial Sequence
<220> FEATURE:
<223> OTHER INFORMATION: chemically synthesized

<400> SEQUENCE: 24
```

Tyr Ile His Tyr Ser Gly Tyr Thr Asp Phe Asn Pro Ser Leu Lys Thr
1               5                   10                  15

```
<210> SEQ ID NO 25
<211> LENGTH: 9
<212> TYPE: PRT
<213> ORGANISM: Artificial Sequence
<220> FEATURE:
<223> OTHER INFORMATION: chemically synthesized

<400> SEQUENCE: 25
```

Lys Asp Pro Ser Asp Gly Phe Pro Tyr
1               5

<210> SEQ ID NO 26
<211> LENGTH: 321
<212> TYPE: DNA
<213> ORGANISM: Artificial Sequence
<220> FEATURE:
<223> OTHER INFORMATION: chemically synthesized

<400> SEQUENCE: 26

```
gacattgtga tgacccagtc tccagccacc ctgtctgtga ctccaggtga tagagtctct    60
ctttcctgca gggccagcca gagtatcagc gaccacttac actggtatca acaaaaatca   120
catgagtctc cacggcttct catcaaatat gcttcccatg ccatttctgg gatccctcc    180 aggttcagtg gcagtggatc agggacagat ttcactctca gcatcaaaag tgtggaacct   240
gaagatattg gggtgtatta ctgtcaaaat ggtcacagtt ttccgctcac gttcggtgct   300
gggaccaagc tggagctgaa a                                             321
```

<210> SEQ ID NO 27
<211> LENGTH: 107
<212> TYPE: PRT
<213> ORGANISM: Artificial Sequence
<220> FEATURE:
<223> OTHER INFORMATION: chemically synthesized

<400> SEQUENCE: 27

```
Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp His
            20                  25                  30

Leu His Trp Tyr Gln Gln Lys Ser His Glu Ser Pro Arg Leu Leu Ile
        35                  40                  45

Lys Tyr Ala Ser His Ala Ile Ser Gly Ile Pro Ser Arg Phe Ser Gly
    50                  55                  60

Ser Gly Ser Gly Thr Asp Phe Thr Leu Ser Ile Lys Ser Val Glu Pro
65                  70                  75                  80

Glu Asp Ile Gly Val Tyr Tyr Cys Gln Asn Gly His Ser Phe Pro Leu
                85                  90                  95

Thr Phe Gly Ala Gly Thr Lys Leu Glu Leu Lys
            100                 105
```

<210> SEQ ID NO 28
<211> LENGTH: 11
<212> TYPE: PRT
<213> ORGANISM: Artificial Sequence
<220> FEATURE:
<223> OTHER INFORMATION: chemically synthesized

<400> SEQUENCE: 28

```
Arg Ala Ser Gln Ser Ile Ser Asp His Leu His
1               5                   10
```

<210> SEQ ID NO 29
<211> LENGTH: 7
<212> TYPE: PRT
<213> ORGANISM: Artificial Sequence
<220> FEATURE:
<223> OTHER INFORMATION: chemically synthesized

<400> SEQUENCE: 29

```
Tyr Ala Ser His Ala Ile Ser
1               5
```

<210> SEQ ID NO 30

```
<211> LENGTH: 9
<212> TYPE: PRT
<213> ORGANISM: Artificial Sequence
<220> FEATURE:
<223> OTHER INFORMATION: chemically synthesized

<400> SEQUENCE: 30

Gln Asn Gly His Ser Phe Pro Leu Thr
1               5

<210> SEQ ID NO 31
<211> LENGTH: 363
<212> TYPE: DNA
<213> ORGANISM: Artificial Sequence
<220> FEATURE:
<223> OTHER INFORMATION: chemically synthesized

<400> SEQUENCE: 31
caggttactc tgaaagagtc tggccctggg atattgcagc cctcccagac cctcagtctg      60
acttgttctt tctctgggtt ttcactgacc acttataata taggagtagg ctggattcgt     120
cagccttcag ggaagggtct ggagtggctg gcacacattt ggtggaatga taatatttac     180
tataatacag tccttaagag ccgactcaca ttctccaagg atacctccaa caaccaggtt     240
ttcctcaaga tcgccagtgt ggacattgca gatactgcca catattactg tattcgaatg     300
gctgagggaa ggtacgacgc tatggactac tggggtcaag gaacctcagt caccgtctcc     360
tca                                                                   363

<210> SEQ ID NO 32
<211> LENGTH: 121
<212> TYPE: PRT
<213> ORGANISM: Artificial Sequence
<220> FEATURE:
<223> OTHER INFORMATION: chemically synthesized

<400> SEQUENCE: 32

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Thr Thr Tyr
            20                  25                  30

Asn Ile Gly Val Gly Trp Ile Arg Gln Pro Ser Gly Lys Gly Leu Glu
        35                  40                  45

Trp Leu Ala His Ile Trp Trp Asn Asp Asn Ile Tyr Tyr Asn Thr Val
    50                  55                  60

Leu Lys Ser Arg Leu Thr Phe Ser Lys Asp Thr Ser Asn Asn Gln Val
65                  70                  75                  80

Phe Leu Lys Ile Ala Ser Val Asp Ile Ala Asp Thr Ala Thr Tyr Tyr
                85                  90                  95

Cys Ile Arg Met Ala Glu Gly Arg Tyr Asp Ala Met Asp Tyr Trp Gly
            100                 105                 110

Gln Gly Thr Ser Val Thr Val Ser Ser
        115                 120

<210> SEQ ID NO 33
<211> LENGTH: 7
<212> TYPE: PRT
<213> ORGANISM: Artificial Sequence
<220> FEATURE:
<223> OTHER INFORMATION: chemically synthesized

<400> SEQUENCE: 33

Thr Tyr Asn Ile Gly Val Gly
1               5
```

<210> SEQ ID NO 34
<211> LENGTH: 16
<212> TYPE: PRT
<213> ORGANISM: Artificial Sequence
<220> FEATURE:
<223> OTHER INFORMATION: chemically synthesized

<400> SEQUENCE: 34

His Ile Trp Trp Asn Asp Asn Ile Tyr Tyr Asn Thr Val Leu Lys Ser
1               5                   10                  15

<210> SEQ ID NO 35
<211> LENGTH: 11
<212> TYPE: PRT
<213> ORGANISM: Artificial Sequence
<220> FEATURE:
<223> OTHER INFORMATION: chemically synthesized

<400> SEQUENCE: 35

Met Ala Glu Gly Arg Tyr Asp Ala Met Asp Tyr
1               5                   10

<210> SEQ ID NO 36
<211> LENGTH: 324
<212> TYPE: DNA
<213> ORGANISM: Artificial Sequence
<220> FEATURE:
<223> OTHER INFORMATION: chemically synthesized

<400> SEQUENCE: 36

```
gctatccaga tgacacagag tacatcctcc ctgtctgcct ctctgggaga cagagtcacc    60
atcaattgca gggcaagtca ggacatcacc aattatttaa attggtatca gcagaaacca   120
gatggaactg tcagactcct gatctattat acatcaaaat tacactcagg agccccatca   180
aggttcagtg gccgtgggtc tggaacagat tattctctca ccattagtaa cctggagcaa   240
gaggatattg ccacttactt ttgccaacag ggtaatacgt ttccgtggac gttcggtgga   300
ggcaccaaac tggaaatcaa acgt                                          324
```

<210> SEQ ID NO 37
<211> LENGTH: 108
<212> TYPE: PRT
<213> ORGANISM: Artificial Sequence
<220> FEATURE:
<223> OTHER INFORMATION: chemically synthesized

<400> SEQUENCE: 37

Ala Ile Gln Met Thr Gln Ser Thr Ser Ser Leu Ser Ala Ser Leu Gly
1               5                   10                  15

Asp Arg Val Thr Ile Asn Cys Arg Ala Ser Gln Asp Ile Thr Asn Tyr
                20                  25                  30

Leu Asn Trp Tyr Gln Gln Lys Pro Asp Gly Thr Val Arg Leu Leu Ile
            35                  40                  45

Tyr Tyr Thr Ser Lys Leu His Ser Gly Ala Pro Ser Arg Phe Ser Gly
    50                  55                  60

Arg Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Phe Pro Trp
                85                  90                  95

Thr Phe Gly Gly Gly Thr Lys Leu Glu Ile Lys Arg
            100                 105

<210> SEQ ID NO 38
<211> LENGTH: 11
<212> TYPE: PRT
<213> ORGANISM: Artificial Sequence
<220> FEATURE:
<223> OTHER INFORMATION: chemically synthesized

<400> SEQUENCE: 38

Arg Ala Ser Gln Asp Ile Thr Asn Tyr Leu Asn
1               5                   10

<210> SEQ ID NO 39
<211> LENGTH: 7
<212> TYPE: PRT
<213> ORGANISM: Artificial Sequence
<220> FEATURE:
<223> OTHER INFORMATION: chemically synthesized

<400> SEQUENCE: 39

Tyr Thr Ser Lys Leu His Ser
1               5

<210> SEQ ID NO 40
<211> LENGTH: 9
<212> TYPE: PRT
<213> ORGANISM: Artificial Sequence
<220> FEATURE:
<223> OTHER INFORMATION: chemically synthesized

<400> SEQUENCE: 40

Gln Gln Gly Asn Thr Phe Pro Trp Thr
1               5

<210> SEQ ID NO 41
<211> LENGTH: 624
<212> TYPE: DNA
<213> ORGANISM: Homo sapiens

<400> SEQUENCE: 41

```
ggcgggccgc tcccacttcg gcacgagggg cacgaggtaa atcttttctg cttactgaaa      60
aggaagagtc tgatgattag ttactgatcc tctttgcatt tgtaaagctt tggagatatt     120
gaatcatgtt accatttctg ttttttttcca ccctgttttc ttccatattt actgaagctc    180
agaagcagta ttgggtctgc aactcatccg atgcaagtat tcatacacc tactgtgata     240 aaatgcaata cccaatttca attaatgtta acccctgtat agaattgaaa ggatccaaag    300
gattattgca cattttctac attccaagga gagatttaaa gcaattatat ttcaatctct    360
atataactgt caacaccatg aatcttccaa agcgcaaaga agttatttgc cgaggatctg    420
atgacgatta ctcttttttgc agagctctga agggagagac tgtgaataca acaatatcat    480
tctccttcaa gggaataaaa ttttctaagg gaaaatacaa atgtgttgtt gaagctattt    540
ctgggagccc agaagaaatg ctcttttgct tggagtttgt catcctacac caacctaatt    600
caaattagaa taaattgagt attt                                            624
```

<210> SEQ ID NO 42
<211> LENGTH: 160
<212> TYPE: PRT
<213> ORGANISM: Homo sapiens

<400> SEQUENCE: 42

Met Leu Pro Phe Leu Phe Phe Ser Thr Leu Phe Ser Ser Ile Phe Thr
1               5                   10                  15

Glu Ala Gln Lys Gln Tyr Trp Val Cys Asn Ser Ser Asp Ala Ser Ile
            20                  25                  30

Ser Tyr Thr Tyr Cys Asp Lys Met Gln Tyr Pro Ile Ser Ile Asn Val
        35                  40                  45

Asn Pro Cys Ile Glu Leu Lys Gly Ser Lys Gly Leu Leu His Ile Phe
    50                  55                  60

Tyr Ile Pro Arg Arg Asp Leu Lys Gln Leu Tyr Phe Asn Leu Tyr Ile
65                  70                  75                  80

Thr Val Asn Thr Met Asn Leu Pro Lys Arg Lys Glu Val Ile Cys Arg
                85                  90                  95

Gly Ser Asp Asp Asp Tyr Ser Phe Cys Arg Ala Leu Lys Gly Glu Thr
            100                 105                 110

Val Asn Thr Thr Ile Ser Phe Ser Phe Lys Gly Ile Lys Phe Ser Lys
            115                 120                 125

Gly Lys Tyr Lys Cys Val Val Glu Ala Ile Ser Gly Ser Pro Glu Glu
130                 135                 140

Met Leu Phe Cys Leu Glu Phe Val Ile Leu His Gln Pro Asn Ser Asn
145                 150                 155                 160

<210> SEQ ID NO 43
<211> LENGTH: 839
<212> TYPE: PRT
<213> ORGANISM: Homo sapiens

<400> SEQUENCE: 43

Met Met Ser Ala Ser Arg Leu Ala Gly Thr Leu Ile Pro Ala Met Ala
1               5                   10                  15

Phe Leu Ser Cys Val Arg Pro Glu Ser Trp Glu Pro Cys Val Glu Val
            20                  25                  30

Val Pro Asn Ile Thr Tyr Gln Cys Met Glu Leu Asn Phe Tyr Lys Ile
            35                  40                  45

Pro Asp Asn Leu Pro Phe Ser Thr Lys Asn Leu Asp Leu Ser Phe Asn
    50                  55                  60

Pro Leu Arg His Leu Gly Ser Tyr Ser Phe Phe Ser Phe Pro Glu Leu
65                  70                  75                  80

Gln Val Leu Asp Leu Ser Arg Cys Glu Ile Gln Thr Ile Glu Asp Gly
                85                  90                  95

Ala Tyr Gln Ser Leu Ser His Leu Ser Thr Leu Ile Leu Thr Gly Asn
            100                 105                 110

Pro Ile Gln Ser Leu Ala Leu Gly Ala Phe Ser Gly Leu Ser Ser Leu
            115                 120                 125

Gln Lys Leu Val Ala Val Glu Thr Asn Leu Ala Ser Leu Glu Asn Phe
130                 135                 140

Pro Ile Gly His Leu Lys Thr Leu Lys Glu Leu Asn Val Ala His Asn
145                 150                 155                 160

Leu Ile Gln Ser Phe Lys Leu Pro Glu Tyr Phe Ser Asn Leu Thr Asn
                165                 170                 175

Leu Glu His Leu Asp Leu Ser Ser Asn Lys Ile Gln Ser Ile Tyr Cys
            180                 185                 190

Thr Asp Leu Arg Val Leu His Gln Met Pro Leu Leu Asn Leu Ser Leu
            195                 200                 205

Asp Leu Ser Leu Asn Pro Met Asn Phe Ile Gln Pro Gly Ala Phe Lys
210                 215                 220

Glu Ile Arg Leu His Lys Leu Thr Leu Arg Asn Asn Phe Asp Ser Leu
225                 230                 235                 240

-continued

Asn Val Met Lys Thr Cys Ile Gln Gly Leu Ala Gly Leu Glu Val His
            245                 250                 255

Arg Leu Val Leu Gly Glu Phe Arg Asn Glu Gly Asn Leu Glu Lys Phe
            260                 265                 270

Asp Lys Ser Ala Leu Glu Gly Leu Cys Asn Leu Thr Ile Glu Glu Phe
            275                 280                 285

Arg Leu Ala Tyr Leu Asp Tyr Tyr Leu Asp Asp Ile Ile Asp Leu Phe
            290                 295                 300

Asn Cys Leu Thr Asn Val Ser Ser Phe Ser Leu Val Ser Val Thr Ile
305                 310                 315                 320

Glu Arg Val Lys Asp Phe Ser Tyr Asn Phe Gly Trp Gln His Leu Glu
                325                 330                 335

Leu Val Asn Cys Lys Phe Gly Gln Phe Pro Thr Leu Lys Leu Lys Ser
            340                 345                 350

Leu Lys Arg Leu Thr Phe Thr Ser Asn Lys Gly Gly Asn Ala Phe Ser
            355                 360                 365

Glu Val Asp Leu Pro Ser Leu Glu Phe Leu Asp Leu Ser Arg Asn Gly
            370                 375                 380

Leu Ser Phe Lys Gly Cys Cys Ser Gln Ser Asp Phe Gly Thr Thr Ser
385                 390                 395                 400

Leu Lys Tyr Leu Asp Leu Ser Phe Asn Gly Val Ile Thr Met Ser Ser
                405                 410                 415

Asn Phe Leu Gly Leu Glu Gln Leu Glu His Leu Asp Phe Gln His Ser
            420                 425                 430

Asn Leu Lys Gln Met Ser Glu Phe Ser Val Phe Leu Ser Leu Arg Asn
            435                 440                 445

Leu Ile Tyr Leu Asp Ile Ser His Thr His Thr Arg Val Ala Phe Asn
            450                 455                 460

Gly Ile Phe Asn Gly Leu Ser Ser Leu Glu Val Leu Lys Met Ala Gly
465                 470                 475                 480

Asn Ser Phe Gln Glu Asn Phe Leu Pro Asp Ile Phe Thr Glu Leu Arg
                485                 490                 495

Asn Leu Thr Phe Leu Asp Leu Ser Gln Cys Gln Leu Glu Gln Leu Ser
            500                 505                 510

Pro Thr Ala Phe Asn Ser Leu Ser Ser Leu Gln Val Leu Asn Met Ser
            515                 520                 525

His Asn Asn Phe Phe Ser Leu Asp Thr Phe Pro Tyr Lys Cys Leu Asn
530                 535                 540

Ser Leu Gln Val Leu Asp Tyr Ser Leu Asn His Ile Met Thr Ser Lys
545                 550                 555                 560

Lys Gln Glu Leu Gln His Phe Pro Ser Ser Leu Ala Phe Leu Asn Leu
                565                 570                 575

Thr Gln Asn Asp Phe Ala Cys Thr Cys Glu His Gln Ser Phe Leu Gln
            580                 585                 590

Trp Ile Lys Asp Gln Arg Gln Leu Leu Val Glu Val Glu Arg Met Glu
            595                 600                 605

Cys Ala Thr Pro Ser Asp Lys Gln Gly Met Pro Val Leu Ser Leu Asn
610                 615                 620

Ile Thr Cys Gln Met Asn Lys Thr Ile Ile Gly Val Ser Val Leu Ser
625                 630                 635                 640

Val Leu Val Val Ser Val Val Ala Val Leu Val Tyr Lys Phe Tyr Phe
                645                 650                 655

His Leu Met Leu Leu Ala Gly Cys Ile Lys Tyr Gly Arg Gly Glu Asn

```
                        660                 665                 670
Ile Tyr Asp Ala Phe Val Ile Tyr Ser Ser Gln Asp Glu Asp Trp Val
                    675                 680                 685

Arg Asn Glu Leu Val Lys Asn Leu Glu Glu Gly Val Pro Pro Phe Gln
                690                 695                 700

Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
                    725                 730                 735

Val Ser Gln His Phe Ile Gln Ser Arg Trp Cys Ile Phe Glu Tyr Glu
                740                 745                 750

Ile Ala Gln Thr Trp Gln Phe Leu Ser Ser Arg Ala Gly Ile Ile Phe
            755                 760                 765

Ile Val Leu Gln Lys Val Glu Lys Thr Leu Leu Arg Gln Gln Val Glu
        770                 775                 780

Leu Tyr Arg Leu Leu Ser Arg Asn Thr Tyr Leu Glu Trp Glu Asp Ser
785                 790                 795                 800

Val Leu Gly Arg His Ile Phe Trp Arg Arg Leu Arg Lys Ala Leu Leu
                    805                 810                 815

Asp Gly Lys Ser Trp Asn Pro Glu Gly Thr Val Gly Thr Gly Cys Asn
                820                 825                 830

Trp Gln Glu Ala Thr Ser Ile
        835

<210> SEQ ID NO 44
<211> LENGTH: 110
<212> TYPE: PRT
<213> ORGANISM: Homo sapiens

<400> SEQUENCE: 44

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 45
<211> LENGTH: 118
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (30)..(30)
<223> OTHER INFORMATION: Xaa is Thr or Ser
<220> FEATURE:
<221> NAME/KEY: MISC_FEATURE
<222> LOCATION: (49)..(49)
<223> OTHER INFORMATION: Xaa is Ile or Met
<220> FEATURE:
```

<221> NAME/KEY: MISC_FEATURE
<222> LOCATION: (68)..(68)
<223> OTHER INFORMATION: Xaa is Ile or Met
<220> FEATURE:
<221> NAME/KEY: MISC_FEATURE
<222> LOCATION: (70)..(70)
<223> OTHER INFORMATION: Xaa is Met or Ile

<400> SEQUENCE: 45

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Xaa Gly Gly
            20                  25                  30

Tyr Ser Trp His Trp Ile Arg Gln Pro Pro Gly Lys Gly Leu Glu Trp
        35                  40                  45

Xaa Gly Tyr Ile His Tyr Ser Gly Tyr Thr Asp Phe Asn Pro Ser Leu
    50                  55                  60

Lys Thr Arg Xaa Thr Xaa Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Pro Ser Asp Gly Phe Pro Tyr Trp Gly Gln Gly Thr
            100                 105                 110

Leu Val Thr Val Ser Ser
        115

<210> SEQ ID NO 46
<211> LENGTH: 118
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (24)..(24)
<223> OTHER INFORMATION: Xaa is Ala or Val
<220> FEATURE:
<221> NAME/KEY: MISC_FEATURE
<222> LOCATION: (49)..(49)
<223> OTHER INFORMATION: Xaa is Val or Met
<220> FEATURE:
<221> NAME/KEY: MISC_FEATURE
<222> LOCATION: (79)..(79)
<223> OTHER INFORMATION: Xaa is Leu or Phe

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Xaa Ser Gly Tyr Ser Ile Thr Gly Gly
            20                  25                  30

Tyr Ser Trp His Trp Val Arg Gln Ala Pro Gly Lys Gly Leu Glu Trp
        35                  40                  45

Xaa Ser Tyr Ile His Tyr Ser Gly Tyr Thr Asp Phe Asn Pro Ser Leu
    50                  55                  60

Lys Thr Arg Phe Thr Ile Ser Arg Asp Asn Ser Lys Asn Thr Xaa Tyr
65                  70                  75                  80

Leu Gln Met Asn Ser Leu Arg Ala Glu Asp Thr Ala Val Tyr Tyr Cys
                85                  90                  95

Ala Arg Lys Asp Pro Ser Asp Gly Phe Pro Tyr Trp Gly Gln Gly Thr
            100                 105                 110

Leu Val Thr Val Ser Ser
        115

```
<210> SEQ ID NO 47
<211> LENGTH: 107
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (49)..(49)
<223> OTHER INFORMATION: Xaa is Lys or Tyr

<400> SEQUENCE: 47

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asp His
            20                  25                  30

Leu His Trp Tyr Gln Gln Lys Pro Gly Gln Ala Pro Arg Leu Leu Ile
        35                  40                  45

Xaa Tyr Ala Ser His Ala Ile Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gly Gly Thr Lys Val Glu Ile Lys
            100                 105

<210> SEQ ID NO 48
<211> LENGTH: 107
<212> TYPE: PRT
<213> ORGANISM: Artificial Sequence
<220> FEATURE:
<223> OTHER INFORMATION: chemically synthesized

<400> SEQUENCE: 48

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Asn Gly His Ser Phe Pro Leu
                85                  90                  95

Thr Phe Gly Gly Gly Thr Lys Val Glu Ile Lys
            100                 105

<210> SEQ ID NO 49
<211> LENGTH: 120
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (48)..(48)
<223> OTHER INFORMATION: Xaa is Met or Ile
<220> FEATURE:
<221> NAME/KEY: MISC_FEATURE
<222> LOCATION: (74)..(74)
```

```
<223> OTHER INFORMATION: Xaa is Lys or Thr
<220> FEATURE:
<221> NAME/KEY: MISC_FEATURE
<222> LOCATION: (81)..(81)
<223> OTHER INFORMATION: Xaa is Met or Leu

<400> SEQUENCE: 49

Gln Val Gln Leu Val Gln Ser Gly Ala Glu Val Lys Pro Gly Ser
1               5                   10                  15

Ser Val Lys Val Ser Cys Lys Ala Ser Gly Phe Asn Ile Lys Asp Ser
            20                  25                  30

Tyr Ile His Trp Val Arg Gln Ala Pro Gly Gln Gly Leu Glu Trp Xaa
        35                  40                  45

Gly Trp Thr Asp Pro Glu Asn Val Asn Ser Ile Tyr Asp Pro Arg Phe
    50                  55                  60

Gln Gly Arg Val Thr Ile Thr Ala Asp Xaa Ser Thr Ser Thr Ala Tyr
65                  70                  75                  80

Xaa Glu Leu Ser Ser Leu Arg Ser Glu Asp Thr Ala Val Tyr Tyr Cys
            85                  90                  95

Ala Arg Gly Tyr Asn Gly Val Tyr Tyr Ala Met Asp Tyr Trp Gly Gln
        100                 105                 110

Gly Thr Thr Val Thr Val Ser Ser
    115                 120

<210> SEQ ID NO 50
<211> LENGTH: 106
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (70)..(70)
<223> OTHER INFORMATION: Xaa is Phe or Tyr

<400> SEQUENCE: 50

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ile Tyr Met
            20                  25                  30

His Trp Tyr Gln Gln Lys Pro Gly Gln Ala Pro Arg Leu Leu Ile Tyr
        35                  40                  45

Arg Thr Tyr Asn Leu Ala Ser Gly Ile Pro Ala Arg Phe Ser Gly Ser
    50                  55                  60

Gly Ser Gly Thr Asp Xaa Thr Leu Thr Ile Ser Ser Leu Glu Pro Glu
65                  70                  75                  80

Asp Phe Ala Val Tyr Tyr Cys His Gln Trp Ser Ser Phe Pro Tyr Thr
            85                  90                  95

Phe Gly Gln Gly Thr Lys Val Glu Ile Lys
        100                 105

<210> SEQ ID NO 51
<211> LENGTH: 121
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (30)..(30)
<223> OTHER INFORMATION: Xaa is Ser or Thr
<220> FEATURE:
<221> NAME/KEY: MISC_FEATURE
```

```
<222> LOCATION: (71)..(71)
<223> OTHER INFORMATION: Xaa is Ile or Phe
<220> FEATURE:
<221> NAME/KEY: MISC_FEATURE
<222> LOCATION: (98)..(98)
<223> OTHER INFORMATION: Xaa is Ile or Ala

<400> SEQUENCE: 51
```

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Xaa Thr Tyr
            20                  25                  30

Asn Ile Gly Val Gly Trp Ile Arg Gln Pro Pro Gly Lys Ala Leu Glu
        35                  40                  45

Trp Leu Ala His Ile Trp Trp Asn Asp Asn Ile Tyr Tyr Asn Thr Val
50                  55                  60

Leu Lys Ser Arg Leu Thr Xaa Ser Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Xaa Arg Met Ala Glu Gly Arg Tyr Asp Ala Met Asp Tyr Trp Gly
            100                 105                 110

Gln Gly Thr Leu Val Thr Val Ser Ser
            115                 120

```
<210> SEQ ID NO 52
<211> LENGTH: 121
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (24)..(24)
<223> OTHER INFORMATION: Xaa is Phe or Ala
<220> FEATURE:
<221> NAME/KEY: MISC_FEATURE
<222> LOCATION: (50)..(50)
<223> OTHER INFORMATION: Xaa is Val or Leu
<220> FEATURE:
<221> NAME/KEY: MISC_FEATURE
<222> LOCATION: (71)..(71)
<223> OTHER INFORMATION: Xaa is Ile or Phe
<220> FEATURE:
<221> NAME/KEY: MISC_FEATURE
<222> LOCATION: (73)..(73)
<223> OTHER INFORMATION: Xaa is Lys or Arg
<220> FEATURE:
<221> NAME/KEY: MISC_FEATURE
<222> LOCATION: (80)..(80)
<223> OTHER INFORMATION: Xaa is Leu or Val
<220> FEATURE:
<221> NAME/KEY: MISC_FEATURE
<222> LOCATION: (98)..(98)
<223> OTHER INFORMATION: Xaa is Ile or Ala

<400> SEQUENCE: 52
```

Glu Val Gln Leu Val Glu Ser Gly Gly Gly Leu Val Gln Pro Gly Gly
1               5                   10                  15

Ser Leu Arg Leu Ser Cys Ala Xaa Ser Gly Phe Ser Leu Thr Thr Tyr
            20                  25                  30

Asn Ile Gly Val Gly Trp Val Arg Gln Ala Pro Gly Lys Gly Leu Glu
        35                  40                  45

Trp Xaa Ser His Ile Trp Trp Asn Asp Asn Ile Tyr Tyr Asn Thr Val
50                  55                  60

Leu Lys Ser Arg Leu Thr Xaa Ser Xaa Asp Asn Ser Lys Asn Thr Xaa

```
                65                  70                  75                  80
Tyr Leu Gln Met Asn Ser Leu Arg Ala Glu Asp Thr Ala Val Tyr Tyr
                    85                  90                  95

Cys Xaa Arg Met Ala Glu Gly Arg Tyr Asp Ala Met Asp Tyr Trp Gly
            100                 105                 110

Gln Gly Thr Leu Val Thr Val Ser Ser
            115                 120
```

<210> SEQ ID NO 53
<211> LENGTH: 107
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (71)..(71)
<223> OTHER INFORMATION: Xaa is Phe or Tyr
<220> FEATURE:
<221> NAME/KEY: MISC_FEATURE
<222> LOCATION: (87)..(87)
<223> OTHER INFORMATION: Xaa is Tyr or Phe

<400> SEQUENCE: 53

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Xaa Thr Leu Thr Ile Ser Ser Leu Gln Pro
65                  70                  75                  80

Glu Asp Phe Ala Thr Tyr Xaa Cys Gln Gln Gly Asn Thr Phe Pro Trp
                85                  90                  95

Thr Phe Gly Gly Gly Thr Lys Val Glu Ile Lys
            100                 105
```

<210> SEQ ID NO 54
<211> LENGTH: 109
<212> TYPE: PRT
<213> ORGANISM: Homo sapiens

<400> SEQUENCE: 54

```
Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys
            100                 105
```

```
<210> SEQ ID NO 55
<211> LENGTH: 110
<212> TYPE: PRT
<213> ORGANISM: Homo sapiens

<400> SEQUENCE: 55

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110

<210> SEQ ID NO 56
<211> LENGTH: 110
<212> TYPE: PRT
<213> ORGANISM: Homo sapiens

<400> SEQUENCE: 56

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 57
<211> LENGTH: 107
<212> TYPE: PRT
<213> ORGANISM: Mus musculus

<400> SEQUENCE: 57

Val Pro Glu Val Ser Ser Val Phe Ile Phe Pro Pro Lys Pro Lys Asp
1               5                   10                  15

Val Leu Thr Ile Thr Leu Thr Pro Lys Val Thr Cys Val Val Val Asp
            20                  25                  30

Ile Ser Lys Asp Asp Pro Glu Val Gln Phe Ser Trp Phe Val Asp Asp
        35                  40                  45

Val Glu Val His Thr Ala Gln Thr Gln Pro Arg Glu Glu Gln Phe Asn
    50                  55                  60

Ser Thr Phe Arg Ser Val Ser Glu Leu Pro Ile Met His Gln Asp Trp
65                  70                  75                  80
```

-continued

Leu Asn Gly Lys Glu Phe Lys Cys Arg Val Asn Ser Ala Ala Phe Pro
            85                  90                  95

Ala Pro Ile Glu Lys Thr Ile Ser Lys Thr Lys
        100                 105

<210> SEQ ID NO 58
<211> LENGTH: 110
<212> TYPE: PRT
<213> ORGANISM: Mus musculus

<400> SEQUENCE: 58

Ala Pro Asp Leu Leu Gly Gly Pro Ser Val Phe Ile Phe Pro Pro Lys
1               5                   10                  15

Ile Lys Asp Val Leu Met Ile Ser Leu Ser Pro Met Val Thr Cys Val
            20                  25                  30

Val Val Asp Val Ser Glu Asp Pro Asp Val Gln Ile Ser Trp Phe
        35                  40                  45

Val Asn Asn Val Glu Val His Thr Ala Gln Thr Gln Thr His Arg Glu
50                  55                  60

Asp Tyr Asn Ser Thr Leu Arg Val Val Ser Ala Leu Pro Ile Gln His
65                  70                  75                  80

Gln Asp Trp Met Ser Gly Lys Glu Phe Lys Cys Lys Val Asn Asn Arg
            85                  90                  95

Ala Leu Pro Ser Pro Ile Glu Lys Thr Ile Ser Lys Pro Arg
        100                 105                 110

<210> SEQ ID NO 59
<211> LENGTH: 110
<212> TYPE: PRT
<213> ORGANISM: Mus musculus

<400> SEQUENCE: 59

Ala Pro Asn Leu Leu Gly Gly Pro Ser Val Phe Ile Phe Pro Pro Lys
1               5                   10                  15

Ile Lys Asp Val Leu Met Ile Ser Leu Ser Pro Ile Val Thr Cys Val
            20                  25                  30

Val Val Asp Val Ser Glu Asp Asp Pro Asp Val Gln Ile Ser Trp Phe
        35                  40                  45

Val Asn Asn Val Glu Val His Thr Ala Gln Thr Gln Thr His Arg Glu
50                  55                  60

Asp Tyr Asn Ser Thr Leu Arg Val Val Ser Ala Leu Pro Ile Gln His
65                  70                  75                  80

Gln Asp Trp Met Ser Gly Lys Glu Phe Lys Cys Lys Val Asn Asn Lys
            85                  90                  95

Asp Leu Pro Ala Pro Ile Glu Arg Thr Ile Ser Lys Pro Lys
        100                 105                 110

<210> SEQ ID NO 60
<211> LENGTH: 110
<212> TYPE: PRT
<213> ORGANISM: Mus musculus

<400> SEQUENCE: 60

Ala Pro Asn Leu Glu Gly Gly Pro Ser Val Phe Ile Phe Pro Pro Asn
1               5                   10                  15

Ile Lys Asp Val Leu Met Ile Ser Leu Thr Pro Lys Val Thr Cys Val
            20                  25                  30

Val Val Asp Val Ser Glu Asp Asp Pro Asp Val Gln Ile Ser Trp Phe
        35                  40                  45

```
Val Asn Asn Val Glu Val His Thr Ala Gln Thr Gln Thr His Arg Glu
    50                  55                  60

Asp Tyr Asn Ser Thr Ile Arg Val Val Ser Thr Leu Pro Ile Gln His
65                  70                  75                  80

Gln Asp Trp Met Ser Gly Lys Glu Phe Lys Cys Lys Val Asn Asn Lys
                85                  90                  95

Asp Leu Pro Ser Pro Ile Glu Arg Thr Ile Ser Lys Ile Lys
            100                 105                 110

<210> SEQ ID NO 61
<211> LENGTH: 110
<212> TYPE: PRT
<213> ORGANISM: Rattus norvegicus

<400> SEQUENCE: 61

Ala Gly Asn Ile Leu Gly Gly Pro Ser Val Phe Ile Phe Pro Pro Lys
1               5                   10                  15

Pro Lys Asp Ala Leu Met Ile Ser Leu Thr Pro Lys Val Thr Cys Val
            20                  25                  30

Val Val Asp Val Ser Glu Asp Asp Pro Asp Val His Val Ser Trp Phe
        35                  40                  45

Val Asp Asn Lys Glu Val His Thr Ala Trp Thr Gln Pro Arg Glu Ala
    50                  55                  60

Gln Tyr Asn Ser Thr Phe Arg Val Val Ser Ala Leu Pro Ile Gln His
65                  70                  75                  80

Gln Asp Trp Met Arg Gly Lys Glu Phe Lys Cys Lys Val Asn Asn Lys
                85                  90                  95

Ala Leu Pro Ala Pro Ile Glu Arg Thr Ile Ser Lys Pro Lys
            100                 105                 110

<210> SEQ ID NO 62
<211> LENGTH: 107
<212> TYPE: PRT
<213> ORGANISM: Rattus norvegicus

<400> SEQUENCE: 62

Gly Ser Glu Val Ser Ser Val Phe Ile Phe Pro Pro Lys Thr Lys Asp
1               5                   10                  15

Val Leu Thr Ile Thr Leu Thr Pro Lys Val Thr Cys Val Val Val Asp
            20                  25                  30

Ile Ser Gln Asn Asp Pro Glu Val Arg Phe Ser Trp Phe Ile Asp Asp
        35                  40                  45

Val Glu Val His Thr Ala Gln Thr His Ala Pro Glu Lys Gln Ser Asn
    50                  55                  60

Ser Thr Leu Arg Ser Val Ser Glu Leu Pro Ile Val His Arg Asp Trp
65                  70                  75                  80

Leu Asn Gly Lys Thr Phe Lys Cys Lys Val Asn Ser Gly Ala Phe Pro
                85                  90                  95

Ala Pro Ile Glu Lys Ser Ile Ser Lys Pro Glu
            100                 105

<210> SEQ ID NO 63
<211> LENGTH: 107
<212> TYPE: PRT
<213> ORGANISM: Rattus norvegicus

<400> SEQUENCE: 63

Gly Ser Glu Val Ser Ser Val Phe Ile Phe Pro Pro Lys Pro Lys Asp
```

```
                1               5                   10                  15

Val Leu Thr Ile Thr Leu Thr Pro Lys Val Thr Cys Val Val Asp
                    20                  25                  30

Ile Ser Gln Asp Asp Pro Glu Val His Phe Ser Trp Phe Val Asp Asp
                    35                  40                  45

Val Glu Val His Thr Ala Gln Thr Arg Pro Pro Glu Glu Gln Phe Asn
        50                  55                  60

Ser Thr Phe Arg Ser Val Ser Glu Leu Pro Ile Leu His Gln Asp Trp
65                      70                  75                      80

Leu Asn Gly Arg Thr Phe Arg Cys Lys Val Thr Ser Ala Ala Phe Pro
                    85                  90                  95

Ser Pro Ile Glu Lys Thr Ile Ser Lys Pro Glu
                    100                 105

<210> SEQ ID NO 64
<211> LENGTH: 110
<212> TYPE: PRT
<213> ORGANISM: Rattus norvegicus

<400> SEQUENCE: 64

Val Pro Glu Leu Leu Gly Gly Pro Ser Val Phe Ile Phe Pro Pro Lys
1                   5                   10                  15

Pro Lys Asp Ile Leu Leu Ile Ser Gln Asn Ala Lys Val Thr Cys Val
                    20                  25                  30

Val Val Asp Val Ser Glu Glu Glu Pro Asp Val Gln Phe Ser Trp Phe
                    35                  40                  45

Val Asn Asn Val Glu Val His Thr Ala Gln Thr Gln Pro Arg Glu Glu
        50                  55                  60

Gln Tyr Asn Ser Thr Phe Arg Val Val Ser Ala Leu Pro Ile Gln His
65                      70                  75                      80

Gln Asp Trp Met Ser Gly Lys Glu Phe Lys Cys Lys Val Asn Asn Lys
                    85                  90                  95

Ala Leu Pro Ser Pro Ile Glu Lys Thr Ile Ser Lys Pro Lys
                    100                 105                 110

<210> SEQ ID NO 65
<211> LENGTH: 109
<212> TYPE: PRT
<213> ORGANISM: Rattus norvegicus

<400> SEQUENCE: 65

Asp Asp Asn Leu Gly Arg Pro Ser Val Phe Ile Phe Pro Pro Lys Pro
1                   5                   10                  15

Lys Asp Ile Leu Met Ile Thr Leu Thr Pro Lys Val Thr Cys Val Val
                    20                  25                  30

Val Asp Val Ser Glu Glu Glu Pro Asp Val Gln Phe Ser Trp Phe Val
                    35                  40                  45

Asp Asn Val Arg Val Phe Thr Ala Gln Thr Gln Pro His Glu Glu Gln
        50                  55                  60

Leu Asn Gly Thr Phe Arg Val Val Ser Thr Leu His Ile Gln His Gln
65                      70                  75                      80

Asp Trp Met Ser Gly Lys Glu Phe Lys Cys Lys Val Asn Asn Lys Asp
                    85                  90                  95

Leu Pro Ser Pro Ile Glu Lys Thr Ile Ser Lys Pro Arg
                    100                 105

<210> SEQ ID NO 66
```

```
<211> LENGTH: 118
<212> TYPE: PRT
<213> ORGANISM: Artificial Sequence
<220> FEATURE:
<223> OTHER INFORMATION: chemically synthesized

<400> SEQUENCE: 66

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Pro Ser Asp Ala Phe Pro Tyr Trp Gly Gln Gly Thr
            100                 105                 110

Leu Val Thr Val Ser Ser
        115

<210> SEQ ID NO 67
<211> LENGTH: 354
<212> TYPE: DNA
<213> ORGANISM: Artificial Sequence
<220> FEATURE:
<223> OTHER INFORMATION: chemically synthesized

<400> SEQUENCE: 67
caggtgcagc ttcaggagtc cggcccagga ctggtgaagc cttcggacac cctgtccctc    60
acctgcgctg tctctggtta ctccatcacc ggtggttata gctggcactg gatacggcag   120
cccccaggga agggactgga gtggatgggg tatatccact acagtggtta cactgacttc   180
aacccctccc tcaagactcg aatcaccata tcacgtgaca cgtccaagaa ccagttctcc   240
ctgaagctga gctctgtgac cgctgtggac actgcagtgt attactgtgc gagaaaagat   300
ccgtccgacg cctttcctta ctggggccaa gggactctgg tcactgtctc ttcc         354

<210> SEQ ID NO 68
<211> LENGTH: 118
<212> TYPE: PRT
<213> ORGANISM: Artificial Sequence
<220> FEATURE:
<223> OTHER INFORMATION: chemically synthesized

<400> SEQUENCE: 68

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
```

```
                        85                  90                  95
Ala Arg Lys Asp Pro Ser Glu Gly Phe Pro Tyr Trp Gly Gln Gly Thr
            100                 105                 110

Leu Val Thr Val Ser Ser
        115

<210> SEQ ID NO 69
<211> LENGTH: 354
<212> TYPE: DNA
<213> ORGANISM: Artificial Sequence
<220> FEATURE:
<223> OTHER INFORMATION: chemically synthesized

<400> SEQUENCE: 69
caggtgcagc ttcaggagtc cggcccagga ctggtgaagc cttcggacac cctgtccctc      60
acctgcgctg tctctggtta ctccatcacc ggtggttata gctggcactg gatacggcag     120
cccccaggga agggactgga gtggatgggg tatatccact acagtggtta cactgacttc     180 aaccccctccc tcaagactcg aatcaccata tcacgtgaca cgtccaagaa ccagttctcc    240
ctgaagctga gctctgtgac cgctgtggac actgcagtgt attactgtgc gagaaaagat    300
ccgtccgagg gatttcctta ctggggccaa gggactctgg tcactgtctc ttcc           354

<210> SEQ ID NO 70
<211> LENGTH: 354
<212> TYPE: DNA
<213> ORGANISM: Artificial Sequence
<220> FEATURE:
<223> OTHER INFORMATION: chemically synthesized

<400> SEQUENCE: 70
caggtgcagc ttcaggagtc cggcccagga ctggtgaagc cttcggacac cctgtccctc      60
acctgcgctg tctctggtta ctccatcacc ggtggttata gctggcactg gatacggcag     120
cccccaggga agggactgga gtggatgggg tatatccact acagtggtta cactgacttc     180 aaccccctccc tcaagactcg aatcaccata tcacgtgaca cgtccaagaa ccagttctcc    240
ctgaagctga gctctgtgac cgctgtggac actgcagtgt attactgtgc gagaaaagat    300
ccgtccgacg gatttcctta ctggggccaa gggactctgg tcactgtctc ttcc           354

<210> SEQ ID NO 71
<211> LENGTH: 107
<212> TYPE: PRT
<213> ORGANISM: Artificial Sequence
<220> FEATURE:
<223> OTHER INFORMATION: chemically synthesized

<400> SEQUENCE: 71

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Asn Ser His Ser Phe Pro Leu
                85                  90                  95
```

Thr Phe Gly Gly Gly Thr Lys Val Glu Ile Lys
            100                 105

<210> SEQ ID NO 72
<211> LENGTH: 321
<212> TYPE: DNA
<213> ORGANISM: Artificial Sequence
<220> FEATURE:
<223> OTHER INFORMATION: chemically synthesized

<400> SEQUENCE: 72

```
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagaat agtcacagtt ttccgctcac tttcggcgga     300
gggaccaagg tggagatcaa a                                                321
```

<210> SEQ ID NO 73
<211> LENGTH: 107
<212> TYPE: PRT
<213> ORGANISM: Artificial Sequence
<220> FEATURE:
<223> OTHER INFORMATION: chemically synthesized

<400> SEQUENCE: 73

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys
            100                 105

<210> SEQ ID NO 74
<211> LENGTH: 321
<212> TYPE: DNA
<213> ORGANISM: Artificial Sequence
<220> FEATURE:
<223> OTHER INFORMATION: chemically synthesized

<400> SEQUENCE: 74

```
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag ggtcacagtt ttccgctcac tttcggcgga     300
gggaccaagg tggagatcaa a                                                321
```

<210> SEQ ID NO 75

```
<211> LENGTH: 107
<212> TYPE: PRT
<213> ORGANISM: Artificial Sequence
<220> FEATURE:
<223> OTHER INFORMATION: chemically synthesized

<400> SEQUENCE: 75
```

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Asn Ser Ser Ser Phe Pro Leu
                85                  90                  95

Thr Phe Gly Gly Gly Thr Lys Val Glu Ile Lys
            100                 105

```
<210> SEQ ID NO 76
<211> LENGTH: 321
<212> TYPE: DNA
<213> ORGANISM: Artificial Sequence
<220> FEATURE:
<223> OTHER INFORMATION: chemically synthesized

<400> SEQUENCE: 76
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagaat agtagtagtt ttccgctcac tttcggcgga     300
gggaccaagg tggagatcaa a                                               321

<210> SEQ ID NO 77
<211> LENGTH: 107
<212> TYPE: PRT
<213> ORGANISM: Artificial Sequence
<220> FEATURE:
<223> OTHER INFORMATION: chemically synthesized

<400> SEQUENCE: 77
```

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Ser Phe Pro Leu
                85                  90                  95

Thr Phe Gly Gly Gly Thr Lys Val Glu Ile Lys

<210> SEQ ID NO 78
<211> LENGTH: 321
<212> TYPE: DNA
<213> ORGANISM: Artificial Sequence
<220> FEATURE:
<223> OTHER INFORMATION: chemically synthesized

<400> SEQUENCE: 78

```
gaaattgtgt tgacgcagtc tccagacttt cagtctgtga ctccaaagga aaaagtcacc    60
atcacctgca gggccagtca gagtatcagc gaccacttac actggtacca acagaaacct   120
gatcagtctc ccaagctcct catcaaatat gcttcccatg ccatttctgg ggtcccatcg   180
aggttcagtg gcagtgggtc tgggacagac ttcactctca ccatcaatag cctagaggct   240
gaagatgctg caacgtatta ctgtcagcag agtcacagtt ttccgctcac tttcggcgga   300
gggaccaagg tggagatcaa a                                             321
```

<210> SEQ ID NO 79
<211> LENGTH: 321
<212> TYPE: DNA
<213> ORGANISM: Artificial Sequence
<220> FEATURE:
<223> OTHER INFORMATION: chemically synthesized

<400> SEQUENCE: 79

```
gaaattgtgt tgacgcagtc tccagacttt cagtctgtga ctccaaagga aaaagtcacc    60
atcacctgca gggccagtca gagtatcagc gaccacttac actggtacca acagaaacct   120
gatcagtctc ccaagctcct catcaaatat gcttcccatg ccatttctgg ggtcccatcg   180
aggttcagtg gcagtgggtc tgggacagac ttcactctca ccatcaatag cctagaggct   240
gaagatgctg caacgtatta ctgtcagaat ggtcacagtt ttccgctcac tttcggcgga   300
gggaccaagg tggagatcaa a                                             321
```

<210> SEQ ID NO 80
<211> LENGTH: 9
<212> TYPE: PRT
<213> ORGANISM: Artificial Sequence
<220> FEATURE:
<223> OTHER INFORMATION: chemically synthesized

<400> SEQUENCE: 80

Lys Asp Pro Ser Asp Ala Phe Pro Tyr
1               5

<210> SEQ ID NO 81
<211> LENGTH: 9
<212> TYPE: PRT
<213> ORGANISM: Artificial Sequence
<220> FEATURE:
<223> OTHER INFORMATION: chemically synthesized

<400> SEQUENCE: 81

Lys Asp Pro Ser Glu Gly Phe Pro Tyr
1               5

<210> SEQ ID NO 82
<211> LENGTH: 9
<212> TYPE: PRT
<213> ORGANISM: Artificial Sequence
<220> FEATURE:
<223> OTHER INFORMATION: chemically synthesized

```
<400> SEQUENCE: 82

Gln Asn Ser His Ser Phe Pro Leu Thr
1               5

<210> SEQ ID NO 83
<211> LENGTH: 9
<212> TYPE: PRT
<213> ORGANISM: Artificial Sequence
<220> FEATURE:
<223> OTHER INFORMATION: chemically synthesized

<400> SEQUENCE: 83

Gln Gln Gly His Ser Phe Pro Leu Thr
1               5

<210> SEQ ID NO 84
<211> LENGTH: 9
<212> TYPE: PRT
<213> ORGANISM: Artificial Sequence
<220> FEATURE:
<223> OTHER INFORMATION: chemically synthesized

<400> SEQUENCE: 84

Gln Asn Ser Ser Ser Phe Pro Leu Thr
1               5

<210> SEQ ID NO 85
<211> LENGTH: 9
<212> TYPE: PRT
<213> ORGANISM: Artificial Sequence
<220> FEATURE:
<223> OTHER INFORMATION: chemically synthesized

<400> SEQUENCE: 85

Gln Gln Ser His Ser Phe Pro Leu Thr
1               5

<210> SEQ ID NO 86
<211> LENGTH: 4
<212> TYPE: PRT
<213> ORGANISM: Artificial Sequence
<220> FEATURE:
<223> OTHER INFORMATION: chemically synthesized

<400> SEQUENCE: 86

Ser Ala Ala Phe
1

<210> SEQ ID NO 87
<211> LENGTH: 4
<212> TYPE: PRT
<213> ORGANISM: Artificial Sequence
<220> FEATURE:
<223> OTHER INFORMATION: chemically synthesized

<400> SEQUENCE: 87

Ser Lys Ala Phe
1

<210> SEQ ID NO 88
<211> LENGTH: 4
<212> TYPE: PRT
<213> ORGANISM: Artificial Sequence
<220> FEATURE:
<223> OTHER INFORMATION: chemically synthesized

<400> SEQUENCE: 88
```

Asn Ala Ala Phe
1

<210> SEQ ID NO 89
<211> LENGTH: 4
<212> TYPE: PRT
<213> ORGANISM: Artificial Sequence
<220> FEATURE:
<223> OTHER INFORMATION: chemically synthesized

<400> SEQUENCE: 89

Asn Lys Ala Phe
1

<210> SEQ ID NO 90
<211> LENGTH: 22
<212> TYPE: PRT
<213> ORGANISM: Mus musculus

<400> SEQUENCE: 90

Phe Lys Cys Arg Val Asn Ser Ala Ala Phe Pro Ala Pro Ile Glu Lys
1               5                   10                  15

Thr Ile Ser Lys Thr Lys
            20

<210> SEQ ID NO 91
<211> LENGTH: 22
<212> TYPE: PRT
<213> ORGANISM: Artificial Sequence
<220> FEATURE:
<223> OTHER INFORMATION: chemically synthesized

<400> SEQUENCE: 91

Tyr Lys Cys Lys Val Ser Asn Lys Ala Leu Pro Ala Pro Ile Glu Lys
1               5                   10                  15

Thr Ile Ser Lys Ala Lys
            20

<210> SEQ ID NO 92
<211> LENGTH: 22
<212> TYPE: PRT
<213> ORGANISM: Artificial Sequence
<220> FEATURE:
<223> OTHER INFORMATION: chemically synthesized

<400> SEQUENCE: 92

Phe Lys Cys Arg Val Asn Ser Ala Ala Phe Pro Ala Pro Ile Glu Lys
1               5                   10                  15

Thr Ile Ser Lys Ala Lys
            20

<210> SEQ ID NO 93
<211> LENGTH: 22
<212> TYPE: PRT
<213> ORGANISM: Artificial Sequence
<220> FEATURE:
<223> OTHER INFORMATION: chemically synthesized

<400> SEQUENCE: 93

Tyr Lys Cys Lys Val Asn Ser Ala Ala Phe Pro Ala Pro Ile Glu Lys
1               5                   10                  15

Thr Ile Ser Lys Ala Lys
            20

<210> SEQ ID NO 94

```
<211> LENGTH: 22
<212> TYPE: PRT
<213> ORGANISM: Artificial Sequence
<220> FEATURE:
<223> OTHER INFORMATION: chemically synthesized

<400> SEQUENCE: 94

Tyr Lys Cys Lys Val Ser Ser Ala Ala Phe Pro Ala Pro Ile Glu Lys
1               5                   10                  15

Thr Ile Ser Lys Ala Lys
            20

<210> SEQ ID NO 95
<211> LENGTH: 22
<212> TYPE: PRT
<213> ORGANISM: Artificial Sequence
<220> FEATURE:
<223> OTHER INFORMATION: chemically synthesized

<400> SEQUENCE: 95

Tyr Lys Cys Lys Val Ser Ser Ala Ala Leu Pro Ala Pro Ile Glu Lys
1               5                   10                  15

Thr Ile Ser Lys Ala Lys
            20

<210> SEQ ID NO 96
<211> LENGTH: 22
<212> TYPE: PRT
<213> ORGANISM: Artificial Sequence
<220> FEATURE:
<223> OTHER INFORMATION: chemically synthesized

<400> SEQUENCE: 96

Tyr Lys Cys Lys Val Ser Asn Ala Ala Leu Pro Ala Pro Ile Glu Lys
1               5                   10                  15

Thr Ile Ser Lys Ala Lys
            20

<210> SEQ ID NO 97
<211> LENGTH: 4
<212> TYPE: PRT
<213> ORGANISM: Artificial Sequence
<220> FEATURE:
<223> OTHER INFORMATION: chemically synthesized

<400> SEQUENCE: 97

Asn Lys Ala Leu
1

<210> SEQ ID NO 98
<211> LENGTH: 4
<212> TYPE: PRT
<213> ORGANISM: Artificial Sequence
<220> FEATURE:
<223> OTHER INFORMATION: chemically synthesized

<400> SEQUENCE: 98

Asn Ala Ala Leu
1

<210> SEQ ID NO 99
<211> LENGTH: 4
<212> TYPE: PRT
<213> ORGANISM: Artificial Sequence
<220> FEATURE:
<223> OTHER INFORMATION: chemically synthesized
```

```
<400> SEQUENCE: 99

Ser Ala Ala Leu
1

<210> SEQ ID NO 100
<211> LENGTH: 4
<212> TYPE: PRT
<213> ORGANISM: Artificial Sequence
<220> FEATURE:
<223> OTHER INFORMATION: chemically synthesized

<400> SEQUENCE: 100

Ser Gly Ala Phe
1
```